(12) United States Patent
Ferrante et al.

(10) Patent No.: US 6,924,309 B2
(45) Date of Patent: Aug. 2, 2005

(54) ANTI-INFLAMMATORY NITRO AND THIA-FATTY ACIDS

(75) Inventors: Antonio Ferrante, North Adelaide (AU); Christopher J. Easton, North Adelaide (AU); Ling Xia, North Adelaide (AU)

(73) Assignees: Children, Youth and Women's Health Service Incorporated, North Adelaide (AU); Peptech Limited, New South Wales (AU)

( * ) Notice: Subject to any disclaimer, the term of this patent is extended or adjusted under 35 U.S.C. 154(b) by 0 days.

(21) Appl. No.: 10/100,490

(22) Filed: Mar. 18, 2002

(65) Prior Publication Data

US 2003/0092762 A1 May 15, 2003

Related U.S. Application Data

(63) Continuation of application No. PCT/AU00/01138, filed on Sep. 18, 2000.

(30) Foreign Application Priority Data

Sep. 17, 1999 (AU) .............................................. PQ2914

(51) Int. Cl.[7] ...................... A01N 37/00; A61K 31/20; C07C 229/00; C07C 207/00; C07C 205/00
(52) U.S. Cl. ...................... 514/560; 554/111; 562/553; 562/571
(58) Field of Search ........................ 514/560; 562/553; 562/571, 567, 568; 554/111, 103, 110

(56) References Cited

U.S. PATENT DOCUMENTS 3,415,856 A * 12/1968 Lachowicz et al. ......... 260/413
3,578,687 A * 5/1971 Larkin et al. ............... 260/404

FOREIGN PATENT DOCUMENTS

GB 587992 * 6/1947

OTHER PUBLICATIONS

Kobayashi, T., "The reaction of nitrogen dioxide with lung surface components: the reaction of cis–9–octadecenoic acid" Chemosphere, vol. 12(9–10), pp. 1317–1325 (1983). [CAS Online Abstract].*

Doering et al, "Toxicity of myristic acid analogs toward African typanosomes" Proc. Natl. Acad. Sci. vol. 91, pp. 9735–9739 (Oct. 1994).*

Gupta et al, "Nitration of .beta. and .gamma. acetoxy olefinic fatty acids" Journal of the Oil Technologists' Association of India, vol. 18(2), pp. 46–49 (1986). (as abstracted by CAPLUS).*

D'lschia et al, "Medium–dependent Competitive Pathways in the Reactions of Polyunsaturated Fatty Acids with Nitric Oxide in the Presence of Oxygen ..." Tetrahedron, vol. 55, pp 9297–9307 (Jul., 1999).*

Lima et al, "Characterization of Linoleic Acid Nitration in Human Blood Plasma by Mass Spectrometry" Biochemistry, vol. 41, pp. 10717–10722 (2002).*

* cited by examiner

Primary Examiner—Richard L. Raymond
Assistant Examiner—Zachary C. Tucker
(74) Attorney, Agent, or Firm—Klauber & Jackson

(57) ABSTRACT

The present invention relates to compounds of the general formula: $NO_2$-A-B wherein A is a saturated or unsaturated hydrocarbon chain of 14–26 carbon atoms and B is $(CH_2)_n(COOH)_m$ in which n is an integer from 0 to 2 and m is an integer from 0 to 2; or of general formula (I), wherein A' is a saturated or unsaturated hydrocarbon chain of 9–26 carbon atoms, X is oxygen or is absent and B' is $(CH_2)_j(COOH)_k$ in which j is an integer from 1 to 3 and k is 0 or 1; and the derivatives thereof in which the hydrocarbon chain includes one or more than one substitution selected from the group consisting of hydroxy, hydroperoxy, epoxy and peroxy. These compounds have biological activity, e.g. as anti-infective or anti-inflammatory agents.

7 Claims, 7 Drawing Sheets

☒ Initial Parasitaemia
☐ 5 hours after treatment

☒ Control
☐ With 20:4

ANTI-INFLAMMATORY NITRO AND THIA-FATTY ACIDS

This application is a continuation of international application number PCT AU00/01138, filed Sep. 18, 2000.

FIELD OF THE INVENTION

The present invention relates to compounds which include a carbon chain of 14 to 26 carbon atoms and a nitro or sulphur group. In a particular embodiment the invention relates to nitro analogues of polyunsaturated fatty acids. The present invention further relates to the use of these compounds in methods of treatment.

BACKGROUND OF THE INVENTION

Fatty acids are one of the most extensively studied classes of compounds due to their important role in biological systems [1,2]. Hundreds of different fatty acids exist in nature. They consist of saturated, monounsaturated and polyunsaturated fatty acids, having chain lengths from 4 to 22 carbon atoms. Polyunsaturated fatty acids (PUFAS) contain 16 to 22 carbon atoms with two or more methylene-interrupted double bonds. The PUFA, arachidonic acid, contains 20 carbons and four methylene-interrupted cis-double bonds commencing six carbons from the terminal methyl group, which therefore leads to an abbreviated nomenclature of 20:4 (n-6).

PUFAs can be divided into four families, based on the parent fatty acids from which they are derived: linoleic acid (18:2 n-6), α-linolenic acid (18:3 n-3), oleic acid (18:1 n-9) and palmitoleic acid (16:1 n-7). The n-6 and n-3 PUFAs cannot be synthesised by mammals and are known as essential fatty acids (EFAs). They are required by mammalian bodies indirectly through desaturation or elongation of linoleic and α-linolenic acids, which must be supplied in the diet.

EFAs have a variety of biological activities. For instance, it has been suggested that they can play an important role in modulating cystic fibrosis[3]. Intake of n-3 PUFAs has been found to be associated with a reduced incidence of coronary arterial diseases, and various mechanisms by which n-3 PUFAs act have been proposed.[4,5] Some n-3 and n-6 PUFAs also possess antimalarial [6] or anti-inflammatory properties.[7] Furthermore, one of the EFAs' most important biological roles is to supply precursors for the production of bioactive fatty acid metabolites that can modulate many immune functions.[8]

Arachidonic acid (AA) is the most extensively studied of the EFAs and it is a principal precursor for many important biological mediators. There are two pathways for arachidonic acid metabolism (1) the cycloxygenase pathway which leads to the formation of prostaglandins and thromboxanes, and (2) the lipoxygenase pathway which is responsible for the generation of leukotrienes and lipoxins. These metabolites, collectively called eicosanoids, have been implicated in the pathology of a variety of diseases such as asthma[9] and other inflammatory disorders.[10,11]

Although EFAs play important roles in the biological process of the mammalian body; they are not widely used as therapeutics due to their limited availability in vivo. They are readily degradable by β-oxidation, which is the major oxidative pathway in fatty acid metabolism. The net process of β-oxidation is characterised by the degradation of the fatty acid carbon chain by two carbon atoms with the concomitant production of equimolar amounts of acetyl-coenzyme A.

To overcome the problem of β-oxidation, some work has been done to design and synthesise modified PUFAS, such as the β-oxa and β-thia PUFAs[12,13]. These compounds were shown to have enhanced resistance to β-oxidation while still retaining certain biological activities of the native PUFAs.

The present invention relates to the design and preparation of another group of modified PUFAS, the nitro analogues of PUFAS. The rationale was that the nitro group is chemically similar to COOH group with regard to size, charge and shape. In addition, the nitro compounds are a group of relatively stable compounds and are resistant to β-oxidation by preventing CoA thioester production, which is the first step in β-oxidation of fatty acids. This also means that the nitro compounds will not be incorporated into lipids and will more likely be present in a free form.

SUMMARY OF THE PRESENT INVENTION

Figure 1:
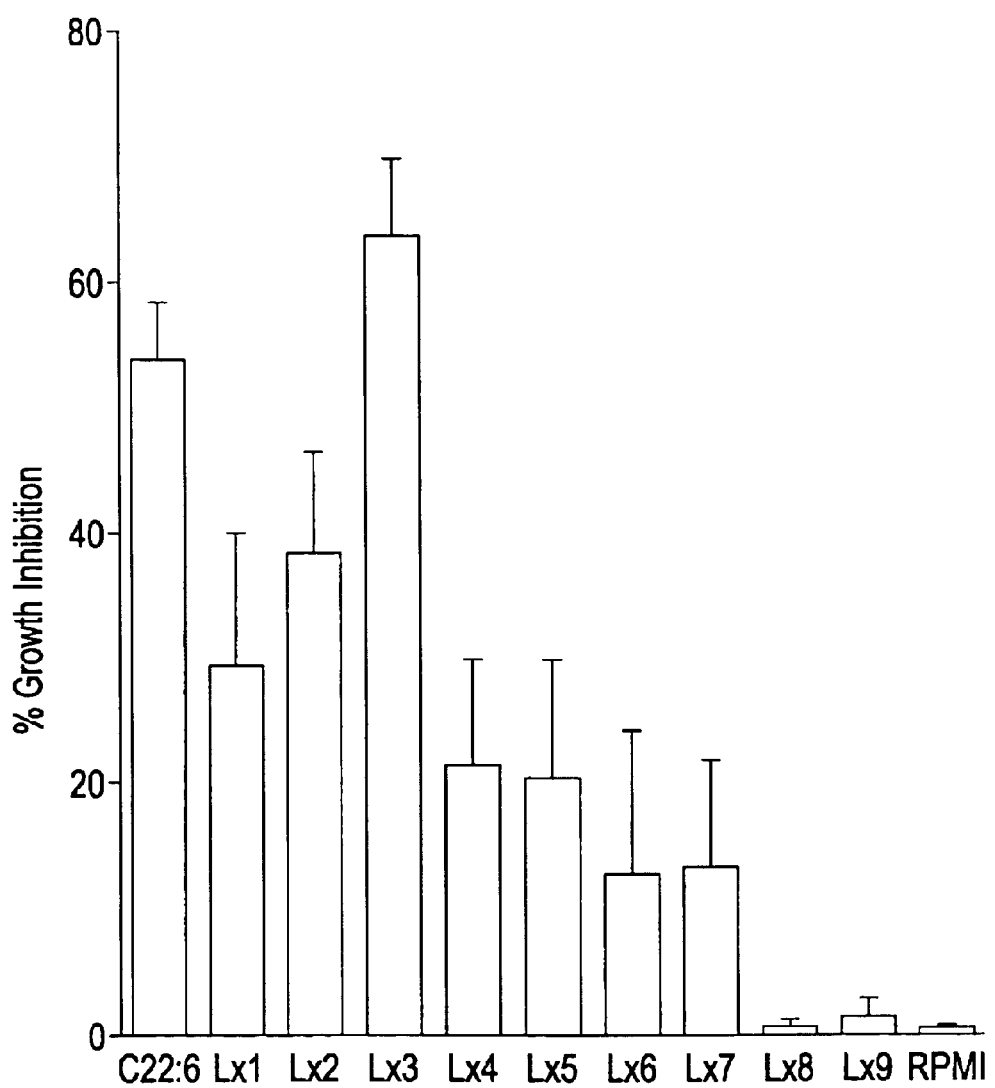
FIG. 1 illustrates the effects of chemically engineered nitro compounds on $P.$ $falciparum$ 3D7. Results are the mean +/−SEM of 3 to 10 experiments. It can be seen that 19:3(n-6)-NO2(Lx3) had the greatest activity. The compounds Lx1 to Lx5 did not contain a carboxyl group. In terms of these five compounds it is evident that, apart from Lx3, there was no increase in antimalarial activity of the compounds by introducing double bonds.

In a first aspect, the present invention consists in a compound of the general formula:

in which A is a saturated or unsaturated hydrocarbon chain of 14 to 26 carbon atoms; and B is $(CH_2)_n(COOH)_m$ in which n is 0 to 2 and m is 0 to 2; and the derivatives thereof having a further one or more than one substitution selected from the group consisting of hydroxy, hydroperoxy, epoxy and peroxy.

In a preferred embodiment of the present invention, A is a hydrocarbon chain of 18 to 22 carbon atoms which is preferably polyunsaturated, and in particular has 3–6 double bonds.

More preferably, the compound has an unsaturated hydrocarbon chain having 18 carbon atoms and three double bonds separated by methylene groups, with the first double bond relative to the omega carbon atom being between the $3^{rd}$ and $4^{th}$ or $6^{th}$ and $7^{th}$ carbon atoms.

In a further preferred embodiment, the compound is selected from the group consisting of those set out in Table 1.

TABLE 1

Structure and nomenclature of nitro fatty acid analogues

| Structure | Systematic Name | WCH | Report | Thesis |
|---|---|---|---|---|
| 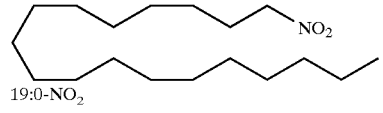 19:0-NO$_2$ | 1-Nitrooctadecane | Lx1 | 4a | 55 |
| 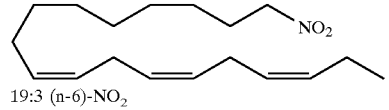 19:3 (n-6)-NO$_2$ | (z,z,z)-1-Nitro-9,12,15-octadecatriene | Lx2 | 4c | 60a |
| 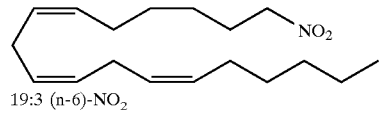 19:3 (n-6)-NO$_2$ | (z,z,z)-1-Nitro-6,9,12-octadecatriene | Lx3 | 4d | 60b |
| 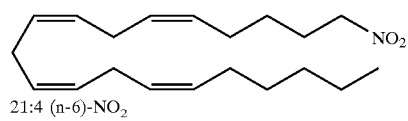 21:4 (n-6)-NO$_2$ | (a11-z)-1-Nitro-5,8,11,14-eicosatetraene | Lx4 | 4b | 60c |
| 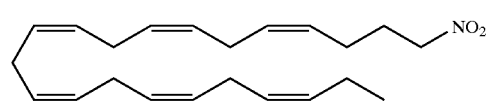 23:6 (n-3)-NO$_2$ | (a11-z)-1-Nitro-4,7,10,13,16,19-docosahexaene | Lx5 | 4e | 60 |
| 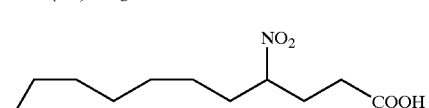 21:0γ-NO$_2$ | 4-Nitrohenicosanoic acid | Lx6 | 6a | 80 |
| 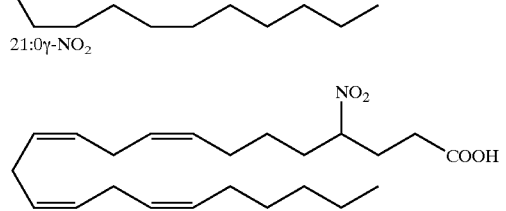 | (a11-Z)-4-Nitrotricosa-8,11,14,17-tetraenoic acid | Lx7 | 6b | 82 |

TABLE 1-continued

Structure and nomenclature of nitro fatty acid analogues

| Structure | Systematic Name | WCH | Report | Thesis |
|---|---|---|---|---|
| 23:4 (n-6)γ-NO$_2$ 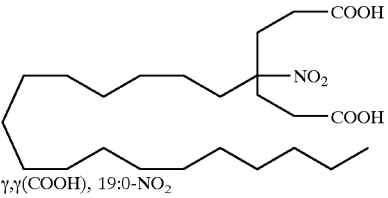 γ,γ(COOH), 19:0-NO$_2$ | 3-Heptadecyl-3-nitropentane-1,5-dicarboxylic acid | Lx8 | 8a | 84 |
| 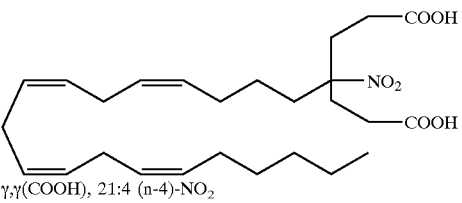 γ,γ(COOH), 21:4 (n-4)-NO$_2$ | 3-[(a11-Z)-Nonadeca-4,7,10,13-tetraenyl] 4-nitroheptane-1,7-dicarboxylic acid | Lx9 | 8b | 86 |

In yet a further preferred embodiment, the compound is Lx2 or Lx3.

In yet a further preferred embodiment, the compound is Lx7 or Lx9.

The compounds of the present invention are useful as anti-infectives and show anti-malarial activity.

The biological properties of the compounds studied to date also suggest that these compounds could form the basis for therapeutics in treatment of infectious diseases e.g. malaria. They may also find application in the treatment of autoimmune and allergic inflammatory diseases.

Their ability to penetrate cells and tissues also suggests their use as drug or antigen carriers. The compounds could also be used to prevent oxidative damage including as anti-ageing agents.

The ability of a number of the compounds to inhibit lipoxygenase activity suggests that the compounds may be useful to treat asthma where leukotrienes are major mediators of airways' hyperactivity.

Asthma is a serious, chronic inflammatory condition with a number of characteristic features in addition to acute airway constriction. These include inflammatory cell recruitment and activation, mucous hypersecretion, airway hyperreactivity and changes in airway morphology. The understanding of the inflammatory process may be the key to choosing the appropriate therapy for asthmatic patients. The standard treatment currently available for the long term management of the inflammation associated with asthma is the corticosteroids. However, these have unwanted side-effects. It is well established that the airways of individuals with asthma are infiltrated with leukocytes that can produce inflammatory mediators. Among the inflammatory mediators implicated in the asthmatic lesion are the cysteinyl-leukotrienes predominantly elaborated by eosinophils, neutrophils and monocytes. The leukotrienes belong to a family of structurally similar compounds derived from 20:4(n-6), of which the most active are the cysteinyl-leukotrienes [leukotriene C$_4$ (LTC$_4$), leukotriene D$_4$ (LTD$_4$) and leukotriene E$_4$ (LTE$_4$)] and the dihydroxylated fatty acid, leukotriene B$_4$ (LTB$_4$). Apart from being potent mediators of airway obstruction, these compounds are implicated in the pathogenesis of a number of inflammatory disorders, including cystic fibrosis, rheumatoid arthritis, systemic lupus erythematosis and cardiovascular diseases. Modulation of the effects of leukotrienes has been attempted by inhibiting the synthesis of these eicosanoids with eicosapentaenoic acid [20:5(n-3)] and docosahexaenoic acid [22:6(n-3)], which are enriched in fish oil diets. Unfortunately, the results of such strategies have been controversial and disappointing.

The ability of the compounds to inhibit IFN-γ and TNF makes the substances useful to treat autoimmune diseases e.g. systemic lupus erythromatosis, multiple sclerosis, rheumatoid arthritis, ischaemia, adult respiratory distress syndrome, inflammatory bowel diseases and cystic fibrosis. The compounds may also be useful in the treatment of allergy and skin diseases where IFN-γ plays a pathogenic role e.g. atopic dermatitis.

The metabolism of arachidonic acid has been a topic of great interest, particularly in relation to its role in inflammation. A major interest has been the search for selective inhibitors of the various enzymes in the arachidonic acid cascade. This is critical for the development of compounds with therapeutic potential for control of the pathological processes mediated by arachidonic acid metabolites, and is also important in providing useful biochemical tools for mechanistic investigation of the enzymes involved. Considerable effort in this area has been made in association with the cycloxygenase pathway, and a number of nonsteroidal anti-inflammatory drugs (e.g. aspirin and indomethacin) have been found to have inhibitory effects on cycloxygenase.[14] More recently, efforts have been extended to a study of the lipoxygenase (LO) pathway and the search for selective inhibitors of the enzymes involved in the pathway. Another major objective of the present work is to assess the possible activity for enzyme inhibition or other potential physiological activities of the synthetic nitro compounds using enzymological and biological assays.

In a second aspect, the present invention consists in a therapeutic composition comprising at least one compound of the first aspect of the present invention and a pharmaceutically acceptable carrier or diluent.

In a third aspect, the present invention consists in a method of treating a condition, selected from the group consisting of infection (eg malaria, and in particular malaria caused by the malaria parasite *Plasmodium falciparum* or *Plasmodium vivax*), inflammation, a condition involving elevated levels of unesterified arachidonic acid or products of arachidonic acid metabolism (eg psoriasis, allergic asthma, rhinitis, leukoclastic vasculitis, urticaria or angiodema), asthma, autoimmune disease, systemic lupus erythromatosis, multiple sclerosis, rheumatoid arthritis, ischaemia, adult respiratory distress syndrome, inflammatory bowel diseases, cystic fibrosis, allergy and skin diseases where IFN-γ plays a pathogenic role e.g. atopic dermatitis, in a subject, the method comprising administering to the subject a therapeutic amount of the compound of the first aspect of the present invention.

In a fourth aspect, the present invention consists in a compound of the general formula:

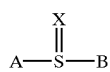

in which A is a saturated or unsaturated hydrocarbon chain of 9 to 26 carbon atoms; X is oxygen or is absent; and B is $(CH_2)_j(COOH)_k$ in which j is an integer from 1 to 3 and k is 0 or 1; and the derivatives thereof in which the hydrocarbon chain includes one or more than one substitution selected from the group consisting of hydroxy, hydroperoxy, epoxy and peroxy.

Such compounds, with the exception of some compounds comprising both an unsaturated hydrocarbon chain and a carboxyl group, are novel.

In a preferred embodiment of the present invention, A is a hydrocarbon chain of 14 to 18 carbon atoms which is preferably saturated.

In a further preferred embodiment, the compound is selected from the group consisting of compounds 108, 109, 110, 111, 113 and 114 set out in Table 7.

In yet a further preferred embodiment, the compound is Lx7 or Lx9.

The compounds of the fourth aspect of the present invention are useful as anti-oxidants.

In a fifth aspect, the present invention consists in a therapeutic composition comprising at least one compound of the fourth aspect of the present invention and a pharmaceutically acceptable carrier or diluent.

In a sixth aspect, the present invention consists in a method of treating or ameliorating the symptoms of a condition involving elevated levels of unesterified arachidonic acid or products of arachidonic acid metabolism in a subject, the method comprising administering to the subject a therapeutic amount of a compound of the fourth aspect of the present invention.

In a seventh aspect, the present invention consists in a method of treating an infection or an inflammatory disease (eg as listed with respect to the third aspect if the invention) in a subject, the method comprising administering to the subject a therapeutic amount of a compound of the fourth aspect of the present invention.

In order that the nature of the present invention may be more clearly understood, preferred forms thereof will now be described with reference to the following examples.

A. Preparation of Nitro Analogues of PUFA (1) Synthesis of Nitroalkanes/Nitroalkenes (Lx1 to Lx5)

The first target compounds were a series of nitro compounds with chain lengths of 18 to 22 carbons and 3 to 5 double bonds, being prepared by modification of commercially available polyunsaturated fatty alcohols. Since the unsaturated alcohols are relatively expensive to obtain, stearyl alcohol was used as the starting material for establishing synthetic methods.

The synthesis of nitroalkanes/nitroalkenes [15] Lx]1 to Lx5 is summarised in Scheme 1.

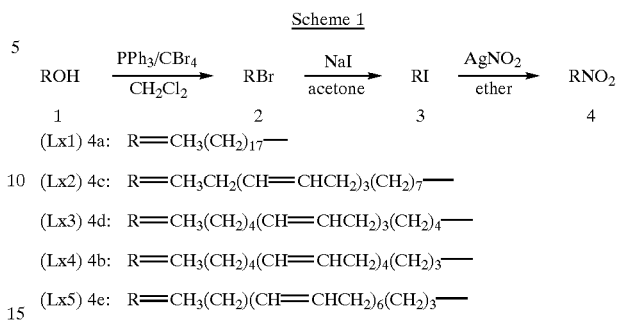

Stearyl alcohol 1a was converted to stearyl bromide 2a by treatment with triphenyl phosphine ($PPh_3$) and carbon tetrabromide ($CBr_4$) in dichloromethane overnight at room temperature. After purification by flash chromatography on silica gel, stearyl bromide 2a was obtained in 96% yield. Treatment at the stearyl bromide with silver nitrate in ether afforded stearyl nitrate 4a in low yield (<10%). Attempts to improve the yield of the nitroalkane 4a from this procedure by extending reaction time and increasing the amount of silver nitrate used were unsuccessful and so conversion of the bromide to the nitroalkane via the iodide was investigated. Conversion of stearyl bromide 2a to the corresponding iodide 3a was achieved in the yields of >90% as estimated by the $^1H$ NMR spectrum of crude reaction mixture. Stearyl iodide 3a was converted in situ to stearyl nitrate 4a, by treatment with silver nitrate in ether for 3 days at room temperature, and the product, stearyl nitrate 4a, was obtained in 65% yield. Based on this approach, nitroalkenes 4b–4e were synthesised and fully characterised (Scheme 1).

(2) Synthesis of γ-nitroalkanoic and γ-nitroalkenoic Acids [6a (Lx6) and 6b (Lx7)]

The synthetic nitroalkane and nitroalkene (Lx1 and Lx4) were further used as starting material for synthesis of γ-nitroalkanoic and γ-nitroalkenoic acids (Lx6 and Lx7). The γ-nitroalkanoic and γ-nitroalkenoic acid esters 5a and 5b were produced by Michael addition of the respective nitroalkane and nitroalkene 4a and 4b to methyl acrylate. The esters were then hydrolysed to give the γ-nitroalkanoic and γ-nitroalkenoic acids 6a and 6b (Scheme 2):

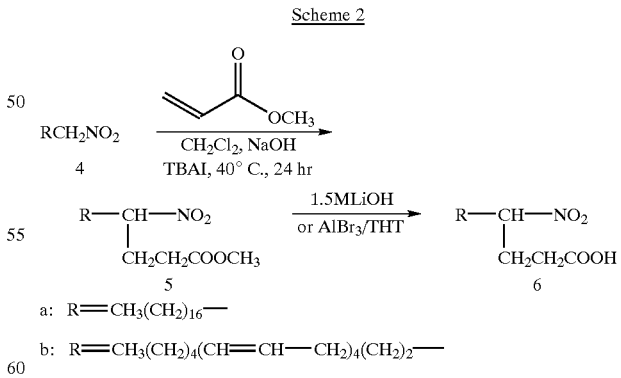

A published method [16] for the synthesis of short chain γ-nitroalkanoic acid esters was investigated for synthesis of the long chain acid ester 5a. The nitroalkane 4a was treated with methyl acrylate in a two phase system of water and dichloromethane in the presence of sodium hydroxide at room temperature for 24 hours. No reaction occurred under these conditions and a modification was then made where tetrabutylammonium iodide (TBAI), a phase transfer catalyst, was introduced into the reaction to improve the solubility of the base in the organic phase. With this change, a small amount of the expected product was detected by $^1$H NMR analysis of the crude reaction residue. The yield of γ-nitroalkanoic acid ester 5a was further improved (reaching 69% yield) by increasing the relative amount to 3:1 (for methyl acrylate:nitroalkane) and by increasing the reaction temperature to 50° C. The γ-nitroalkanoic acid ester 5a was hydrolysed by treatment with either 1.5M lithium hydroxide in dimethoxyethane (DME) or aluminium tribromide in tetrahydrothiophene (THT) at room temperature to afford the γ-nitroalkanoic acid 6a in 98% yield. The unsaturated nitroalkenoic acid 6b was generated in similar yield using the same method, and both 6a and 6b were fully characterised.

(3) Synthesis of α, α-dipropanate Nitroalkane and Nitroalkene [8 a (Lx8) and 8 b (Lx9)]

Multiple Michael addition to primary nitroalkanes can lead to the production of multiply substituted nitroalkanes.[17] Based on this, the α, α-dipropanate ester nitroalkane and nitroalkene 7a and 7b were prepared by Michael addition of the nitroalkane and nitroalkene 4a and 4b to methyl acrylate in the presence of 1,8-diazabicyclo [5,4,0] undec-7-ene (DBU) as a strong base. The resulting diesters 7a and 7b were converted to the corresponding dicarboxylic acids 8a and 8b by lithium hydroxide hydrolysis (78–80% yield) (Scheme 3):

Scheme 3

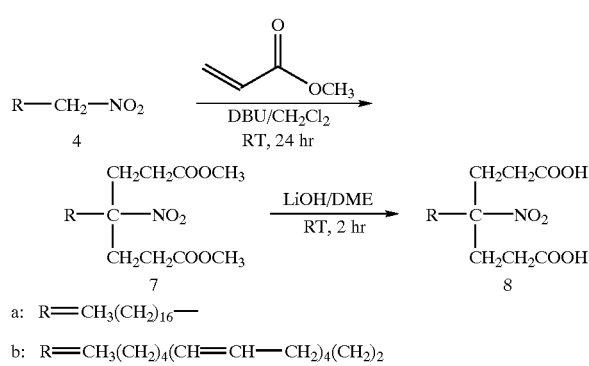

a: R═CH$_3$(CH$_2$)$_{16}$— b: R═CH$_3$(CH$_2$)$_4$(CH═CH—CH$_2$)$_4$(CH$_2$)$_2$ (4) Synthesis of α, β-unsaturated Nitroalkenes (11a and 11b)

The reaction scheme shown below (Scheme 4) was envisaged for generation of α, β-unsaturated nitroalkenes.

Scheme 4

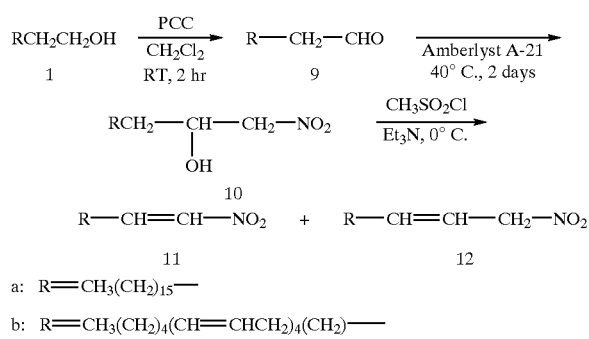

a: R═CH$_3$(CH$_2$)$_{15}$— b: R═CH$_3$(CH$_2$)$_4$(CH═CHCH$_2$)$_4$(CH$_2$)—

Fatty alcohol 1a was oxidised by pyridirium chlorochromate (PCC) in dichloromethane at room temperature to yield corresponding aldehyde 9a.[18] β-hydroxy nitroalkane can be efficiently obtained by nitroaldol reaction,[19] and in this case, the aldehyde 9a reacted with nitromethane in ether, with Amberlyst A-21 as a heterogeneous basic catalyst, generating the β-hydroxy nitroalkanes in 89% yield after purification. Dehydration of β-hydroxy nitroalkane 10a[20] was undertaken by mixing with 1 equivalent of methanesulfonyl chloride (CH$_3$SO$_2$Cl) and 4 equivalents of triethylamine in dry dichloromethane at 0° C. The $^1$H NMR spectrum of the residue indicated that the products were a mixture of conjugated and nonconjugated nitro compounds. In subsequent experiments, this reaction was monitored by TLC from 5 mins to 2.5 hours. The result showed that only the conjugated product 11a could be seen at 5 mins, and after 10 mins of reaction, the nonconjugated product 12a showed up and it became predominant after 2 hrs reaction. Although conjugated 11a and nonconjugated nitro compound 12a were distinguishable by $^1$H NMR and $^{13}$C NMR, and were separable by TLC, no pure samples of either compound were obtained by flash chromatography due to decomposition. A similar result was obtained for synthesis of conjugated compound 11b.

The variation in the product distribution (11a and 12a) during reaction may be explained on the basis of kinetic versus thermodynamic control. It is possible that the nonconjugated compound 12a is thermodynamically more stable, but the formation of the conjugated product 11a is kinetically favoured over that of the nonconjugated product 12a. However, once the reaction for conjugated compound formation reached a kinetic equilibrium, formation of the nonconjugated compound will become predominant because of its higher thermodynamic stability. However, further work is needed to elucidate this.

(5) Synthesis of α-nitro Acids 13a

A reported[21] one-pot method for synthesis of α-nitro acids was investigated which involved the use of magnesium methyl carbonate (MMC) as a carboxylating agent to introduce a carboxyl group at the α-carbon of a primary nitroalkane (Scheme 5):

Scheme 5

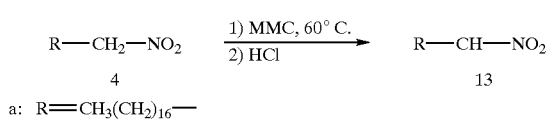

a: R═CH$_3$(CH$_2$)$_{16}$—

When 1-nitropropane was used as the starting material, the $^1$H NMR of the residue obtained after workup indicated formation of the corresponding α-nitro carboxylic acid. However, when the long chain nitroalkane 4a was used as the starting material, the expected α-nitro acid product 13a was not detected in the crude reaction mixture. The lack of reaction for stearyl nitrite may be attributed to poor solubility of stearyl nitrite in MMC solution.

Synthesis of the α-nitro acids 14a was subsequently investigated by conversion of the nitroalkane 4a of the corresponding α-nitro acid ester 14a by treatment with methyl chloroformate, followed by hydrolysis (Scheme 6):

Scheme 6

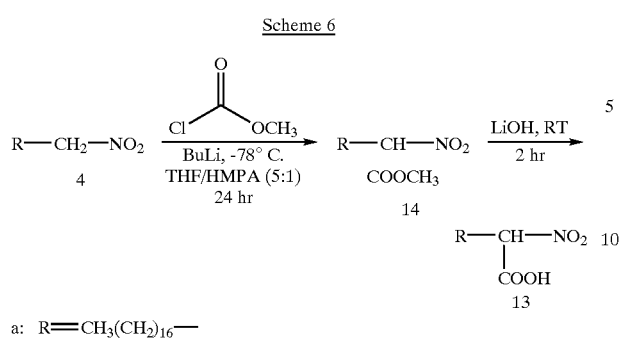

a: R═CH$_3$(CH$_2$)$_{16}$—

Using this scheme, the saturated nitro acid ester 13a was obtained in 25% yield from the corresponding nitroalkane 4a. Treatment of the ester 14a with lithium hydroxide in dimethoxyethane (DME) did not give rise to the desired acid 13a. The nitroalkane 4a, however, was isolated as the sole product of this reaction. This result can be explained as illustrated in Scheme 7.

Scheme 7

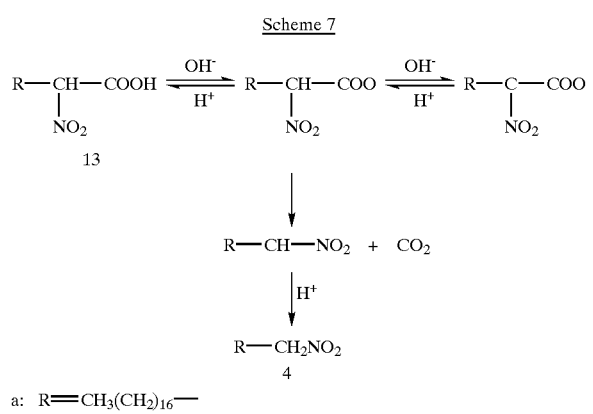

a: R═CH$_3$(CH$_2$)$_{16}$—

It has been reported[22] that free α-nitroacetic acid and its dianion salt are quite stable at room temperature, but that the monoanion salt decarboxylates rapidly at room temperature. The failure in generating the c-nitropropanoic acid is then likely due to decarboxylation of the monoanion in the basic reaction medium.

(6) Synthesis of Hydroxy and Hydroperoxy Derivatives of Compound 6b

Synthesis of hydroxy and hydroperoxy products of compound 6b was based on Scheme 8. Pure compound 17 was obtained in the yield of 32%. Compound 16 was relatively unstable, but the product with 90% purity was obtained by column chromatography at 0° C., and was used for investigation of its inhibitory effect on 15-LO catalysed oxidation of arachidonic acid.

Scheme 8

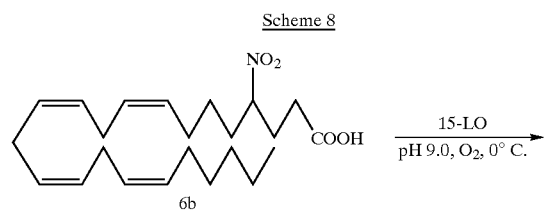

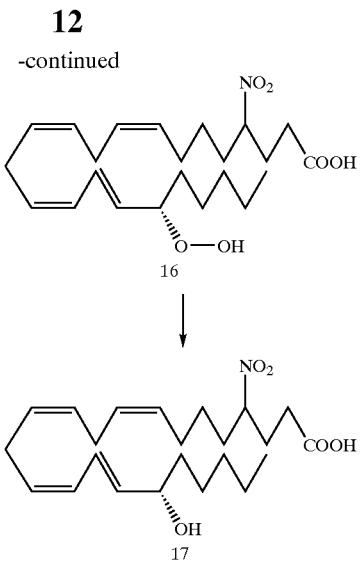

(7) Synthesis of Polyunsaturated Nitroalkanes and Nitro-substituted Fatty Acids.

The polyunsaturated fatty alcohols 1b–e and the saturated analogue, octadecanol 1a, are commercially available and were used as starting materials. Their treatment with triphenylphosphine and carbon tetrabromide according to the method of Hayashi et al.[23] afforded the corresponding bromides 2a–e. Short chain bromoalkanes react with silver nitrite to give nitroalkanes[24] but the bromides 2a–e were inert to such treatment. Instead, they were first treated with sodium iodide to give the iodides 3a–e, which were used without purification and converted to the nitroalkanes 4a–e, respectively.

Scheme 9

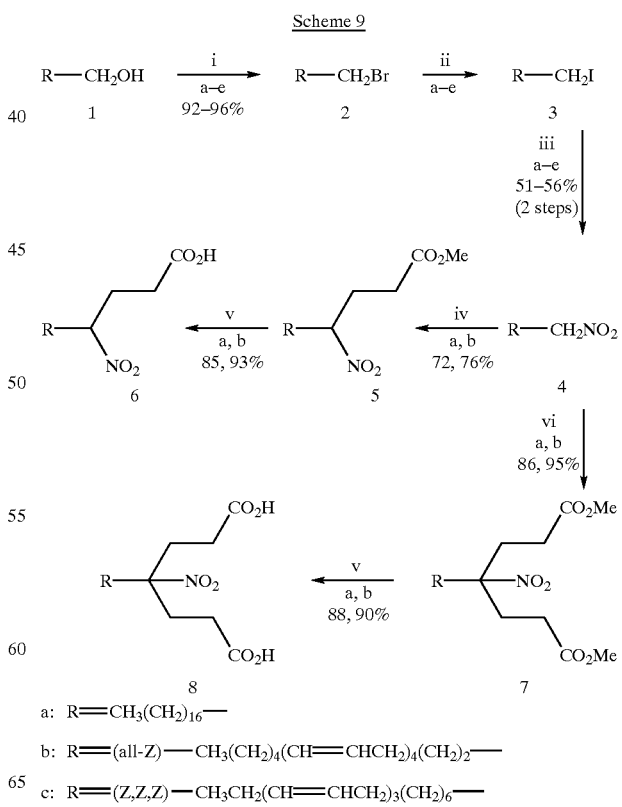

a: R═CH$_3$(CH$_2$)$_{16}$— b: R═(all-Z)—CH$_3$(CH$_2$)$_4$(CH═CHCH$_2$)$_4$(CH$_2$)$_2$— c: R═(Z,Z,Z)—CH$_3$CH$_2$(CH═CHCH$_2$)$_3$(CH$_2$)$_6$—

-continued d: R=(Z,Z,Z)—CH$_3$(CH$_2$)$_4$(CH=CHCH$_2$)$_3$(CH$_2$)$_3$— e: R=(all-Z)—CH$_3$CH$_2$(CH=CHCH$_2$)$_6$CH$_2$— i: PPh$_3$/CBr$_4$, CH$_2$Cl$_2$, r.t.
ii: NaI, dry acetone, r.t.
iii: AgNO$_2$, Et$_2$O, r.t.
iv: methyl acrylate, NaOH, Bu$_4$NI, CH$_2$Cl$_2$, reflux
v: LiOH, DME, r.t.
vi: methyl acrylate, DBU, CH$_2$Cl$_2$, r.t.

In order to prepare nitro-substituted fatty acids, a variety of reactions of nitroalkanes were investigated. Carboxylation using the method of Finkbeiner et al.[25] was examined. Accordingly reaction of 1-nitropropane with magnesium methyl carbonate afforded 2-nitrobutanoic acid, but 1-nitrooctadecane (4a) was recovered unchanged when treated under the same conditions. Apparently the aliphatic chain prevents reaction in the latter case. 1-Nitrooctadecane (4a) was treated with butyl lithium then methyl chloroformate[26] to give methyl 2-nitrononadecanoate. However, all attempts to hydrolyse this material to give 2-nitrononadecanoic acid failed, the reactions instead affording the nitroalkane 4a.

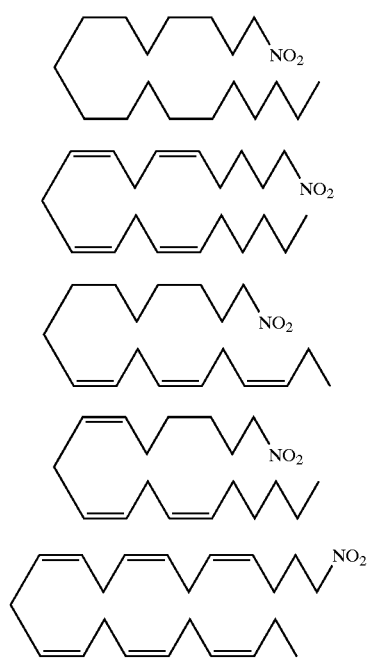

This product (ie nitroalkane 4a) may be attributed to rapid decarboxylation of the monoanion of 2-nitrononadecanoic acid, since the analogous process has been reported for 2-nitroacetic acid.[27] Given that this decarboxylation would be expected to affect the integrity of 2-nitrocarboxylic acids during physiological studies at near neutral pH, the synthesis of compounds of this type was not further pursued.

The nitroalkane 4a was inert when treated with butyl lithium and α-haloacetates, indicating that long chain 3-nitrocarboxylates could not be prepared using this approach. However, the nitroalkanes 4a,b reacted with sodium hydroxide and methyl acrylate[28] in the presence of tetrabutylammonium iodide[29] to give the γ-nitroesters 5a,b, which were hydrolysed using lithium hydroxide to afford the corresponding nitroacids 6a,b. Using 1,8-diazobicyclo [5.4.0] undec-7-ene (DBU) as the base, in place of sodium hydroxide, the nitroalkanes 4a,b reacted by sequential Michael additions with methyl acrylate to give the diesters 7a,b, which hydrolysed to the nitrodiacids 8a,b.

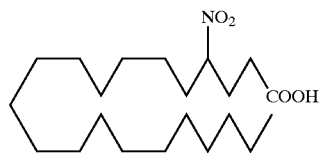

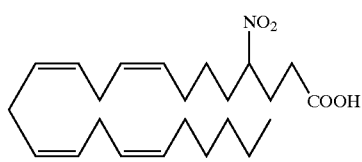

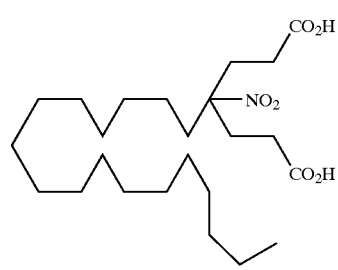

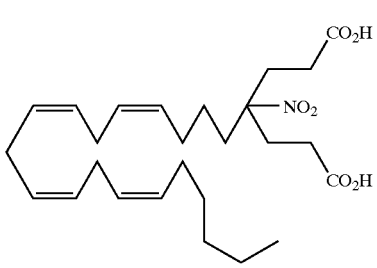

To obtain substituted nitroalkanes, the alcohols 1a,b were oxidised to the corresponding aldehydes 9a,b using pyridinium chlorochromate.[30] Henry condensation[31] of these compounds with nitromethane in the presence of Amberlyst A-21[32] afforded the 2-hydroxynitroalkanes 10a,b, which reacted with methanesulfonyl chloride and triethylamine[33] to give the corresponding α,β-unsaturated nitroalkanes. Unfortunately it was not possible to isolate pure samples of these analogues of α,β-unsaturated fatty acids, because they equilibrated with the corresponding β,γ-insaturated nitroalkanes and the mixtures of isomers decomposed on chromatography.

Scheme 10

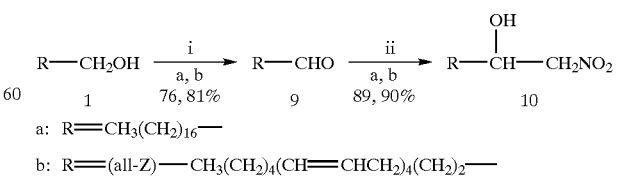

a: R=CH$_3$(CH$_2$)$_{16}$— b: R=(all-Z)—CH$_3$(CH$_2$)$_4$(CH=CHCH$_2$)$_4$(CH$_2$)$_2$— i: pyridinium chlorochromate, CH$_2$Cl$_2$, r.t.
ii: CH$_3$NO$_2$, Amberlyst A-21, Et$_2$O, reflux

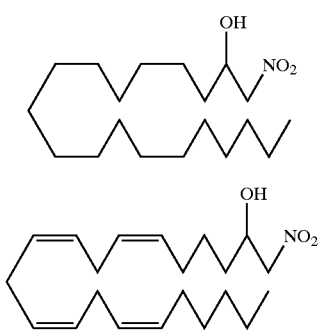

The reactions described above were carried out under nitrogen and in the dark. After purification the compounds were stored at −30° C. under nitrogen. By taking these precautions there were, no complications from isomerisation or autoxidation of the methylene-interrupted polyenes. Such reactions result in the formation of conjugated dienes and none of the compounds showed absorption at 234 nm which is characteristic of this structural feature.[34]

Experimental

Octadecan-1-ol (1a) was obtained from Aldrich Chemical Co. Arachidonyl alcohol (1b), linolenyl alcohol (1c), gamma linolenyl alcohol (1d) and docosahexaenyl alcohol 1e were purchased from Nu-Chek Prep. Inc. (Elysian, Minn., USA).

1-Bromooctadecane (2a); Typical Procedure

Octadecan-1-ol (1a) (520 mg, 1.92 mmol) and Ph$_3$P (550 mg, 2.10 mmol) were dissolved in CH$_2$Cl$_2$ (25 mL). The mixture was cooled in an ice bath and CBr$_4$ (630 mg, 1.90 mmol) was added with stirring. The mixture was allowed to warm to r.t. and was stirred overnight, then it was concentrated under a stream of N$_2$ and the residue was subjected to flash column chromatography on silica, eluting with hexane, to afford 1-bromooctadecane (2a) (605 mg, 96%) as a waxy solid; mp 26–28° C.

IR (KBr): ν=2920 (s), 2848 (s), 1468 (s), 1378 (w), 1254 (w), 1144 (m), 720 (m), 658 (s), cm$^{-1}$.

$^1$H NMR (CDCl$_3$, 300 MHz): δ=0.87 (t, 3H, J=6.7 Hz, C18-H$_3$), 1.25–1.32 [m, 30H, (C3–17)-H$_2$)], 1.82–1.85 (m, 2H, C2-H$_2$), 3.40 (t, 2H, J=6.8 Hz, C1-H$_2$).

$^{13}$C NMR (CDCl$_3$, 300 MHz): δ=14.7, 23.2, 28.7, 29.3, 29.9, 30.0, 30.1, 30.1(6), 30.2(3), 32.5, 33.4, 34.6.

MS (EI): m/z (%)=334 (M$^+$, 8), 332 (M$^+$, 10), 253 (25), 151 (27), 149 (28), 137 (67), 135 (69), 113 (19), 97 (30), 85 (50), 71 (70), 57 (100).

HRMS: m/z calcd for C$_{13}$H$_{37}$Br 334.2058 (M$^+$) and 332.2078 (M$^+$). Found: 334.2070 and 332.2086.

(all-Z)-1-Bromo-5,8,11,14-eicosatetraene (2b)

From arachidonyl alcohol (1b) (740 mg, 2.54 mmol), using the procedure described above for preparation of 1-bromooctadecane (2a), (all-Z)-1-bromo-5,8,11,14-eicosatetraene (2b) (826 mg, 93%) was obtained as a colourless oil.

IR (film): ν=3012 (s), 2958 (s), 2927 (s), 2856 (s), 1653 (m), 1456 (m), 1394 (m), 1251 (m), 1199 (w), 1041 (m), 915 (w), 807 (w), 715 (s) cm$^{-1}$.

$^1$H NMR (CDCl$_3$, 300 MHz): δ=0.89 (t, 3H, J=6.8 Hz, C20-H$_3$), 1.29–1.38 (m, 6H, C17-H$_2$, C18-H$_2$, C19-H$_2$), 1.47–1.56 (m, 2H, C3-H$_2$), 1.83–1.93 (m, 2H, C2-H$_2$), 2.03–2.14 (m, 4H, C4-H$_2$, C16-H$_2$), 2.80–2.83 (m, 6H, C7-H$_2$, C10-H$_2$, C13-H$_2$), 3.42 (t, 2H, J=6.8 Hz, C1-H$_2$), 5.30–5.41 (m, 8H, C5-H, C6-H, C8-H, C9-H, C11-H, C12-H, C14-H, C15-H).

$^{13}$C NMR (CDCl$_3$, 300 MHz): δ=14.7, 23.2, 26.2, 26.9, 27.8, 28.7, 29.9, 32.1, 32.9, 34.3, 128.1, 128.4, 128.7 (2C), 129.0, 129.1, 129.9, 131.1.

MS (EI): m/z (%)=354 (M$^-$, 5), 352 (M$^+$, 6), 283 (8), 281 (8), 256 (15), 254 (15), 216 (25), 214 (25), 150 (34), 119 (29), 105 (36), 93 (53), 91 (56), 79 (100), 67 (75).

HRMS: m/z calcd for C$_{20}$H$_{33}$Br 354.1745 (M$^+$) and 352.1766 (M$^+$). Found: 354.1748 and 352.1772.

Anal. Calcd for C$_{20}$H$_{33}$Br: C, 67.98; H, 9.41. Found: C, 68.05; H, 9.28.

(Z,Z,Z)-1-Bromo-9,12,15-octadecatriene (2c)

From linolenyl alcohol (1c) (102 mg, 0.39 mmol), using the procedure described above for preparation of 1-bromooctadecane (2a), (Z,Z,Z)-1-bromo-9,12,15-octadecatriene (2c) (118 mg, 93%) was obtained as a colourless oil.

IR (film): ν=3001 (s), 2960 (s), 2920 (s), 2850 (s), 1460 (m), 1430 (m), 1395 (w), 1270 (w), 720 (w) cm$^{-1}$.

$^1$H NMR (CDCl$_3$, 300 MHz): δ=0.98 (t, 3H, J=7.5 Hz, C18-H$_3$), 1.30–1.45 (m, 10H, C3-H$_2$, C4-H$_2$, C5-H$_2$, C6-H$_2$, C7-H$_2$), 1.81–1.88 (m, 2H, C2-H$_2$), 2.03–2.11 (m, 4H, C8-H$_2$, C17-H$_2$), 2.80–2.83 (m, 4H, C11-H$_2$, C14-H$_2$), 3.41 (t, 2H, J=6.8 Hz, C1-H$_2$), 5.30–5.42 (m, 6H, C9-H, C10-H, C12-H, C13-H, C15-H, C16-H).

$^{13}$C NMR (CDCl$_3$, 300 MHz): δ=14.9, 21.1, 26.1, 26.2, 27.8, 28.7, 29.3, 29.8, 29.9, 30.2, 33.4, 34.6, 127.7, 128.3, 128.8 (2C), 130.8, 132.5.

MS (EI): m/z (%)=328 (M$^+$, 14), 326 (M$^+$, 14), 272 (42), 270 (41), 149 (13), 135 (28), 121 (33), 108 (92), 95 (53), 79 (100), 67 (72), 55 (59).

Anal. Calcd for C$_{13}$H$_{31}$Br: C, 66.05; H, 9.54. Found: C, 65.82; H, 9.32.

(Z,Z,Z)-1-Bromo-6,9,12-octadecatriene (2d)

From gamma linolenyl alcohol (1d) (143 mg, 0.54 mmol), using the procedure described above for preparation of 1-bromooctadecane (2a), (Z,Z,Z)-1-bromo-6,9,12-octadecatriene (2d) (170 mg, 96%) was obtained as a colourless oil.

IR (film): ν=3002 (s), 2950 (s), 2920 (s), 2850 (s), 1460 (s), 1378 (w), 1260 (w), 715 (m), 648 (m) cm$^{-1}$.

$^1$H NMR (CDCl$_3$, 300 MHz): δ=0.89 (t, 3H, J=6.8 Hz, C18-H$_3$), 1.29–1.45 (m, 10H, C3-H$_2$, C4-H$_2$, C15-H$_2$, C16-H$_2$, C17-H$_2$), 1.82–1.91 (m, 2H, C2-H$_2$), 2.02–2.17 (m, 4H, C5-H$_2$, C14-H$_2$), 2.79–2.83 (m, 4H, C8-H$_2$, C11-H$_2$), 3.40 (t, 2H, J=6.7 Hz, C1-H$_2$), 5.30–5.41 (m, 6H, C6-H, C7-H, C9-H, C10-H, C12-H, C13-H).

$^{13}$C NMR (CDCl$_3$, 300 MHz): δ=14.7, 23.2, 26.2, 27.6, 27.8, 28.4, 29.3, 29.9, 32.1, 33.3, 34.5, 128.2, 128.6(5), 128.7(1), 129.0, 130.3, 131.0.

MS (EI): m/z (%)=328 (M$^+$, 10), 326 (M$^+$, 8), 230 (49), 228 (50), 150 (66), 135 (15), 121 (25), 107 (32), 93 (59), 79 (100), 67 (95), 55 (64).

HRMS: m/z calcd for C$_{18}$H$_{31}$Br 328.1589 (M$^+$) and 326.1609 (M$^+$). Found: 328.1592 and 326.1611.

(all-Z-1-Bromo-4,7,10,13,16,19-docosahexaene (2e)

From docosahexaenyl alcohol 1e (201 mg, 0.64 mmol), using the procedure described above for preparation of 1-bromooctadecane (2a), (all-Z)-1-bromo-4,7,10,13,16,19-docosahexaene (2e) (221 mg, 92%) was obtained as a colourless oil.

IR (film): ν=3008 (s), 2960 (s), 2928 (s), 2868 (s), 1650 (m), 1434 (s), 1392 (s), 1348 (w), 1322 (w), 1266 (s), 1244 (s), 1068 (m), 1044 (m), 928 (m), 714 (s) cm$^{-1}$.

$^1$H NMR (CDCl$_3$, 300 MHz): δ=0.98 (t, 3H, J=7.5 Hz, C22-H$_3$), 1.85–2.30 (6H, C2H$_2$, C3-H$_2$, C21-H$_2$), 2.80–2.90 (m, 10H, C6-H$_2$, C9-H$_2$, C12-H$_2$, C15-H$_2$, C18-H$_2$), 3.42 (t, 2H, J=6.6 Hz, C1-H$_2$), 5.31–5.45 (m, 12H, C4-H, C5-H, C7-H, C8-H, C10-H, C11-H, C13-H, C14-H, C16-H, C17-H, C19-H, C20-H).

$^{13}$C NMR (CDCl$_3$, 300 MHz): δ=14.4, 20.5, 25.5, 25.6, 32.5 33.2, 127.0, 127.8(5), 127.9(4), 128.0(6), 128.1(1) (2C), 128.1(8) (2C), 128.2(4), 128.6, 129.5, 132.0.

MS (EI): m/z (%)=378 (M+, 10), 376 (M+, 10), 349 (20), 347 (20), 309 (46), 307 (53), 244 (75), 242 (74), 227 (49), 202 (30), 200 (30), 173 (12), 133 (34), 119 (45), 108 (50), 91 (65), 79 (100), 67 (66).

HRMS: m/z calcd for $C_{22}H_{33}Br$ 378.1745 (M+) and 376.1766 (M+). Found: 378.1742 and 376.1760.

1-Nitrooctadecane (4a); Typical Procedure

To a solution of 1-bromooctadecane (2a) (480 mg, 1.44 mmol) in dry acetone (25 mL) at r.t. was added NaI (430 mg 2.87 mmol). The mixture was stirred at r.t. overnight, then the solvent was removed in vacuo. The residue was mixed with 25 mL of sat. aq sodium bisulfite and the mixture was extracted with $Et_2O$ (3×25 mL). The combined extracts were dried ($Na_2SO_4$) and the solvent was removed in vacuo. The residue (502 mg) was dissolved in anhyd $Et_2O$ and $AgNO_2$ (406 mg, 2.64 mmol) was added. After 3 days of stirring, the mixture was filtered through a bed of celite and the filtrate was evaporated under a stream of dry $N_2$. The residue was subjected to flash column chromatography on silica ($Et_2O$/hexane, 5/95) to give crude iodide 3a (97 mg) and 1-nitrooctadecane (4a) (220 mg, 51%) as a white solid; mp41–42° C.

IR (film): ν=2954 (s), 2919 (s), 2850 (s), 1563 (s), 1470 (m), 1385 (w), 1147 (w), 742 (w), 720 (m), 630 (w) $cm^{-1}$.

$^1$H NMR ($CDCl_3$, 300 MHz): δ=0.88 (t, 3H, J=6.6 Hz, C18-$H_3$), 1.25–1.34 [m, 30H, (C3–C17)-$H_2$], 1.96–2.05 (m, 2H, C2-$H_2$), 4.38 (t, 2H, J=7.1 Hz, C1-$H_2$).

$^{13}$C NMR ($CDCl_3$, 300 Mz): δ=14.7, 23.3, 26.7, 28.0, 29.4, 29.8, 29.9, 30.0, 30.1, 30.2, 30.3, 32.5, 76.3.

MS (EI): m/z (%)=299 (M+, <1), 282 (4), 264 (20), 252 (7), 238 (7), 224 (7), 210 (5), 196 (4), 154 (5), 139 (7), 125 (20), 111 (40), 97(74), 83 (87), 69 (95), 57 (100), 55 (96).

Anal. Calcd for $C_{18}H_{37}NO_2$: C, 72.19; H, 12.45; N, 4.68. Found: C, 72.33; H, 12.77; N, 4.57.

(all-Z)-1-Nitro-5,8,11,14-eicosatetraene (4b)

According to the procedure described above for preparation of 1-nitrooctadecane (4a), (all-Z)-1-bromo-5,8,11,14-eicosatetraene (2b) (782 mg, 2.21 mmol) gave crude iodide (3b) (71 mg) and (all-Z)-1-nitro-5,8,11,14-eicosatetraene (4b) (397 mg, 56%) as a colourless oil.

IR (film): ν=3013 (s), 2957 (s), 2928 (s), 2857 (s), 1648 (w), 1555 (s), 1457 (m), 1435 (m), 1381 (s), 1267 (w), 1106 (w), 1047 (w), 969 (w), 914 (w), 716 (m) $cm^{-1}$.

$^1$H NMR ($CDCl_3$, 300 MHz): δ=0.89 (t, 3H, J=6.8 Hz, C20-$H_3$), 1.20–1.51 (m, 8H, C3-$C_2$, C17-$H_2$, C18-$H_2$, C19-$H_2$), 1.99–2.16 (m, 6H, C2-$H_2$, C4-$H_2$, C16-$H_2$), 2.79–2.86 (m, 6H, C7-$H_2$, C10-$H_2$, C13-$H_2$), 4.39 (t, 2H, J=7.0 Hz, C1-$H_2$), 5.32–5.43 (m, 8H, C5-H, C6-H, C8-H, C9-H, C11-H, C12-H, C14-H, C15-H).

$^{13}$C NMR ($CDCl_3$, 300 MHz): δ=14.6, 23.1, 26.2, 26.7, 26.9, 27.5, 27.8 29.9, 32.1, 76.1, 128.1, 128.4, 128.5, 128.9, 129.2 (2C), 129.6, 131.1.

MS (EI): m/z (%)=319 (M+, 6), 302 (14), 220 (27), 205 (15), 190 (11), 181 (24), 177 (20), 164 (25), 150 (41), 119 (48), 105 (63), 91 (90), 79 (100), 67 (97), 55 (77).

Anal. Calcd for $C_{20}H_{33}NO_2$: C, 75.19; H, 10.41; N, 4.38. Found: C, 74.92; H, 10.40; N, 4.43.

(Z,Z,Z)-1-Nitro-9,12,15-octadecatriene (4c)

Following the procedure described above for preparation of 1-nitrooctadecane (4a), (Z,Z,Z)-1-bromo-9,12,15-octadecatriene (2c) (79 mg, 0.24 mmol) gave crude iodide 3c (12 mg) and (Z,Z,Z)-1-nitro-9,12,15-octadecatriene (4c) (37 mg, 53%) as a colourless oil.

IR (film): ν=3011 (s), 2962 (s), 2929 (s), 2856 (s), 1652 (w), 1554 (s), 1463 (m), 1435 (m), 1383 (m), 1268 (w), 1148 (w), 1069 (w), 968 (w), 912 (w), 724 (m), 614 (w) $cm^{-1}$.

$^1$H NMR ($CDCl_3$, 300 MHz): δ=0.98 (t, 3H, J=7.5 Hz, C18-$H_3$), 1.25–1.33 (m, 10H, C3-$H_2$, C4-$H_2$, C5-$H_2$, C6-$H_2$, C7-$H_2$), 1.97–2.06 (m, 6H, C2-$H_2$, C8-$H_2$C17-$H_2$), 2.79–2.81 (m, 4H, C11-$H_2$, C14-$H_2$), 4.37 (t, 2H, J=7.1 Hz, C1-$H_2$), 5.36–5.40 (m, 6H, C9-H, C10-H, C12-H, C13H, C15-H, C16-H).

$^{13}$C NMR ($CDCl_3$, 300 MHz): δ=14.9, 21.1, 26.1, 26.2, 26.8, 27.7, 28.0, 29.4, 29.6, 29.7, 30.1, 76.3, 127.7, 128.4, 128.8, 128.9, 130.7, 132.5.

MS (EI): m/z (%)=293 (M+, 24), 276 (14), 264 (5), 246 (5), 237 (32), 224 (17), 135 (26), 121 (35), 108 (63), 95 (84), 93 (75), 91 (69), 79 (100), 67 (95).

Anal. Calcd for $C_{18}H_{31}NO_2$: C, 73.67; H, 10.65; N, 4.77. Found: C, 73.69; H, 10.57; N, 4.85.

(Z,Z,Z)-1-Nitro-6,9,12-octadecatriene (4d)

Following the procedure described above for preparation of 1-nitrooctadecane (4a), (Z,Z,Z)-1-bromo-6,9,12-octadecatriene (2d) (122 mg, 0.37 mmol) gave crude iodide 3d (15 mg) and (Z,Z,Z)-1-nitro4,9,12-octadecatriene (4d) (56 mg, 51%) as a colourless oil.

IR (film): ν=3012 (s), 2956 (s), 2928 (s), 2858 (s), 1652 (m), 1555 (s), 1464 (s), 1435 (s), 1382 (s), 1266 (m), 1159 (w), 1067 (w), 1040 (w), 970 (w), 914 (w), 720 (s), 614 (w) $cm^{-1}$.

$^1$H NMR ($CDCl_3$, 300 MHz): δ=0.88 (t, 3H, J=7.1 Hz, C18-$H_3$), 1.29–1.43 (m, 10H, C3-$H_2$, C4-$H_2$, C15-$H_2$, C16-$H_2$, C17-$H_2$), 2.01–2.08 (m, 6H, C2-$H_2$C5-$H_2$), C14-$H_2$), 2.78–2.82 (m, 4H, C8-$H_2$, C11-$H_2$), 4.38 (t, 2H, J=7.1 Hz, C1-$H_2$), 5.34–5.40 (m, 6H, C6-H, C7-H, C9-H, C10-H, C12-H, C13-H).

$^{13}$C NMR ($CDCl_3$, 300 MHz): δ=14.7, 23.2, 26.2, 26.4, 27.4, 27.8, 27.9, 29.4, 29.9, 32.1, 76.2, 128.1, 128.5, 129.0 (2C), 129.9, 131.0.

MS (EI): m/z (%)=293 (M+, 31), 276 (25), 258 (12), 246 (4), 222 (7), 195 (72), 150 (36), 137 (18), 105 (25), 91 (84), 81 (80), 80 (79), 79 (100), 67 (82), 55 (60).

Anal. Calcd for $C_{18}H_{31}NO_2$: C, 73.67; H, 10.65; N, 4.77. Found: C, 73.56; H, 10.56; N, 4.74.

(all-Z)-1-Nitro4,7,10,13,16,19-docosahexaene (4e)

Following the procedure described above for preparation of 1-nitrooctadecane (4a), (all-Z)-1-bromo4,7,10,13,16,19-docosahexaene (2e) (165 mg, 0.44 mmol) gave crude iodide 3e (27 mg) and (all-Z)-1-nitro4,7,10,13,16,19-docosahexaene (4e) (80 mg, 53%) as a colourless oil.

IR (film): ν=3014 (s), 2962 (s), 2926 (s), 2873 (s), 2854 (s), 1653 (m), 1554 (s), 1434 (s), 1381 (s), 1352 (m), 1267 (m), 1069 (w), 917 (w), 712 (s), 611 (w) $cm^{-1}$.

$^1$H NMR ($CDCl_3$, 300 MHz): δ=0.98 (t, 3H, J=7.6 Hz, C22-$H_3$), 2.05–2.23 (m, 6H, C2-$H_2$, C3-$H_2$, C21-$H_2$), 2.78–2.85 (m, 10H, C6-$H_2$, C9-$H_2$, C12-$H_2$, C15-$H_2$, C18-$H_2$), 4.38 (t, 2H, J=6.7 Hz, C1-$H_2$), 5.31–5.47 (m, 12H, C4-H, C5-H, C7-H, C8-H, C10-H, C11-H, C13-H, C14-H, C16-H, C17-H, C19-H, C20-H).

$^{13}$C NMR ($CDCl_3$, 300 MHz): δ=14.8, 21,1, 24.4, 26.1, 26.2, 27.7, 75.4, 127.6, 128.3, 128.4, 128.5(5), 128.6(0), 128.9 (3C), 129.1, 129.2, 130.9, 132.6.

MS (EI): m/z (%)=343 (M+, 10), 326 (59), 314 (21), 274 (44), 215 (55), 207 (42), 167 (16), 145 (18), 131 (16), 119 (36), 105 (48), 91 (77), 79 (100), 67 (78), 55 (42).

Anal. Calcd for $C_{22}H_{33}NO_2$: C, 76.92; H, 9.68; N, 4.08. Found: C, 76.52; H, 9.87; N, 4.26.

Methyl 4-Nitroheneicosanoate (5a); Typical Procedure

A solution of NaOH (136 mg, 3.4 mmol) and $Bu_4NI$ (158 mg 0.43 mmol) in water (10 mL) was added to a solution of 1-nitrooctadecane (4a) (510 mg, 1.70 mmol) and methyl acrylate (442 mg, 5.13 mmol) in $CH_2Cl_2$ (10 mL) at r.t. The mixture was stirred and heated at reflux for 24 h, then it was cooled and the layers were separated. The organic phase was washed with water (2×25 mL) and dried with $Na_2SO_4$. The solvent was evaporated and the residue was subjected to flash column chromatography on silica (Et$_2$O/hexane, 5/95), giving methyl 4-nitroheneicosanoate (5a) (498 mg, 76%) as a waxy solid.

IR (Nujol): ν=2924 (s), 2853 (s), 1744 (s), 1554 (s), 1466 (m), 1439 (m), 1367 (m), 1201 (m), 1175 (m), 1120 (m), 829 (w), 722 (w) cm$^{-1}$.

$^1$H NMR (CDCl$_3$, 300 MHz): δ=0.87 (t, 3H, J=6.7 Hz, C21-H$_3$), 1.19–1.25 [m, 30H, (C6–C20)-H$_2$], 1.69–1.78 (m, 1H), 1.92–2.30 (m,3H), 2.32–2.40 (m, 2H, C2-H$_2$), 3.69 (s, 3H, OCH$_3$), 4.50–4.59 (m, 1H, C4-H).

$^{13}$C NMR (CDCl$_3$, 300 MHz): δ=14.7, 23.3, 26.2, 29.2, 29.5, 29.8, 29.9, 30.0, 30.1, 30.2, 30.3, 30.5, 32.5, 34.5, 52.5, 88.4, 173.0.

MS (EI): m/z (%)=386 [(M+1)$^+$, 25], 368 (12), 354 (18), 339 (20), 305 (24), 287 (28), 263 (18), 221 (15), 193 (10), 179 (15), 165 (21), 151 (26), 137 (31), 123 (36), 111 (52), 97 (76), 83 (86), 69 (88), 55 (100).

HRMS: m/z calcd for C$_{22}$H$_{44}$NO$_4$ 386.3270 (M+H)$^+$. Found 386.3275.

Anal. Calcd for C$_{22}$H$_{43}$NO$_4$: C, 68.53; H, 11.24; N, 3.63. Found: C, 68.39; H, 11.53; N, 3.50.

Methyl (all-Z)-4-Nitrotricosa-8,11,14,17-tetraenoate (5b)

Following the procedure described above for preparation of methyl 4-nitroheneicosanoate (5a), (all-Z)-1-nitro-5,8,11,14-eicosatetraene (4b) (650 mg, 2.03 mmol) gave methyl (all-Z)-4-nitrotricosa-8,11,14,17-tetraenoate (5b) (594 mg, 72%) as a colourless oil.

IR (film): ν=3065 (w), 3013 (m), 2956 (s), 2930 (s), 2859 (m), 1737(s), 1552 (s), 1439 (m), 1363 (w), 1267 (w), 1263 (w), 1259 (w), 1204 (m), 1178 (m), 981 (w) cm$^{-1}$.

$^1$H NMR (CDCl$_3$, 300 MHz): δ=0.88 (t, 3H, J=6.8 Hz, C23-H$_3$), 1.24–1.45 (m, 8H, C6-H$_2$, C20-H$_2$, C21-H$_2$, C22-H$_2$), 1.70–1.81 (m, 1H), 1.91–2.27 (m, 7H), 2.32–2.40 (m, 2H, C2-H$_2$), 2.73–2.83 (m, 6H, C10-H$_2$, C13-H$_2$, C16-H$_2$), 3.68 (s, 3H, OCH$_3$), 4.51–4.58 (m, 1H, C4-H), 5.29–5.44 (m, 8H, C8-H, C9-H, C11-H, C12-H, C14-H, C15-H, C17-H, C18-H).

$^{13}$C NMR (CDCl$_3$, 300 MHz): δ=14.7, 23.1, 26.1, 26.2, 26.9, 27.8, 29.2, 29.9, 30.3, 30.5, 32.1, 33.9, 52.5, 88.2, 128.1, 128.4, 128.6, 128.9, 129.2 (2C), 129.6, 131.1, 172.9.

MS (EI): m/z (%)=405 (M$^+$, 7), 374 (8), 359 (5), 327 (4), 307 (15), 294 (6), 267 (4), 229 (5), 215 (10), 190 (13), 177 (27), 164 (33), 150 (36), 147 (24), 131 (35), 119 (43), 105 (54), 91 (70), 79 (93), 67 (100), 55 (56).

HRMS: m/z calcd for C$_{24}$H$_{39}$NO$_4$ 405.2879 (M$^+$). Found 405.2870.

Anal. Calcd for C$_{24}$H$_{39}$NO$_4$: C, 71.08; H, 9.69; N, 3.45. Found: C, 71.50; H, 10.03; N, 3.34.

4-Nitroheneicosanoic Acid (6a); Typical Procedure

Methyl 4-nitroheneicosanoate (5a) (147 mg, 0.38 mmol) was dissolved in 1,2-dimethoxyethane (DME) (2 mL) and sat. aq LiOH solution (2 mL) was added. The mixture was left for 24 h, then it was acidified with dilute HCl (10%, 10 mL) and the mixture was extracted with EtOAc (2×10 mL). The extracts were concentrated under a stream of dry N$_2$ and the residue was subjected to flash column chromatography on silica (Et$_2$O/hexane, 100/20, then Et$_2$O/hexane/HOAc, 60/40/1) to afford 4-nitroheneicosanoic acid (6a) (121 mg, 85%) as a white solid; mp 55–56° C.

IR (KBr): ν=3500–2600 (br), 2955 (m), 2919 (s), 2849 (s), 1698 (s), 1615 (w), 1543 (s), 1467 (m), 1445 (m), 1413 (w), 1360 (w), 1334 (w), 1266 (w), 923 (w), 827 (w), 723 (w), 612 (w) cm$^{-1}$.

$^1$H NMR (CDCl$_3$, 300 MHz): δ=0.87 (t, 3H, J=7.1 Hz, C21-H$_3$), 1.20–1.28 [m, 30H, (C6–C20)-H$_2$], 1.69–1.78 (m, 1), 1.98–2.30 (m, 3H), 2.39–2.48 (m, 2H, C2-H$_2$), 4.53–4.60 (m, 1H, C4-H).

$^{13}$C NMR (CDCl$_3$, 300 MHz): δ=14.7, 23.3, 26.2, 28.8, 29.5, 29.8, 29.9, 30.0, 30.1, 30.2(6), 30.3(3), 32.5, 34.4, 88.2, 177.5.

MS (CI): m/z=389.3 (M+NH$_4$)$^+$.

MS (EI): m/z (%)=354 [(M−OH)$^+$, 2], 323 (19), 321 (19), 305 (17), 287 (14), 263 (12), 236 (5), 221 (9), 193 (10), 179 (15), 165 (15), 151 (17), 137 (20), 125 (25), 110 (73), 97 (100), 83 (64), 69 (64), 55 (73).

HRMS: m/z calcd for C$_{21}$H$_{40}$NO$_3$ 354.3008 (M−OH)$^+$. Found 354.3006.

Anal. Calcd for C$_{21}$H$_{41}$NO$_4$: C, 67.88; H, 11.12; N, 3.77. Found: C, 67.58; H, 11.08; N, 3.81.

(all-Z)-4-Nitrotricosa-8,11,14,17-tetraenoic Acid (6b)

Following the procedure described above for preparation of 4-nitroheneicosanoic acid (6a), methyl (all-Z)-4-nitrotricosa-8,11,14,17-tetraenoate (5b) (230 mg, 0.57 mmol) gave (all-Z)-4-nitrotricosa-8,11,14,17-tetraenoic acid (6b) (207 mg, 93%) as a colourless oil.

IR (film): ν=3611–3317 (br), 3013 (m), 2922 (s), 2852 (m), 2693 (m), 2361 (w), 1714 (s), 1551 (s), 1441 (s), 1379 (m), 1360 (m), 1270 (m), 1071 (m), 969 (w), 916 (m), 844 (m), 824 (w), 720 (m) cm$^{-1}$.

$^1$H NMR (CDCl$_3$, 300 MHz): δ=0.89 (t, 3H, J=7.1 Hz, C23-H$_3$), 1.27–1.44 (m, 8H, C6-H$_2$, C20-H$_2$, C21-H$_2$), 1.70–1.82 (m, 1H), 1.93–2.27 (m, 7H), 2.40–2.48 (m, 2H, C2-H$_2$), 2.78–2.86 (m, 6H, C10-H$_2$, C13-H$_2$, C16-H$_2$), 4.56–4.59 (m, 1H, C$_4$-H), 5.30–5.43 (m, 8H, C8-H, C9-H, C11-H, C12-H, C14-H, C15-H, C17-H, C18-H).

$^{13}$C NMR (CDCl$_3$, 300 MHz): δ=14.7, 23.1, 26.1, 26.2, 26.9, 27.8, 28.9, 29.9, 30.2, 32.1, 33.9, 88.1, 128.1, 128.4, 128.5, 128.9, 129.1, 129.2, 129.7, 131.1, 176.8.

MS (EI): m/z (%)=391 (M$^+$, 8), 345 (8), 320 (4), 293 (13), 280 (8), 253 (10), 203 (15), 190 (25), 177 (28), 164 (42), 10 (46), 131 (34), 110 (100), 91 (72), 79 (93), 67 (97).

HRMS: m/z calcd for C$_{23}$H$_{37}$NO$_4$ 391.2723 (M$^+$). Found 391.2725.

Anal. Calcd for C$_{23}$H$_{37}$NO$_4$: C, 70.55; H, 9.52; N, 3.58. Found: C, 70.29; H, 9.86; N, 3.43.

Dimethyl 3-Heptadecyl-3-nitropertane-1,5-dicarboxylate (7a); Typical Procedure

A solution containing 1-nitrooctadecane (4a) (50 mg, 0.17 mmol), methyl acrylate (88 mg, 1.02 mmol) and DBU (13 mg 0.085 mmol) in CH$_2$Cl$_2$ (2 mL) was kept at r.t. for 24 h, then it was acidified with HCl (10%, 5 mL) and the mixture was extracted with CH$_2$Cl$_2$ (2×10 mL). The combined extracts were dried with Na$_2$SO$_4$ and concentrated, and the residue was subjected to flash column chromatography on silica (EtOAc/petroleum spirit, 15/85), to give dimethyl 3-heptadecyl-3-nitropentane-1,5-dicarboxylate (7a) (76 mg, 95%) as a colourless oil.

IR (film): ν=2954 (m), 2914 (s), 2849 (s), 1744 (s), 1732 (s), 1537 (s), 1470 (s), 1458 (s), 1439 (s), 1378 (s), 1355 (s), 1319 (s), 1298 (s), 1203 (s), 1180 (s), 1129 (s), 1110 (m), 1071 (m), 1022 (s), 986 (s), 894 (s), 864 (m), 842 (s), 826 (s), 807 (m), 788 (m), 717 (s), 705 (m) cm$^{-1}$.

$^1$H NMR (CDCl$_3$, 300 MHz): δ=0.88 (t, 3H, J=6.8 Hz, C17'-H$_3$), 1.16–1.25[m, 30H, (C2'–C16')-H$_2$], 1.85–1.91 (m, 2H, C1'-H$_2$), 2.23–2.28 (m, 8H, C2-H$_2$, C3-H$_2$, C5-H$_2$, C6-H$_2$), 3.69 (s, 6H, OCH$_3$).

$^{13}$C NMR (CDCl$_3$, 300 MHz): δ=14.7, 23.3, 24.1, 29.1, 29.8, 29.9, 30.0(5), 30.1(2), 30.3, 30.9, 32.5, 36.0, 52.5, 93.3, 173.0.

MS (CI): m/z=489 (M+NH$_4$)$^+$.

MS (EI): m/z (%)=440 [(M−OCH$_3$)$^+$,9], 425 (28), 393 (100), 392 (83), 364 (19), 333 (18), 305 (14), 194 (11), 168 (42), 138 (82), 109 (35), 81 (53).

HRMS: m/z calcd for C$_{25}$H$_{46}$NO$_5$ 440.3376 (M−OCH$_3$)$^+$. Found 440.3379.

Anal. Calcd for $C_{26}H_{49}NO_6$: C, 66.21; H, 10.47; N, 2.97. Found: C, 66.63; H, 10.91; N, 2.71.

Dimethyl 3-[(all-Z)-Nonadeca-4,7,10,13-tetraenyl]-3-nitropentane-1,5-dicarboxylate (7b)

Following the procedure described above for synthesis of dimethyl 3-heptadecyl-3-nitropentane-1,5-dicarboxylate (7a), (all-Z)-1-nitro-5,8,11,14-eicosatetraene (4b) (96 mg, 0.30 mmol) gave dimethyl 3-[(all-Z)-nonadeca-4,7,10,13-tetraenyl]-3-nitropentane-1,5-dicarboxylate (7b) (127 mg, 86%) as a colourless oil.

IR (film): ν=3012 (m), 2955 (m), 2929 (m), 2857 (m), 1742 (s), 1540 (s), 1438 (m), 1379 (w), 1351 (m), 1321 (m), 1260 (m), 1200 (m), 1176 (m), 990 (w), 721 (w) cm$^{-1}$.

$^1$H NMR (CDCl$_3$, 300 MHz): δ=0.88 (t, 3H, J=6.8 Hz, C19'-H$_3$), 1.25–1.35 (m, 8H, C2'-H$_2$, C16'-H$_2$, C17'-H$_2$, C18'-H$_2$), 1.86–1.92 (m, 2H, C1'-H$_2$), 2.03–2.10 (m, 4H, C3'-H$_2$, C15'-H$_2$), 2.25–2.37 (m, 8H, C2-H$_2$, C3-H$_2$, C5-H$_2$, C6-H$_2$), 2.78–2.86 (m, 6H, C6'-H$_2$C3'-H$_2$, C12'-H$_2$), 3.69 (s, 6H, OCH$_3$), 5.31–5.43 (m, 8H, C4'-H, C5'-H, C7'-H, C8'-H, C10'-H, C11'-H, C13'-H, C14'-H).

$^{13}$C NMR (CDCl$_3$, 300 MHz): δ=14.6, 23.1, 24.1, 26.2, 27.4, 27.8, 29.1, 29.9, 30.9, 32.1, 35.4, 52.6, 93.2, 128.1, 128.3, 128.5, 128.9, 129.1, 129.2, 129.9, 131.1, 172.9.

MS (EI): m/z (%)=491 (M$^+$, 16), 460 (72), 444 (50), 429 (28), 413 (70), 393 (42), 381 (28), 357 (36), 333 (14), 301 (50), 207 (26), 181 (32), 164 (34), 150 (40), 133 (40), 121 (50), 106 (71), 93 (86), 80 (78), 79 (100), 67 (98), 55 (60).

HRMS: m/z calcd for $C_{25}H_{45}NO_6$ 491.3247 (M$^+$). Found 491.3247.

Anal. Calcd for $C_{28}H_{45}NO_6$: C, 68.40; H, 9.22; N, 2.85. Found C, 68.77; H, 9.57; N, 2.85.

3-Heptadecyl-3-nitropentane-1,5-dicarboxylic Acid (8a); Typical Procedure

Dimethyl 3-heptadecyl-3-nitropentane-1,5-dicarboxylate (7a) (138 mg, 0.29 mmol) was dissolved in DME (2 mL) and sat. aq LiOH solution (2 mL) was added. The mixture was let stand for 22 h, then it was acidified with dilute HCl (10%, 10 mL) and extracted with EtOAc (2×10 mL). The extracts were concentrated under a stream of dry N$_2$ and the residue was subjected to flash column chromatography on silica (EtOAc/petroleum spirit, 15/85) to afford 3-heptadecyl-3-nitropentane-1,5-dicarboxylic acid (8a) (93 mg, 90%) as a white solid; mp 102° C.

IR (Nujol): ν=3600–2700 (br), 2919 (s), 2852 (s), 1740 (s), 1700 (w), 1652 (w), 1534 (s), 1467 (m), 1454 (m), 1428 (m), 1353 (w), 1323 (m), 1282 (m), 1267 (w), 1234 (m), 1224 (s), 894 (w), 834 (w), 814 (w), 721 (w) cm$^{-1}$.

$^1$H NMR (CDCl$_3$, 300 MHz): δ=0.88 (t, 3H, J=6.8 Hz, C17'-H$_3$), 1.17–1.30[m, 30H, (C2'–C16')-H$_2$], 1.85–1.91 (m, 2H, C1'-H$_2$), 2.26–2.40 (m, 8H, C1-H$_2$, C4-H$_2$, C5-H$_2$).

$^{13}$C NMR (CDCl$_3$, 300 MHz): δ=14.7, 23.3, 23.9, 29.1, 29.4, 29.8, 29.9(0), 29.9(3), 30.0, 30.1, 30.2, 30.3, 32.5, 37.7, 93.8, 179.2.

MS (CI): m/z=461 (M+NH$_4$)$^+$.

MS (EI): m/z (%)=426 [(M−OH)$^+$, 1], 397 (3), 379 (68), 377 (70), 359 (56), 350 (28), 332 (42), 323 (56), 305 (30), 168 (77), 157 (100), 138 (56), 129 (56), 111 (58), 81 (58), 71 (64), 57 (68).

HRMS: m/z calcd for $C_{24}H_{44}NO_5$ 426.3219 (M−OH)$^+$. Found 426.3279.

Anal. Calcd for $C_{24}H_{45}NO_6$: C, 64.98; H, 10.22; N, 3.16. Found: C, 64.55; H, 10.69; N, 2.81.

3-[(all-Z)-Nonadeca-4,7,10,13-tetraenyl]-3-nitropentane-1, 5-dicarboxylic Acid (8b)

Following the procedure described above for synthesis of 3-heptadecyl-3-nitropentane-1,5-dicarboxylic acid (8a), dimethyl 3-[(all-Z)-nonadeca-4,7,10,13-tetraenyl]-3-nitropentane-1,5-dicarboxylate (7b) (110 mg, 0.22 mmol) gave 3-[(all-Z)-nonadeca-4,7,10,13-tetraenyl]-3-nitropentane-1,5dicarboxylic acid (8b) (90 mg, 88%) as a white solid; mp 50–51° C.

IR (film): ν=3400–2300 (br), 3013 (s), 2955 (s), 2927 (s), 2855 (s), 2734 (n), 2630 (m), 1742 (s), 1714 (s), 1538 (s), 1439 (s), 1353 (s), 1321 (s), 1291 (s), 1231 (s), 1068 (m), 989 (m), 918 (s), 833 (s), 807 (m), 803 (m), 732 (m), 678 (m), 622 (w) cm$^{-1}$.

$^1$H NMR (CDCl$_3$, 300 MHz): δ=0.89 (t, 3H, J=6.9 Hz, C19'-H$_3$), 1.21–1.38 (m, 8H, C2'-H$_2$, C16'-H$_2$, C17'-H$_2$, C18'-H$_2$), 1.85–1.91 (m, 2H, C1'-H$_2$), 2.03–2.09 (m, 4H, C3'-H$_2$, C15'-H$_2$), 2.26–2.38 (m, 8H, C1-H$_2$, C2-H$_2$, C4-H$_2$, C5-H$_2$), 2.7–2.86 (m, 6H, C6'-H$_2$, C9'-H$_2$, H$_2$C12'-H$_2$), 5.25–5.47 (m, 8H, C4'-H, C5'-H, C7'-H, C8'-H, C10'-H, C11'-H, C13'-H, C14'-H).

$^{13}$C NMR (CDCl$_3$, 300 MHz): δ=14.7, 23.1, 23.9, 26.2, 27.2, 27.8, 29.2, 29.7, 29.9, 32.1, 36.4, 93.4, 128.1, 128.3, 128.4, 128.9 (2C), 129.2, 130.0, 131.1, 178.8.

MS (EI): m/z (%)=463 (M$^+$, 16), 446 (4), 416 (24), 397 (6), 365 (4), 343 (6), 305 (8), 278 (10), 245 (12), 231 (12), 217 (14), 203 (22), 192 (20),177 (56), 164 (42), 157 (38), 145 (30), 138 (50), 119 (54), 106 (72), 93 (82), 91 (76), 80 (72), 79 (100), 69 (46), 67 (98), 55 (64).

HRMS: m/z calcd for $C_{26}H_{41}NO_6$ 463.2934 (M$^+$). Found 463.2942.

Anal. Cald for $C_{26}H_{41}NO_6$: C, 67.36; H, 8.91; N, 3.02. Found: C, 67.51; H, 9.23; N, 2.92.

Octadecanal (9a); Typical Procedure

PCC (6 g, 27.83 mmol) was suspended in CH$_2$Cl$_2$ (30 mL), and octadecan-1-ol (1a) (5.02 g, 18.57 mmol) in CH$_2$Cl$_2$ (15 mL) was then rapidly added at r.t. The solution became briefly homogeneous before the deposition of the black insoluble reduced reagent. After 2 h, the black mixture was diluted with five volumes of anhyd Et$_2$O, the solvent was decanted, and the black soltd wtas washed twice with Et$_2$O. The crude product was isolated by filtration of the organic solutions through Florisil and concentration of the filtrate under reduced pressure. Purification by flash column chromatography on silica (Et$_2$O/hexane, 4/96) gave octadecanal (9a) (4.02 g, 81%) as a white solid; mp 43–44° C.

IR (Nujol): ν=2960 (s), 2910 (s), 2850 (s), 2705 (w), 1730 (s), 1460 (s), 1375 (s), 720 (w), cm$^{-1}$.

$^1$H NMR (CDCl$_3$, 300 MHz): δ=0.88 (t, 3H, J=6.4 Hz, C18-H$_2$), 1.28 [m, 28H, (C4–C17)-H$_2$], 1.58–1.65 (m, 2H, C3-H$_2$), 2.42 (t, 2H, J=7.3 Hz, C2-H$_2$), 9.76 (s, 1H, CHO).

$^{13}$C NMR (CDCl$_3$, 300 MHz): δ=14.7, 22.7, 23.3, 29.7, 29.9, 30.0, 30.1, 30.3, 32.5, 44.5, 203.6.

MS (EI): m/z (%)=268 (M$^+$, 4), 250 (34), 224 (17), 222 (18), 208 (6), 194 (10), 182 (8), 166 (8), 152 (10), 137 (20), 124 (30), 110 (42), 96 (74), 82 (100), 71 (82), 69 (69), 57 (53), 55 (57).

HRMS: m/z calcd for $C_{18}H_{36}O$ 268.2766 (M$^+$). Found: 268.2765.

Anal. Calcd for $C_{18}H_{36}O$: C, 80.53; H, 13.51. Found: 80.46, H, 13.49.

(all-Z)-Eicosa-5,8,11,14-tetraenal (9b)

According to the procedure described above for preparation of octadecanal (9a), arachidonyl alcohol (1b) (402 mg, 1.38 mmol) gave (all-Z)-eicosa-5,8,11,14-tetraenal (9b) (303 mg, 76%) as a colourless oil.

IR (film): ν=3005 (s), 2960 (s), 2910 (s), 2850 (s), 1730 (s), 1460 (w), 1390 (w), 1160 (w), 920 (w) cm$^{-1}$.

$^1$H NMR DCl$_3$, 300 MHz): δ0.89 (t, 3H, J=6.8 Hz, C20-H$_3$), 1.28–1.34 (m, 6H, C17-H$_2$, C18-H$_2$, C19-H$_2$), 1.69–1.74 (m, 2H, C3-H$_2$), 2.04–2.14 (m, 4H, C4-H$_2$, C16-H$_2$), 2.42–2.45 (m, 2H, C2-H$_2$), 2.79–2.85 (m, 6H, C7-H$_2$,

C10-H₂, C13-H₂), 5.34–5.40 (m, 8H, C5-H, C6-H, C8-H, C9-H, C11-H, C12-H, C14-H, C15H), 9.78 (s, 1H, CHO).

$^{13}$C NMR (CDCl₃, 300 MHz): δ=14.5, 22.3, 23.0, 26.1, 26.9, 27.6, 29.7, 31.9, 43.7, 127.9, 128.2, 128.4, 128.7, 129.0, 129.2, 129.5, 130.9, 202.9.

MS (EI): m/z (%)=288 (M⁻, <1), 244 (1), 234 (1), 217 (2), 203 (3), 177 (9), 164 (13), 150 (30), 131 (12), 119 (19), 106 (39), 93 (56), 91 (64), 80 (77), 79 (100), 67 (93), 55 (43).

HRMS: m/z calcd for C₂₀H₃₂O 288.2453 (M⁺). Found: 288.2449.

Anal. Calcd for C₂₀H₃₂O: C, 83.27; H, 11.18. Found: C, 83.28; H, 11.12.

1-Nitrononadecan-2-ol (10a); Typical Procedure

To a solution of octadecanal (9a) (2.22 g, 8.28 mmol) and nitromethane (1.52 g, 24.90 mmol) in anhyd Et₂O (10 mL), Amberlyst A-21 (1.2 g) was added at r.t. The mixture was stirred and heated at reflux for 48 h. After removal of the Amberlyst A-21 by filtration, the filtrate was concentrated under reduced pressure. Flash column chromatography of the residue (EtOAc/petroleum spirit, 5/95) gave 1-nitrononadecan-2-ol (10a) (2.41 g, 89%) as a white solid; mp 55–56° C.

IR (Nujol): ν=3500–3300 (br), 2960 (s), 2910 (s), 2850 (s), 1550 (m), 1460 (s), 1375 (s), 720 (w) cm⁻¹.

$^{1}$H NMR (CDCl₃, 300 MHz): δ=0.86–0.90 (m, 3H, C19-H₃), 1.26 [m, 30H, (C4–C18)-H₂], 1.43–1.55 (m, 2H, C3-H₂), 2.22–2.43 (bs, 1H, OH), 4.28–4.46 (m, 3H, C1-H₂, C2-H). $^{13}$C NMR (CDCl₃, 300 MHz): δ=14.7, 23.3, 25.7, 29.8(8), 29.9(2), 30.0, 30.1, 30.2, 30.3, 32.5, 34.3, 69.2, 81.2.

MS (CI): m/z=347 (M+NH₄)⁺.

MS (EI): m/z (%)=311 [(M–H₂O)⁺, 3], 294 (32), 282 (9), 276 (27), 267 (31), 250 (34), 240 (6), 222 (15), 208 (8), 194 (9), 179 (7), 165 (10), 151 (16), 137 (37), 123 (62), 109 (85), 97 (95), 95 (100), 83 (100), 69 (88), 57 (92), 55 (92).

HRMS: m/z calcd for C₁₉H₃₇NO₂ 311.2824 (M–H₂O)⁺. Found: 311.2831.

Anal. Calcd for C₁₉H₃₉NO₃: C, 69.25; H, 11.93, N, 4.25. Found: C, 69.54, H, 12.18, N, 4.13.

(all-Z)-1-Nitroheneicosa-6,9,12,15-tetraen-2-ol (10b)

According to the procedure described above for synthesis of 1-nitrononadecan-2-ol (10a), (all-Z)-eicosa-5,8,11,14-tetraenal (9b) (220 mg, 0.76 mmol) gave (all-Z)-1-nitroheneicosa-6,9,12,15-tetraen-2-ol (10b) (240 mg, 90%) as a colourless oil.

IR (film): ν=3600–3300 (br), 3005 (s), 2960 (s), 2910 (s), 2850 (s), 1650 (w), 1550 (s), 1460 (m), 1440 (m), 1380 (s), 1260 (w), 910 (w), 720 (s) cm⁻¹.

$^{1}$H NMR (CDCl₃, 300 MHz): δ0.87–0.91 (m, 3H, C21-H₃), 1.27–1.39 (m, 6H, C18-H₂, C19-H₂, C20-H₂), 1.50–1.56 (m, 4H, C3-H₂, C4-H₂), 2.02–2.16 (m, 4H, C5-H₂, 2.40–2.60 (bs, 1H, OH), 2.80–2.86 (m, 6H, C8-H₂, C11-H₂, C14-H₂), 4.29–4.45 (m, 3H, C1-H₂, C2-H), 5.30–5.45 (m, 8H, C6-H, C7-H, C9-H, C10-H, C12-H, C13-H, C15-H, C16H).

$^{13}$C NMR (CDCl₃, 300 MHz): δ=14.5, 23.0, 25.5, 26.0, 27.1, 27.6, 29.7, 31.9, 33.5, 68.9, 81.0, 127.9, 128.2, 128.5, 128.6, 129.0, 129.1, 129.5, 130.9.

MS (EI): m/z (%)=349 (M⁺, <1), 314 (1), 251 (2), 234 (1), 217 (2), 203 (3), 177 (6), 164 (10), 150 (24), 131 (13), 119 (21), 106 (43), 93 (57), 91 (71), 79 (100), 67 (92), 55 (48).

HRMS: m/z calcd for C₂₁H₃₅NO₃ 349.2617 (M⁺). Found: 349.2614.

Anal. Calcd for C₂₁H₃₅NO₃: C, 72.17; H, 10.09, N, 4.01. Found: C, 72.25, H, 9.91; N, 3.64.

B. Preparation and Activity of Thia Fatty Acids and Sulfides

Experimental $^{1}$H NMR and $^{13}$C NMR spectra were recorded on a Gemini 300 MHz or a Unity Inova 500 MHz spectrometers with tetramethylsilane (TMS) as the internal standard (δ 0.00 ppm). Samples were run in deuterochloroform (99.8% D) unless indicated otherwise. The following abbreviations are adopted: s (singlet); d (doublet); t (triplet); m (multiplet); dd (doublet of doublets); bs (broad singlet). J values are given in Hz.

Infrared (IR) spectra were recorded on Perkin-Elmer 683 and 7700 infrared spectrophotometers. The following abbreviations are used: br (broad), w (weak), m (medium), s (strong).

Ultraviolet spectra were recorded on a Shimadzu UV 2101 PC spectrophotometer with a temperature controller and kinetic software.

Low and high resolution electron ionisation (EI) mass spectra and chemical ionisation (CI) mass spectra were run on a Fisons VG Autospec. A Fisons VG Instrument Quattro II mass spectrometer was used for negative ion electrospray mass spectra. Gas chromatography-mass spectrometry (GC-MS) was carried out with a HP 5970 mass selective detector connected to a HP 5890 gas chromatography with a 12.5 m BP-1 column.

Melting points were determined using a Reichert microscope with a Köfler heating stage and are uncorrected. Buffers were adjusted to the required Ph using a model 520A pH meter. Microanalyses were conducted by the Microanalytical Laboratory, Research School of Chemistry, Australian National University.

HPLC was performed using a Waters HPLC system with ultraviolet (UV) or refractive index (RI) detection. The column used contained Alltech Spherisorb octadecylsilane (ODS) (4.6 mm×250 mm, 3 μm). The mobile phase was comprised of acetonitrile (or methanol) and phosphoric acid (30 mM) solution in the ratios indicated in the text, with a flow rate of 1 ml/min.

Column chromatography was carried out using Merck Silicagel 60 as the absorbent. Analytical TLC was performed on Merck Silicagel 60 F₂₅₄ silica on aluminium baked plates.

15-LO was obtained from Sigma Chemical Company, and 12-LO from Cayman Chemical Company. Arachidonic acid 1, linolenyl alcohol 57a, gamma linolenyl alcohol 57b, arachidonyl alcohol 57c and docosahexaenyl alcohol 57d were purchased from Nu-Chek Prep. Inc. Elysian, Minn., USA. Other chemicals were commercially available from Aldrich Chemical Company.

Determination of Stability of Thia Fatty Acids and Sulfides

Compounds 110 (4.3 mg) and 106 (6 mg) were each dissolved in 5 ml of dichloromethane and added into 250 ml one-neck flasks. Compound 18 (20 mg) and compounds 19, 108, 109 and 111–112 (14–20 mg) were each dissolved in 10 ml of dichloromethane and added into 500 ml flasks. The solvent dichloromethane was then evaporated with continuous rotation of the flasks, allowing the compounds to form thin films. The flasks were flushed with oxygen, sealed and kept in darkness. The compounds in the flasks were redissolved in chloroform-d and analysed by $^{1}$H NMR every two weeks for up to six weeks.

Determination of Antioxidant Behaviour of 3-[(3Z,6Z)-nona-3,6-dienylthio]propionic Acid on Arachidonic Acid Autoxidation This is a typical autoxidation assay designed to investigate the antioxidant properties of thia fatty acids and sulfides in the autoxidation of arachidonic acid 1.

A stock solution in dichloromethane (2 ml) containing arachidonic acid 1 (18 mg) and 3-[(3Z,6Z)-nona-3,6dienylthio]propionic acid 106 (18 mg) was prepared with lauric acid (18 mg) as an internal standard. Samples of the stock solution (100 μl) were added to glass Petri-dishes followed by ethanol (400 μl). After evaporation of the solvent, a well-distributed thin film was formed on each Petri-dish. The Petri-dishes were placed in a desiccator, which was then evacuated, filled with oxygen and stored in the darkness. Dishes were removed from the desiccator after 1, 2, 3, 5 and 7 days. The mixture on each dish was redissolved in diethyl ether and transferred to a 2 ml vial. After evaporation of the solvent, the residue was dissolved in the HPLC mobile phase (100 μl) and 10% of the solution was analysed by HPLC using a reverse phase column (octadecylsilane) (4.6 mm×250 mm, 3 μm) and a refractive index detector. Table 2 shows the mobile phases used for different thia fatty acids and sulfides, and their retention times by HPLC.

TABLE 2

HPLC mobile phase and retention time of thia fatty acids and sulfides

| Compound | Mobile phase (Buffer = 30 mM $H_3PO_4$) | Retention time (min) (Arachidonic acid 1) | Retention time (min) (Lauric acid) | Retention time (min) (Compound) |
|---|---|---|---|---|
| 18 | Acetonitrile-Buffer (80:20) | 6.53 | 4.23 | 8.75 |
| 19 | Acetonitrile-Buffer (80:20) | 6.80 | 4.44 | 10.91 |
| 106 | Acetonitrile-Buffer (70:30) | 14.71 | 7.13 | 3.15 |
| 108 | Methanol-Buffer (90:10) | 6.71 | 4.00 | 10.74 |
| 109 | Methanol-Buffer (90:10) | 6.82 | 4.05 | 9.38 |
| 110 | Acetonitrile-Buffer (95:5) | 3.48 | 3.09 | 14.05 |
| 111 | Acetonitrile-Buffer (95:5) | 3.38 | 3.05 | 21.57 |
| 112 | Acetonitrile-Buffer (90:10) | 5.24 | 3.80 | 6.97 |

Synthesis of Analogues of 3-[(all-Z)-(eicosa-5,8,11,14-tetraenyl-thio)]propionic Acid Pent-2-ynyl p-toluenesulfonate, 102. 2-Pentyn-1-ol 101 (1.03 g, 12 mmol) was dissolved in chloroform (10 ml) and the mixture was cooled in an ice bath. Pyridine (1.90 g, 24 mmol, 2 eq) was then added, followed by p-toluenesulfonyl chloride (3.43 g, 18 mmol, 1.5 eq) in small portions with constant stirring. The reaction was complete in 4 h (monitored by TLC). Ether (30 ml) and water (7 ml) were added and the organic layer was washed successively with 1 N HCl (7 ml), 5% $NaHCO_3$, water (7 ml) and brine (20 ml), and then dried with $Na_2SO_4$. The solvent was removed under reduced pressure and the crude tosylate was flash column chromatographed on silica gel using ether-hexane (20:80) as the eluent to yield the title compound 102 (1.85 g, 65%) as a colourless oil. Found: C, 60.24; H, 5.93; S, 13.22. Calc. for $C_{12}H_{14}SO_3$: C, 60.48; H, 5.92; S, 13.45%. ν $ν_{max}$ (film)/cm$^{-1}$ 2980 (m), 2940 (w), 2878 (w), 2240 (m), 1598 (s), 1495 (w), 1450 (m), 1360 (s), 1180 (s), 1175 (s), 1095 (m), 1020 (m), 1000 (m), 960 (s), 940 (s), 840 (s), 815 (s), 735 (s), 662 (s); $δ_H$ (300 MHz, $CDCl_3$) 0.98–1.03 (3H, m, C5-$H_3$); 2.04–2.10 (2H, m, C4-$H_2$), 2.44 (3H, s, Ar$CH_3$), 4.69 (2H, m, C1-$H_2$), 7.35 and 7.82 (4H, dd, J 8.3 and 8.7, ArH); $δ_C$ (300 MHz, $CDCl_3$) 12.91, 13.72, 22.22, 59.35, 71.72, 92.33, 128.69, 130.30, 133.90, 145.47; m/e (EI): 238 (M$^+$, <0.1%), 209 (1), 155 (24), 139 (100), 129 (6), 117(18), 107 (10), 92 (42), 91 (87), 83 (29), 66 (50), 65 (48).

Nona-3,6-diyn-1-ol, 103. Pent-2-ynyl p-toluenesolfonate 102 (1.37 g, 5.78 mmol, 1.1 eq) was added at −30° C. under nitrogen to a well-stirred suspension in DMF (15 ml) of but-3-yn-1-ol (368 mg, 5.25 mmol, 1 eq), sodium carbonate (834 mg, 7.87 mmol, 1.5 eq), tetrabutylammonium chloride (1.46 g, 5.25 mmol) and copper(I) iodide (1.00 g, 5.25 mmol, 1 eq). The mixture was stirred at room temperature for 48 h. Ether (30 ml) and 1M HCl (30 ml) were then added. After filtration through a bed of celite, the organic phase was washed with brine, dried over sodium sulfate and the solvent was evaporated under reduced pressure. Purification of the residue by flash column chromatography on silica gel with ether-hexane (40:60) as the eluent gave the product 103 (442 mg, 62%) as a colourless oil. Found: C, 79.55; H, 8.82. Calc. for $C_9H_{12}O$: C, 79.37; H, 8.88%. $ν_{max}$ (film)/cm$^{-1}$ 3650–3100 (br), 2975 (s), 2938 (s), 2905 (s), 2880 (s), 2500 (m), 1415 (m), 1375 (w), 1320 (s), 1180 (w), 1120 (w), 1040 (s), 900 (m), 735 (w); $δ_H$ (300 MHz, $CDCl_3$) 1.10 (3H, t, J 7.4, C9-$H_3$), 1.96 (H, bs, OH), 2.13–2.20 (2H, m, C8-$H_2$), 2.41–2.45 (2H, m, C2-$H_2$), 3.11–3.13 (2H, m, C5-$H_2$), 3.69 (2H, t, J 6.1, C1-$H_2$); $δ_C$ (Acetone, 300 MHz) 10.14, 13.07, 14.72, 24.03, 61.95, 75.08, 76.83, 78.46, 82.42; m/e (EI): 135 [(M–H)$^+$, 12%], 121 (44), 107 (30), 105 (51), 103 (29), 93 (44), 91 (100), 79 (58), 77 (80), 65 (41), 63 (29), 57 (14), 53 (27), 51 (37); HRMS: found m/e 135.081144 (M–H)$^+$; calc. for $C_9H_{11}O$: 135.080990.

(3Z,6Z)-Nona-3,6-dien-1-ol, 104. Nona-3,6-diyn-1-ol 103 (198 mg, 1.45 mmol) was hydrogenated at atmospheric pressure, in the presence of a mixture of quinoline (44 mg) and palladium (5%) on calcium carbonate (100 mg), poisoned with lead in methanol (25 ml). The reaction was stopped after 2.5 h when the uptake of hydrogen was 61 ml. Removal of methanol in vacuo, followed by silica gel column chromatography to remove quinoline using ether-hexane (35:65) as the eluent gave 187 mg (92%) of (3Z,6Z)-nona-3,6-dien-1-ol 104 as a colourless oil. Found: C, 77.42; H, 11.75. Calc. for $C_9H_{16}O$: C, 77.09; H, 11.50%. $ν_{max}$ (film)/cm$^{-1}$ 3500–3160 (br), 3011 (s), 2960 (s), 2930 (s), 2870 (s), 1462 (m), 1377 (m), 1050 (m), 722 (m); $δ_H$ (300 MHz, $CDCl_3$) 0.97 (3H, t, J 7.6, H9-$H_3$), 2.01–2.12 (2H, m, C8-H), 2.32–2.40 (2H, m, C2-$H_2$), 2.79–2.84 (2H, t, J 7.1, C5-$H_2$), 3.64 (2H, m, C1-$H_2$), 5.27–5.43 (3H, m), 5.49–5.56 (H, m); $δ_C$ (300 MHz, $CDCl_3$) 14.82, 21.14, 26.20, 31.33, 62.77, 125.90, 127.40, 132.04, 132.74; m/e (EI): 140 (M$^+$, 2%); 122 (15), 111 (7), 109 (12), 107 (22), 98 (12), 96 (19), 95 (21), 93 (72), 91 (33), 81 (39), 79 (56), 68 (31), 67 (100), 55 (59), 54 (21), 53 (21); HRMS: found m/e 140.120290 (M$^+$); calc. for $C_9H_{16}O$: 140.120115.

(3Z,6Z)-Nona-3,6-dienyl p-toluenesulfonate, 105. (3Z,6Z)-Nona-3,6-dien-1-ol 104 (167 mg, 1.19 mmol) was dissolved in chloroform (5 ml) and the solution was cooled in an ice bath. Pyridine (376 mg, 4.76 mmol, 4 eq) was then added, followed by the addition of p-toluenesulfonyl chloride (340 mg, 1.78 mmol, 1.5 eq) in small portions with constant stirring. The mixture was stirred for 24 h at 15° C. Ether (15 ml) and water (5 ml) were added and the organic layer was washed successively with 1 N HCl (10 ml), 5% $NaHCO_3$, water (10 ml), and brine (10 ml), and then dried over $Na_2SO_4$. The solvent was removed under reduced pressure and the crude tosylate was flash column chromatographed on silica gel with ether-hexane (20:80) as the eluent to yield starting material (15 mg, 9%) and the title product 105 (201 mg, 57%) as a colourless oil. Found: C, 65.17; H, 7.44; S, 11.27. Calc. for $C_{16}H_{22}SO_3$: C, 65.28; H, 7.53; S, 10.89%. $\nu_{max}$ (film)/cm$^{-1}$ 3005 (m), 2960 (s), 2930 (m), 2870 (m), 1599 (m), 1462 (m), 1377 (s), 1310 (w), 1290 (w), 1189 (s), 1178 (s), 1100 (s), 1020 (w), 973 (s), 815 (s), 770 (m), 660 (s); $\delta_H$ (300 MHz, CDCl$_3$) 0.95 (3H, t, J 7.6, C9-H$_3$), 2.00–2.05 (2H, m, C8-H$_2$), 2.38–2.44 (2H, m, C2-H$_2$), 2.45 (3H, s, ArCH$_3$), 2.69–2.74 (2H, t, J 7.0, C5-H$_2$), 3.99–4.04 (2H, m, C1-H$_2$), 5.20–5.28 (2H, m), 5.34–5.50 (2H, m) 7.33, 7.80 (4H, dd, J 8.2 and 8.7, AA'BB' and ArH); $\delta_C$ (300 MHz, CDCl$_3$) 14.78, 21.09, 22.20, 26.12, 27.64, 70.20, 123.53, 126.94, 128.47, 130.37, 132.61, 132.92, 145.28; m/e (EI): [277 (M–OH)$^+$, 1%], 155 (25), 139 (2), 122 (67), 107 (47), 93 (100), 91 (77), 79 (66), 67 (47), 55 (32); m/e (CI): 312 (M+NH$_4$)$^+$.

3-[(3Z,6Z)-Nona-3,6-dienylthiolpropionic acid, 106. 3-Mercaptopropionic acid (150 mg, 1.41 mmol, 1.5 eq) was added, under an atmosphere of dry nitrogen, to a stirred solution of sodium methoxide, prepared from sodium (64 mg, 2.78 mmol, 3 eq) and methanol (20 ml). After the initial white precipitate had dissolved, a solution of (3Z,6Z)-nona-3,6-dienyl p-toluenesulfonate 105 (276 mg, 0.94 mmol) in diethyl ether was added. The mixture was stirred at 40° C. for 2 days under nitrogen, then hydrochloric acid (10% v/v, 20 ml) and diethyl ether (20 ml) were poured into the crude reaction mixture. The organic phase was separated and washed with water and brine, and dried over sodium sulfate. After removal of the solvent, the residue was purified by flash column chromatography using ether-hexane-acetic acid (60:40:2) as the eluent to afford 3-[(3Z,6Z)-noca-3,6-dienylthio]propionic acid 106 (88 mg, 41%) as a colourless oil. Found: C, 62.90; H, 8.73; S, 14.01. Calc. for $C_{12}H_{20}SO_2$: C, 63.12; H, 8.83; S, 14.04%. $\nu_{max}$ (film)/cm$^{-1}$ 3400–2500 (br), 3005 (m), 2960 (m), 2910 (m), 2870 (w), 1713 (s), 1459 (m), 1377 (w), 1264 (m), 1195 (w), 1140 (w), 940 (w); $\delta_H$ (500 MHz, CDCl$_3$) 0.97 (3H, t, J 7.8, C9'-H$_3$), 2.05–2.08 (2H, m, C8'-H$_2$), 2.34–2.39 (2H, m, C2'-H$_2$), 2.57–2.60 (2H, t, J 7.4, C1'-H$_2$), 2.65–2.69 (2H, t, J 7.3, C3-H$_2$), 2.78–2.82 (4H, m, C5'-H$_2$, C2-H$_2$), 5.27–5.32 (H, m), 5.37–5.47 (3H, m), 5.50–6.10 (H, bs, COOH); $\delta_C$ (300 MHz, CDCl$_3$) 14.83, 21.14, 26.20, 27.19, 27.95, 32.62, 35.21, 127.37, 127.97, 130.53, 132.72, 178.66; m/e (EI): 228 (M$^+$, 34%), 169 (14), 159 (18), 155 (45), 133 (8), 122 (54), 119 (42), 113 (12), 107 (44), 93 (100), 89 (66), 79 (57), 77 (53), 67 (52), 61 (33), 55 (43); HRMS: found m/e 228.118179 (M$^+$); calc. for $C_{12}H_{20}SO_2$: 228.118402.

3-Tetradecylthiopropionic acid, 108. According to the procedure described for the preparation of 3-[(3Z,6Z)-nona-3,6-dienylthio]propionic acid 106, 3-mercaptopropionic acid (261 mg, 2.46 mmol, 1.2 eq) was added, under an atmosphere of dry nitrogen, to a stirred solution of sodium methoxide prepared from sodium (142 mg, 6.17 mmol, 3 eq) and methanol (20 ml). After the initial white precipitate had dissolved, a solution of 1-bromotetradecane 107 (568 mg, 2.05 mmol) in diethyl ether (2 ml) was added. The reaction mixture was stirred for 16 h at room temperature. After workup and purification by flash column chromatography using ether-hexane (20:80)→ether-hexane-acetic acid (60:40:1) for elution, the title compound 108 (450 mg, 73%) was obtained as a white solid, mp: 67° C. Found: C, 67.32; H, 11.32; S, 10.41. Calc. for $C_{17}H_{34}SO_2$: C, 67.50; H, 11.33; S, 10.60%. $\nu_{max}$ (Nujol)/cm$^{-1}$ 3100–2600 (br), 2965 (s), 2910 (s), 2840 (s), 1680 (s), 1460 (s), 1405 (w), 1375 (m), 1265 (m), 1255 (w), 1231 (w), 1210 (w), 1200 (m), 1080 (w), 915 (m), 725 (m); $\delta_H$ (500 MHz, CDCl$_3$) 0.88 (3H, t, J 6.7, C14'-H$_3$), 1.25–1.38 [22H, m, (C3'–C13')-H$_2$], 1.56–1.61 (2H, m, C2'-H$_2$), 2.54 (2H, bs, C1'-H$_2$), 2.65–2.68 (2H, t, J 6.6, C3-H$_2$), 2.79 (2H, bs, C2-H$_2$); $\delta_C$ (300 MHz, CDCl$_3$) 14.69, 23.26, 27.16, 29.44; 29.80, 29.93, 30.02, 30.10, 30.17, 30.23, 32.49, 32.78, 35.25, 178.50; m/e (EI): 302 (M$^+$, 21%), 230 (24), 229 (100), 185 (2), 161 (4), 119 (8), 106 (24), 97 (15), 89 (21), 83 (22), 69 (25), 55 (32); HRMS: found m/e 302.227166 (M$^+$); calc. for $C_{17}H_{34}SO_2$: 302.227952.

2-Tetradecylthioacetic acid, 109. 2-Mercaptoacetic acid (288 mg, 3.13 mmol, 1.2 eq) was added, under an atmosphere of dry nitrogen, to a stirred solution of sodium methoxide, prepared from sodium (180 mg, 7.83 mmol, 3 eq) and methanol (20 ml). After the initial white precipitate had dissolved, a solution of 1-bromotetradecane 107 (725 mg, 2.61 mmol) in diethyl ether (2 ml) was added and the mixture was stirred for 16 h at room temperature under nitrogen. The crude reaction mixture was poured into an equal volume of hydrochloric acid (10% v/v), and the organic phase was separated and washed with water and brine, and dried over sodium sulfate. After removal of the solvent, the residue was purified by flash column chromatography using diethyl ether-hexane (20:80)→diethyl ether-hexane-acetic acid (60:40:2) for elution and crystallised to afford 2-tetradecylthioacetic acid 109 (580 mg, 77%) as a white solid, mp: 68° C. Found: C, 66.46; H, 10.93; S, 10.83. Calc. for $C_{16}H_{32}SO_2$; C, 66.61; H, 11.18; S, 11.11%. $\nu_{max}$ (Nujol)/cm$^{-1}$ 3200–2600 (br), 2950 (s), 2910 (s), 2840 (s), 1680 (s), 1460 (s), 1425 (w), 1375 (s), 1265 (m), 1140 (w), 908 (w), 725 (w); $\delta_H$ (300 MHz, CDCl$_3$) 0.88 (3H, t, J 6.6, C14'-H$_3$), 1.26–1.40 [22H, m, (C3'–C13')-H$_2$], 1.56–1.64 (2H, m, C2'-H$_2$), 2.64–2.69 (2H, t, J 7.4, C1'-H$_2$), 3.26 (2H, s, C2-H$_2$), $\delta_C$(300 MHz, CDCl$_3$) 14.68, 23.26, 29.30, 29.46, 29.75, 29.93, 30.06, 30.15, 30.22, 32.49, 33.36, 34.05, 177.57; m/e (EI): 288 (M$^+$, 12%), 230 (21), 229 (100), 111(6), 97 (17), 83 (27), 69 (30), 55 (34); HRMS: found m/e 288.212125 (M$^+$); calc. for $C_{16}H_{32}SO_2$: 288.212302.

Propyl (all-Z)-eicosa-5,8,11,14-tetraenyl sulfide 110. Using the procedure described for the preparation of 3-tetradecylthiopropionic acid 108, propanethiol (26 mg, 0.34 mmol, 1.2 eq) was added, under an atmosphere of dry nitrogen, to a stirred solution of sodium methoxide, prepared from sodium (20 mg, 0.87 mmol, 3 eq) and methanol (10 ml). After the initial white precipitate had dissolved, a solution of (all-Z)-1-bromo-5,8,11,14-eicosatetrane 58c (101 mg, 0.29 mmol) in diethyl ether (1 ml) was added. The reaction mixture was stirred for 15 h at room temperature. After workup, purification by flash column chromatography using hexane for elution gave the title compound 110 (75 mg, 75%) as a colourless oil. Found: C, 78.91; H, 11.38; S, 8.96. Calc. for $C_{23}H_{40}S$: C, 79.24; H, 11.56; S, 9.20%. $\nu_{max}$ (film)/cm$^{-1}$ 3005 (s), 2950 (s), 2920 (s), 2850 (s), 1650 (w), 1450 (m), 1390 (w), 1375 (w), 1290 (w), 1260 (w), 1230 (w), 910 (w), 720 (m); $\delta_H$ (CDCl$_3$, 300 MHz) 0.89 (3H, t, J 6.8, C20-H$_3$), 0.99 (3H, t, J 7.2, C3-H$_3$), 1.26–1.35 (6H, m, C17-H$_2$, C18-H$_2$, C19-H2), 1.43–1.48 (2H, C3-H2), 1.57–1.64 (4H, m, C2-H2, C2'-H2), 2.05–2.13 (4H, m, C4-H2, C16-H2), 2.50–2.51 (4H, m, C1-H2, C1'-H2), 2.80–2.86 (6H, m, C7-H2, C10-H2, C13-H2), 5.32–5.43 (8H, m, C5-H, C6-H, C8-H, C9-H, C11-H, C12-H, C14H, C15-H); $\delta_C$ (CDCl$_3$, 300 MHz) 14.13, 14.67, 23.17, 23.60, 26.22, 27.41, 27.81, 29.44, 29.91, 32.11, 32.54, 34.79, 128.12, 128.48, 128.64(2C), 128.90, 129.11, 130.40, 131.06; m/e (EI): 348 (M$^+$, 44%), 305 (38), 273 (4), 251 (6), 237 (14), 205 (17), 177 (19), 161 (36), 150 (27), 131 (29), 119 (40), 105 (48), 93 (77), 91 (76), 81 (79), 79 (95), 67 (100), 55 (69); HRMS: found m/e 348.285378 (M$^+$); calc. for $C_{23}H_{40}S$: 348.285073.

Propyl tetradecyl sulfide, 111. Using the procedure described above for the synthesis of propyl (all-Z)-eicosa-5,8,11,14-tetraenyl sulfide 110, propanethiol (165 mg, 2.16 mmol, 1.2 eq) was added, under an atmosphere of dry nitrogen, to a stirred solution of sodium methoxide, prepared from sodium (82 mg, 3.56 mmol, 2 eq) and methanol (10 ml). After the initial white precipitate had dissolved, a solution of 1-bromotetradecane 107 (500 mg, 1.80 mmol) in diethyl ether (2 ml) was added. The reaction mixture was stirred for 15 h at room temperature. After workup, purification by flash column chromatography using hexane for elution gave the title compound 111 (435 mg, 89%) as a colourless oil. Found: C, 75.05; H, 13.27; S, 11.50. Calc. for $C_{17}H_{36}S$: C, 74.92; H, 13.31; S, 11.76%. $\nu_{max}$ (film)/cm$^{-1}$ 2960 (s), 2910 (s), 2850 (s), 1460 (s), 1375 (w), 1290 (w), 1270 (w), 890 (w), 720 (w); $\delta_H$ (CDCl$_3$, 300 MHz) 0.87 (3H, t, J 6.5, C14'-H$_3$), 0.99 (3H, t, J 7.4, C3'-H$_3$), 1.25 [22H, m, (C3–C13-H$_2$], 1.54–1.63 (4H, m, C2-H$_2$, C2'-H$_2$), 2.47–2.51 (4H, m, C1-H$_2$, C1'-H$_2$); $\delta_C$ (CDCl$_3$, 300 MHz) 14.13, 14.71, 23.28, 23.59, 29.55, 29.85, 29.94, 30.12, 30.18, 30.23, 30.33, 32.50, 32.69, 34.78; m/e (EI): 272 (M$^+$, 52%), 243 (18), 229 (100), 196 (8), 187 (2), 168 (5), 145 (6), 131 (15), 111 (14), 97 (22), 89 (34), 83 (27), 76 (33), 69 (32), 57 (30), 55 (44).

3-(Tetradecylsulfinyl)propionic acid, 113. Arachidonic acid 1 (175 mg) was dissolved in 5 ml of dichloromethane to make a stock solution (35 mg/ml). 3-Tetradecylthiopropanoic acid 108 (10 mg, 0.03 mmol), arachidonic acid 1 (10 mg, 0.03 mmol, 284 μl) and dichloromethane (10 ml) were added into a one-neck flask (500 ml). The solvent was evaporated using a rotary evaporator to allow the reagents to form a thin film on the internal surface of the flask. The flask was filled with oxygen and placed in darkness for 7 days. Dichloromethane (5 ml) was then added into the flask to dissolve the mixture and the solution was then transferred to a 2 ml vial. After evaporation of the solvent, the residue was dissolved in 300 μl of the mobile phase (methanol-30 mM phosphoric acid, 90:10) and then subject to reverse phase HPLC analysis. The HPLC was performed on an Alltech Spherisorb octadecylsilane (ODS) column with RI detection. The flow rate of the mobile phase was 3 ml/min. Fifty microlitres of the sample was loaded each time. The product with a retention time of 5.49 min was collected and pooled. After evaporation of the solvent at reduced pressure, the product was extracted with diethyl ether (2 ml). The resulting extract was washed with water and dried with Na$_2$SO$_4$ and the solvent evaporated, yielding the title compound 113 (2 mg) as a white solid, mp: 166–167° C. Found: 64.33, H, 10.50. Calc. for $C_{17}H_{34}SO_3$: C, 64.11; H, 10.76%. $\nu_{max}$ (Nujol)/cm$^{-1}$ 3600–2500 (br), 2965 (s), 2910 (s), 2840 (s), 1695 (m), 1460 (s), 1375 (s), 1330 (w), 1305 (w), 1125 (w), 1040 (w), 1025 (w), 920 (w), 720 (w); $\delta_H$ (CDCl$_3$, 500 MHz) 0.81 (3H, t, J 7.0, C14'-H$_3$), 1.19–1.26 [20H, m, C4'–C13')-H$_2$], 1.34–1.37 (2H, m, C3'-H$_2$), 1.68–1.72 (2H, m, C2'-H$_2$), 2.70–2.76 (H, m), 2.82–2.89 (3H, m), 2.88–3.03 (H, m), 3.05–3.10 (H, m), 7.96 (H, bs, COOH); $\delta_C$ (CDCl$_3$, 300 MHz) 14.67, 23.19, 23.24, 27.78, 29.29, 29.72, 29.91, 30.09, 30.17, 30.20, 32.47, 46.66, 52.53, 174.37; m/e (CI): 319 (MH$^+$); m/e (EI): 301 [(M−OH)$^+$, 27%], 246 (21), 245 (16), 229 (100), 196 (5), 121 (15), 94 (22), 97 (22), 83 (29), 71 (32), 70 (34), 57 (51); HRMS: found m/e 301.219714 (M−OH)$^+$; calc. for $C_{17}H_{33}SO_2$: 301.220127.

2-(Tetradecylsulfinyl)acetic acid, 114. 2-Tetradecylthioacetic acid 109 (19 mg, 0.066 mmol) was dissolved in dichloromethane (2 ml) and tert-butylhydroperoxide (11 ml, 0.08 mmol, 1.2 eq) was added. After 48 h reaction at room temperature, the solvent was removed and the residue was chromatographed using ether-hexane-acetic acid (60:40:2)→methanol as the eluent to obtain the white product 114 (17 mg, 86%). $\delta_H$ (CDCl$_3$, 300 MHz) 0.88 (3H, t, J 6.4, C14'-H$_3$), 1.20–1.29 [20H, m, (C4'–C13)-H$_2$], 1,44–1.50 (2H, m, C3'-H$_2$), 1.77–1.82 (2H, m, C2'-H$_2$), 2.88–2.95 (H, m, C1'-H), 3.02–3.07 (H, m, C1'-H'), 3.63–3.68 (H, d, J 14, C2-H), 3.81–3.86 (H, d, J 14, C2-H'), 7.92 (H, bs, COOH); $\delta_C$ (CDCl$_3$, 300 MHz) 14.69, 23.20, 23.26, 29.18, 29.70, 29.89, 29.93, 30.09, 30.18, 30.22, 32.49, 52.27, 53.47, 166.93; m/e (EI): 305 [(M+1)$^+$, 1%], 287 (50), 243 (60), 229 (94), 196 (12), 168 (6), 149 (6), 125 (10), 111 (21), 97 (45), 83 (63), 69 (74), 57 (100), 55 (91); HRMS: found m/e 305.215275 (M+1)$^+$ calc. for $C_{16}H_{33}SO_3$: 305.215042.

C. Determination of Biological Activity of Novel Nitro Compounds [4a (Lx1); 4b (Lx4); 6a (Lx6); 6b (Lx7); 8a (Lx8) and 8b (Lx9)]

(1) Investigation of 15-LO, 5-LO and 12-LO Catalysed Oxidation of the Nitro Compounds (4a, 4b, 6a, 6b, 8a and 8b; Table 1)

It has been suggested the various hydroxy and hydroperoxy fatty acid derivatives (such as 15-HETE and 15 HPETE) have inhibitory effects on lipoxygenase enzymes.[35] Based on this consideration, 5-LO, 12-LO and 15-LO catalysed oxidation of the nitro compounds (4a, 4b, 6a, 6b, 8a and 8b) was investigated. Each of the nitro compounds was treated with 15-LO in pH 9.0 buffer (or 5-LO in pH 6.3 buffer and 12-LO in pH 7.4 buffer), and the formation of 15-hydroperoxy derivatives (or 5-hydroperoxy or 12-hydroperoxy derivatives) over time was monitored by UV spectroscopy at 234 nm. The result shows that, among the nitro compounds, compound 6b was the only one that underwent lipoxygenase catalysed oxidation. It served as a substrate for both 15-LO and 12-LO, but not for 5-LO.

(2) The Effect of Nitro Compounds 4a (Lx1), 4b (Lx4), 6a (Lx6), 6b (Lx7), 8a (Lx8) and 8b (Lx9) on 15-LO, 5-LO and 12-LO Catalysed Oxidation of Arachidonic Acid The result from the preliminary experiment is summarised in Table 3. It shows that compound 8a has an inhibitory effect on 15-LO but not on 5-LO, while compound 6a displays complementary activity inhibiting 5-LO but not 15LO. Neither 8a nor 6a inhibits 12-LO. Compound 8b appears to have a significant inhibitory effect on 12-LO catalysed oxidation of arachidonic acid, giving a relatively long lagtime at the early stage of arachidonic acid oxidation.

(3) The Inhibitory Effect of 15-hydroperoxy and 15-hydroxy Derivatives from Compound 6b on 15-LO Catalysed Oxidation of Arachidonic Acid An enzyme assay shows that these two compounds did have inhibitory effect on 15-LO catalysed oxidation of arachidonic acid, giving IC$_{50}$ values of 50 μM for 15-hydroperoxy derivative of 6b and 120 μM for 15-hydroxy derivative of 6b.

(4) Determination of K$_m$ and V$_{max}$ for 15-LO Catalysed Oxidation of Compound 6b, and Inhibitor Constant of Compound 8a on 15-LO Catalysed Oxidation of Arachidonic Acid The Michaelis constant K$_m$ and the value of V$_{max}$ for 15-LO catalysed oxidation of compound 6b were measured and calculated based on the Lineweaver Burke equation, with K$_m$ as 8.4 μM and V$_{max}$ as 24.48 μM/min.

The inhibitor constant (K$_i$ or K$_I$) of compound 8a was also determined. The graph of 1/v vs 1/[s] with varying concentrations of compound 8a indicates that the inhibition is of the mixed inhibition pattern as shown in the following scheme. Thus the K$_i$ and K$_I$ values in the scheme were calculated giving the result of 27.42 μM for K$_i$ and 55.15 μM for K$_I$.

TABLE 3

Effect of nitro compounds on oxidation of arachidonic acid (AA) catalysed by 15-LO, 5-LO or 12-LO

| Compounds | Effect on 15-LO catalysed oxidation of AA | Effect on 5-LO catalysed oxidation of AA | Effect on 12-LO catalysed oxidation of AA |
|---|---|---|---|
| Lx1 | Nil | Nil | Nil |
| Lx4 | Nil | Nil | Nil |
| Lx6 | Activatory | Inhibitory $IC_{50} = 60\ \mu M$ | Activatory |
| Lx8 | Inhibitory $K_i = 27.42\ \mu M$ $K_i = 55.15\ \mu M$ | Nil | Activatory |
| Lx7 | Substrate $K_m = 8.4\ \mu M$ $V_{max} = 24.48\ \mu M/min$ | Activatory | Substrate |
| Lx9 | Nil | Activatory | Inhibitory |
| Lx2 | Nil | Nd | Nd |
| Lx3 | Nil | Nd | Nd |
| Lx5 | Nil | Nd | Nd |

Nd = Not done

D. Antimalarial Properties of Nitre Compounds

It has been estimated that 1 to 3 million individuals per year, primarily children, die from *Plasmodium falciparum* infections and that the parasite is responsible for hundreds of millions of clinical infections world-wide. Widespread drug resistance displayed by the parasite, coupled with the fact that the vector *Anopheles* mosquito shows insecticide resistance, has led to a deteriorating situation where we possess fewer tools to fight the disease than we had some forty years ago. The limited number of anti-malarial drugs available has contributed to drug resistance. There is a need to develop new drugs which may supplement existing antimalarials.

Recently we have demonstrated the antimalarial properties of purified polyunsaturated fatty acids (PUFA), both in vitro and in vitro[36]. Both n-6 and n-3 fatty acids were effective as shown by their ability to cause intraerythrocytic death of the asexual forms of *P. falciparum*[36], and by the ability to significantly depress the parasitaemia in mice infected with *P. berghei*[36]. Studies on fatty acid structure and its relation to intraerythrocytic killing of parasites demonstrated that these effects were dependent on specific structural elements of the fatty acids. Thus the activity was dependent on carbon chain length, degrees of unsaturation, hydroxylation and hydroperoxidation[36]. The saturated twenty carbon fatty acid had very little parasite killing activity compared to the corresponding unsaturated twenty carbon fatty acids 20:4n-6 and 20:5n-3[36].

Unsaturated fatty acids with 18 carbons were also quite effective if these had at least two double bonds, such as 18.2n-6, but 18:1n-9 showed similar activity to saturated fatty acids[36]. Pre-oxidation of 20:4n-6 and 22:6n-3 prior to addition to the *P. falciparum* infected erythrocytes resulted in an increase in antiparasite activity[36]. Addition of antioxidants to the infected erythrocytes markedly reduced the activity of these fatty acids[36]. Further studies showed that the hydroxy and hydroperoxy derivatives of these PUFA were more active than their parent fatty acids[36].

These results have suggested that the hydroperoxy derivative, in particular, displayed the most active antiparasite effect. It also illustrated that the conversion of 20:4n-6/22:6n-3 to the oxidised forms was essential for antiparasite activity. Most likely, the parasites were particularly sensitive because of the delicate environment within the erythrocyte. Supporting this idea was our finding(unpublished) that the extracellular blood flagellate, *Trypanosoma lewisi*, was relatively resistant to similar concentrations of fatty acids. The effects of fatty acids were not due to damage to erythrocytes[36]. When in vivo studies were extended to treatment with hydroperoxy derivatives of PUFA, these were found to be even more effective than the PUFA (unpublished observations).

A limitation in the use of PUFA in diseases such as malaria is their ability to activate neutrophil and macrophage and induce the non-specific release of oxygen derived reactive species, lysosomal enzyme release and increased adhesion to endothelial cells[37-45]. Furthermore, it has recently been demonstrated that PUFA synergise with the cytokine, tumour necrosis factor, to increase oxygen radical production in neutrophils[46]. These properties could exacerbate the illness in malaria. In contrast to the parent PUFA, the hydroxy- and hydroperoxy-derivatives lack the neutrophil stimulating activity[39,41,43]. This makes these derivatives, especially the hydroperoxy-PUFA, attractive as models on which the synthesis of a range of compounds could be based, and which could be examined for their antimalarial properties. The compounds of particular interest are the nitroso-PUFA which are more stable.

The series of nitro long chain saturated and unsaturated molecules (designated Lx compounds) presented in Table 1 are a new class of antimalarial agents based on fatty acids which may be established as lead compounds for malaria chemotherapeutic drugs. These compounds have been examined for the action of engineered fatty acids of different structures for their antimalarial activity against asexual blood stages of *P. falciparum* (human parasite) in vitro and in murine *P. berghei* infections.

(1) Using the LX Compounds on Asexual Blood Stages of *P. falciparum*

Using the radiometric assay[36], the effects of the Lx compounds were examined for antimalarial activity. The *Plasmodium falciparum* isolates used were 3D7, FC27, $K^1$ and $K^+$. These were maintained in human blood group $O^+$ erythrocytes essentially as described previously using RPM-1640 (HEPES modification) supplemented with 0.25% D-glucose, 0.2% Tess buffer (Sigma Chemical Co, Lt Louis, Mo.) and 10% heat inactivated (56° C., 20 min) human blood group AB serum. Cultures were maintained in tissue culture flasks (Corning, N.Y.) at 37° C. under an atmosphere of 1% $_2$, 5% $CO_2$ in $N_2$. *P. falciparum* cultures containing approximately 3.0:% parasitaemia were adjusted to $1 \times 10^8$ erythrocytes/ml. To 50 $\mu l$ of the parasite-erythrocyte culture ($5 \times 10^6$ erythrocytes) in wells of 96-well microdilution plates wvas added 50 $\mu l$ of the designated concentration of fatty acid or equivalent amounts of solutions or media. The treated cultures were incubated at 37° C. for 4 h and then pulsed with 50 $\mu l$ (2.5 $\mu Ci$) of $^3H$-hypoxanthine. After a further 18 h incubation the parasites-erythrocytes were harvested onto glass fibre filter papers using a cell harvester. The amount of radioactivity incorporated was measured in a β-counter. The results have been expressed as % inhibition of parasite growth i.e. the dpm in the fatty acid diluent–dpm in the fatty acid treated cultures/dpm in diluent×100.

FIG. 1 illustrates the effects of chemically engineered nitro compounds on *P. falciparum* 3D7. Results are the mean ±SEM of 3 to 10 experiments. It can be seen that 19:3(n-6)-$NO_2$ (Lx3) had the greatest activity. The compounds Lx1 to Lx5 did not contain a carboxyl group. In terms of these five compounds it is evident that, apart from Lx3, there was no increase in antimalarial activity of the compounds by introducing double bonds. It is possible that the difference in activity seen between Lx2 and Lx3 is due to the position of the double bonds, ie the n-6 is more active than the n-3. Perhaps the reason why activity is lost with Lx4 is because of the increase in carbon chain length.

Figure 2:
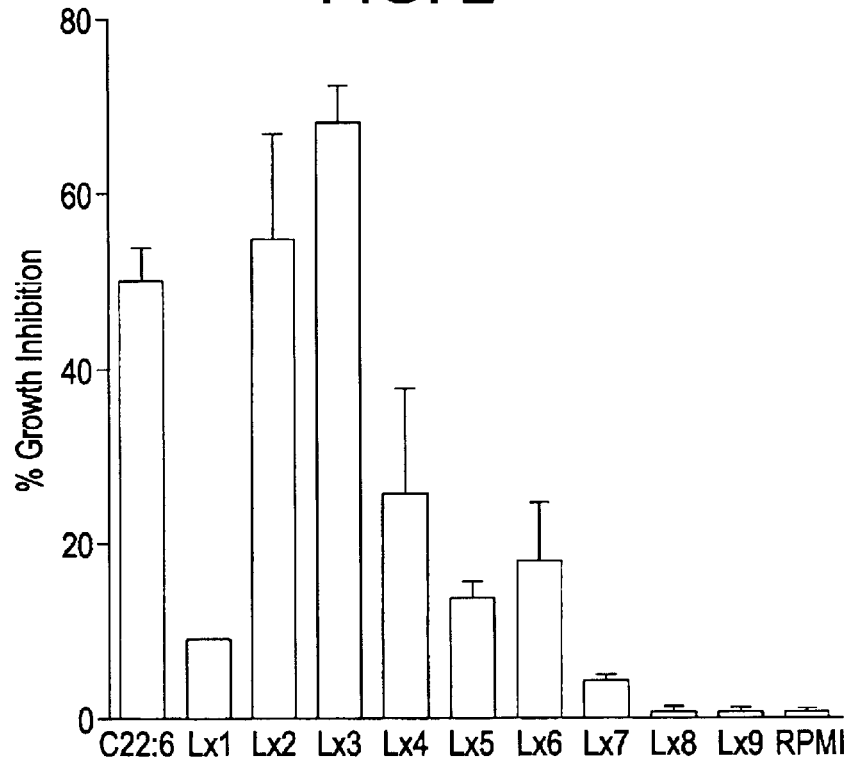
FIG. 2 illustrates the antimalarial properties of Lx2 to 9 on $P.$ $falciparum$ K+ isolates. The results are the mean +/−SEM of 12 determinations from 2 experimental runs.
Figure 3:
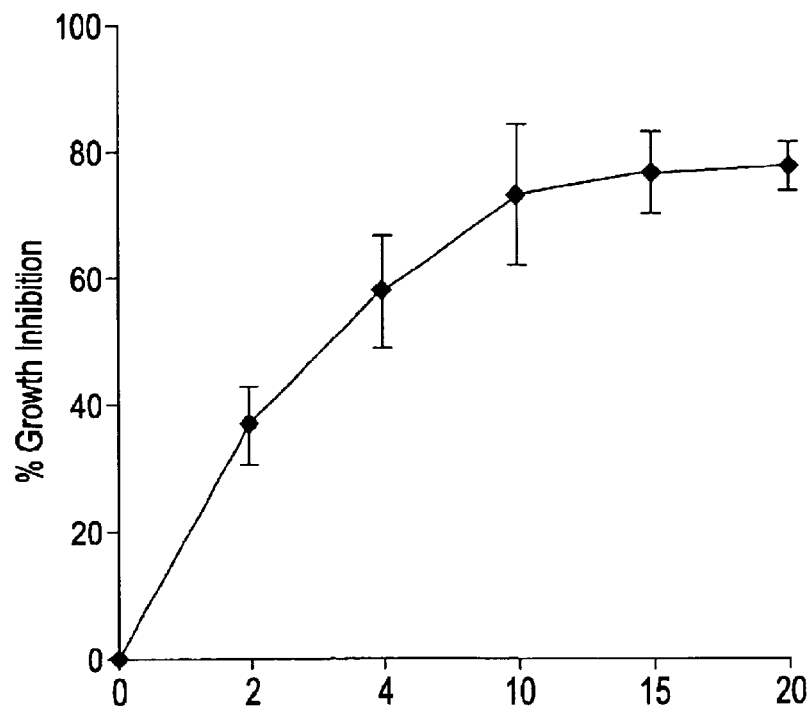
FIG. 3 illustrates the typical concentration related effect of the antimalarial properties of these compounds for Lx3 on $P.$ $falciparum$ 3D7 isolates. The results are the mean +/−SEM of triplicates and relate to a representative experiment. Lx3 had an EC50 of 6,2 and 3 $\mu$g/ml for activity against isolates FC27, 3D7 and K+, respectively. In comparison, the EC50 for 22:6n-3 against FC27 and K+ strain were 12 $\mu$g/ml and 4 $\mu$g/ml, respectively.

Similar results were seen when a different parasite isolate was used. The data for the antimalarial properties of Lx1 to 9 on P. falciparum K+ isolate are shown in FIG. 2. The results are the mean ±SEM of 12 determinations from 2 experimental runs. A typical concentration related effect of the antimalarial properties of these compounds is shown for Lx3 on P. falciparum 3D7 isolate (FIG. 3). The results are the mean ±SEM of triplicates and relate to a representative experiment. Lx3 had an $EC_{50}$ of 6, 2 and 3 µg/ml for activity against isolates FC27, 3D7 and K+, respectively. In comparison, the $EC_{50}$ for 22:6n-3 against FC27 and K+ strain were 12 µg/ml and 4 µg/ml, respectively.

Figure 4:
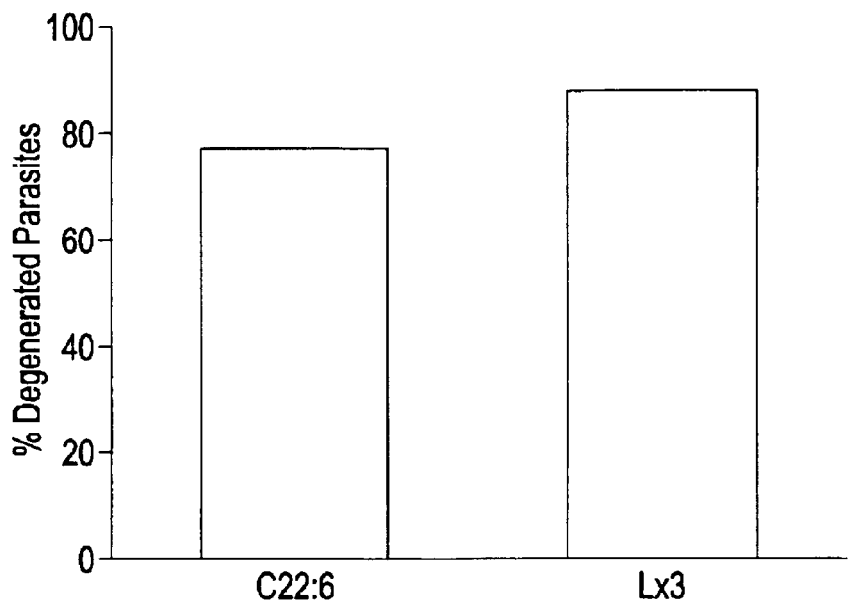
FIG. 4 shows the results of examination of parasites by morphological criteria. Parasites were treated with 20 $\mu$g/ml of compound. Results are means of triplicate assays of one experiment and are consistant with that found in three experiments.

FIG. 4 shows the results of examination of parasites by morphological criteria. Parasites were treated with 20 µg/ml of compound. Results are means of triplicate assays of one experiment and are consistent with that found in three experiments. Morphological examination of cultures essentially supported the results of those of the radiometric technique where cultures showed degenerate mature rings, trophozoites and shizonts in the presence of Lx3 and there was no general lysis of erythrocytes.

Figure 5:
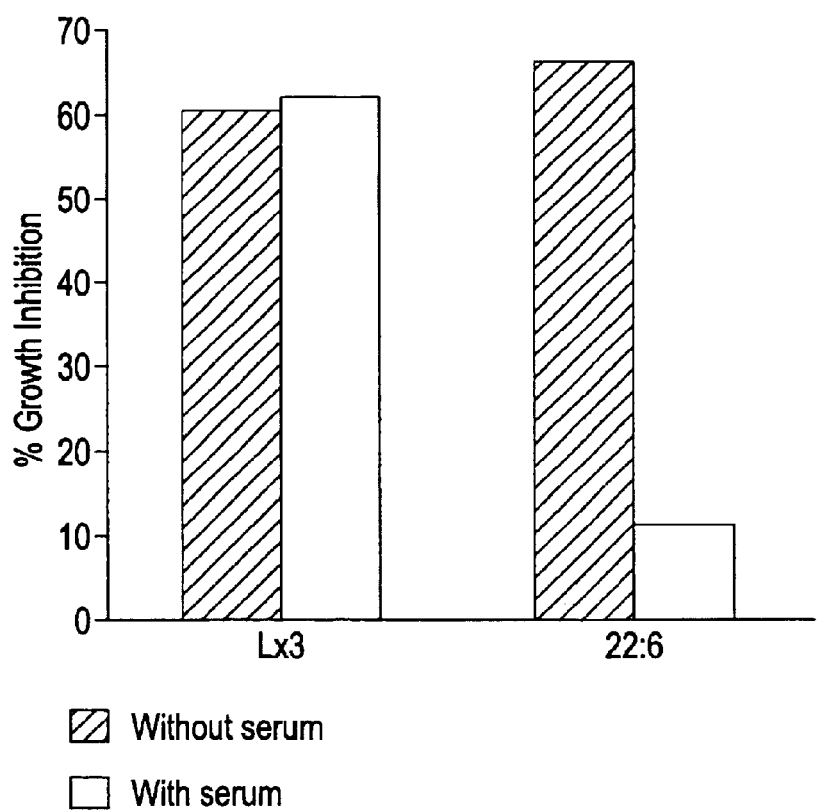
FIG. 5 shows the effects of human serum on the ability of 22:6 n-3 and Lx3 (19:3 n-6-NO2) to kill asexual blood stages of $P.$ $falciparum$ in culture. The compounds were tested at 20 $\mu$g/ml. Results are the means of six determinations. The data show that, while that antimalarial activity of 22.6n-3) was substantially reduced (85%) by serum, the presence of serum did not affect the activity of Lx3.

The Lx3 compound, without a carboxylic acid group, would be expected to be handled quite differently from compounds with a carboxylic acid group by fatty acid binding proteins and by the enzymes that metabolise fatty acids. It was therefore of major interest to examine whether or not Lx3 was affected by alburrin which normally binds and sequesters fatty acids. FIG. 5 shows the effects of human serum on the ability of 22:6 n-3 and Lx3 (19:3 n-6-$NO_2$) to kill asexual blood stages of P. falciparum in culture. The compounds were tested at 20 µg/ml. Results are the means of six determinations. The data in FIG. 5 show that, while the antimalarial activity of 22:6n-3 was substantially reduced (85%) by serum, the presence of serum did not affect the activity of Lx3.

(2) Incorporation of Lx3 into Parasitised Erythrocytes

Because Lx3 is emerging as an interesting molecule with unique properties, a study was conducted to examine whether parasitised erythrocytes incorporated more of the Lx3 than normal erythrocytes as well as investigating the cellular distribution of Lx3.

Figure 6:
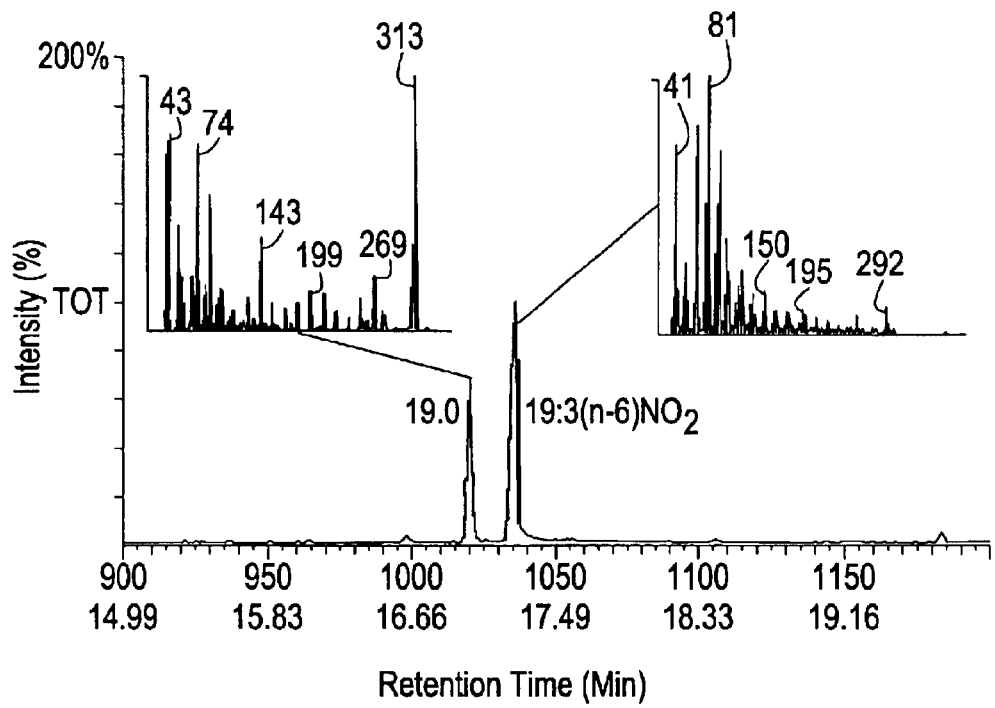
FIG. 6 shows the GC-Ms (expanded view) of Lx3 isolated from parasited RBC. The mass spectrum of each peak unambiguously identifies 19:0 and Lx3 (19:3(n-6)-NO2. Lx3 was found to be taken up by the cells and remained exclusively in the unesterified form.

Red blood cells or parasitised red blood cells (K+ strain, 9.25% parasitaenia) ($5 \times 10^8$ cells) were incubated with 200 µg of Lx3 in 10 mls of HBSS at 37° C. for 4 h. The incubate was centrifuged (3,000 rpm for 10 min) and the medium aspirated. The cell pellet was washed 3 times with 5 ml of HBSS with centrifugation. Lipids were extracted from the cell pellet and neutral lipids, phospholipids and unesterffied Lx3 were resolved by thin-layer chromatography. The neutral lipid and phospholipid samples were transesterified to release any bound Lx3. The amount of Lx3 associated with the unesterifield, neutral lipid and phospholipid fractions was quantitated by gas-liquid chromatography using nonadecanoic acid (nonadecylic acid (19:0)) methyl ester (48 nmol) as a reference standard. For definitive identification of Lx3 and possible products (elongation, de-saturation, shorter-chain products), a combined gas-liquid chromatography-mass spectrometry (GC-MS) technique was employed. FIG. 6 is the GC-MS (expanded view) of Lx3 isolated from parasitised RBC. The mass spectrum of each peak unambiguously identifies 19:0 and Lx3 (19:3(n-6)-$NO_2$) respectively. Lx3 was found to be taken up by the cells and remained exclusively in the unesterified form. No Lx3 was esterified in neutral lipids and phospholipids (Table 4). It is important to note that parasitised red blood cells took up approximately 6 times more Lx3 than non-parasitised cells. No elongation, chain-shortening or de-saturation products of Lx3 were detected in either cell population. The lack of derivatisation or incorporation of Lx3 into neutral lipids and phospholipids is almost certainly due to Lx3 not having a carboxylic acid group which is mandatory for the conversion of a fatty acid to its coenzyme A ester. Since Lx3 does not appear to be readily metabolised in the cell, more will be available to kill the parasite.

TABLE 4

Summary of the incorporation of Lx3 into normal and P. falciparum infected red blood cells. The results represent the mean ± SEM of four analyses and are expressed as % of total recovered Lx3. ND. Not detectable.

| | Recovered cellular Lx3 (% of total added) | |
|---|---|---|
| Lipid Fraction | Red Blood Cells | Parasitised red blood cells |
| Unesterified Lx3 | 2.1 ± 0.2 | 12.9 ± 0.4 |
| Neutral lipids | N.D. | N.D. |
| Phospholipids | N.D. | N.D. |

(3) Effects of Nitro/Nitro Fatty Acid Compounds on Neutrophil Functions

The activation of human neutrophils by nitro compounds was assessed by the ability to stimulate superoxide production (chemiluminescence response) and release of lysosomal enzymes from specific and azurophilic granules. Neutrophils were prepared from whole blood taken from normal healthy volunteers by the rapid-single step procedure[41]. Briefly, blood anticoagulated with heparin was carefully layered on a hypaque-ficoll medium of 1.114 g/ml and centrifuged in swing-out-buckets at 200 g/30 min. The leukocytes were resolved into two bands and the erythrocytes sedimented at the bottom of the tube. The second leukocyte band approximately 0.7 cm from the mononuclear cell containing band at the interface contained neutrophils of >98% purity and >99% viability (trypan blue dye exclusion criteria). The neutrophils were carefully harvested with a pasteur pipette, and washed and resuspended in tissue culture medium. The respiratory burst response of neutrophils was assessed by measuring superoxide production by the lucigenin dependent chemiluminescence assay essentially as described previously[42]. Briefly, $1 \times 10^6$ neutrophils (100 µl) in HBSS were treated with the nitro analogues of fatty acids (100 µl), then lucigenin was added and the volume made up.

Figure 7:
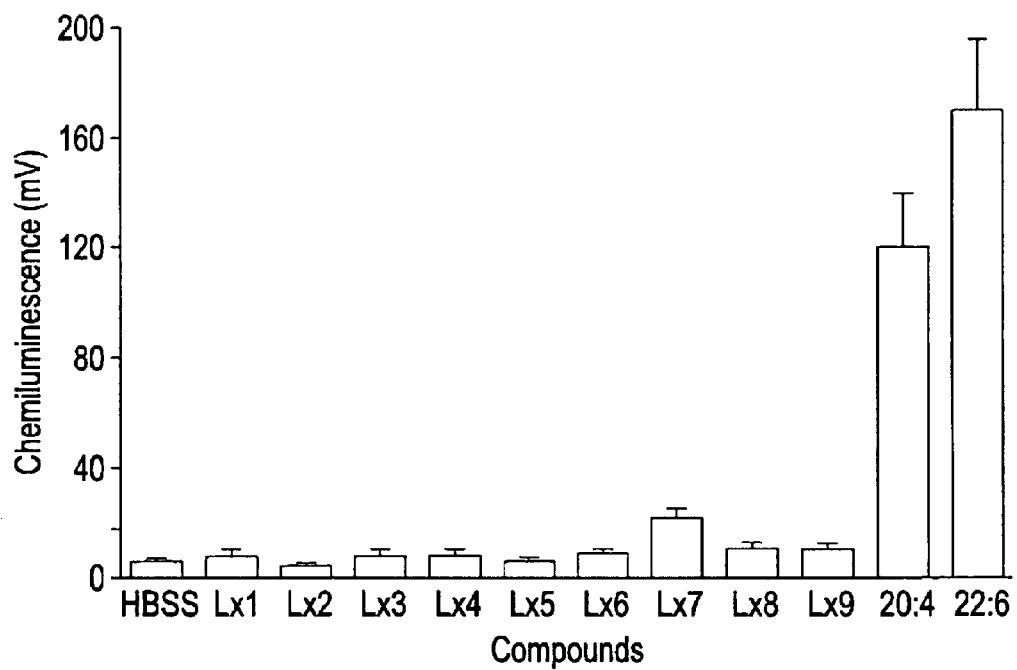
FIG. 7 demonstrates the pattern of neutrophil activation reflected in the degranulation response. Both in relation to release of vitamin B12 binding protein (specific granule maker) and β-glucuronidase (azurophilic granule marker), all of the Lx compounds except for Lx7 were poor inducers of the release of vitamin B12 binding protein as well as release of β-glucuronidase.

FIG. 7 illustrates the effects of Lx compounds on the neutrophil chemiluminescence reponse. Results are the means ±SEM of 4–12 experiments. Each compound was tested at 20 µM. The results showed that all the compounds (Lx1–Lx9), apart from Lx7, did not induce a chemiluminescence response. Even the response induced by Lx7 was marginal compared to 20:4n-6 and 22:6n-3.

Figure 8:
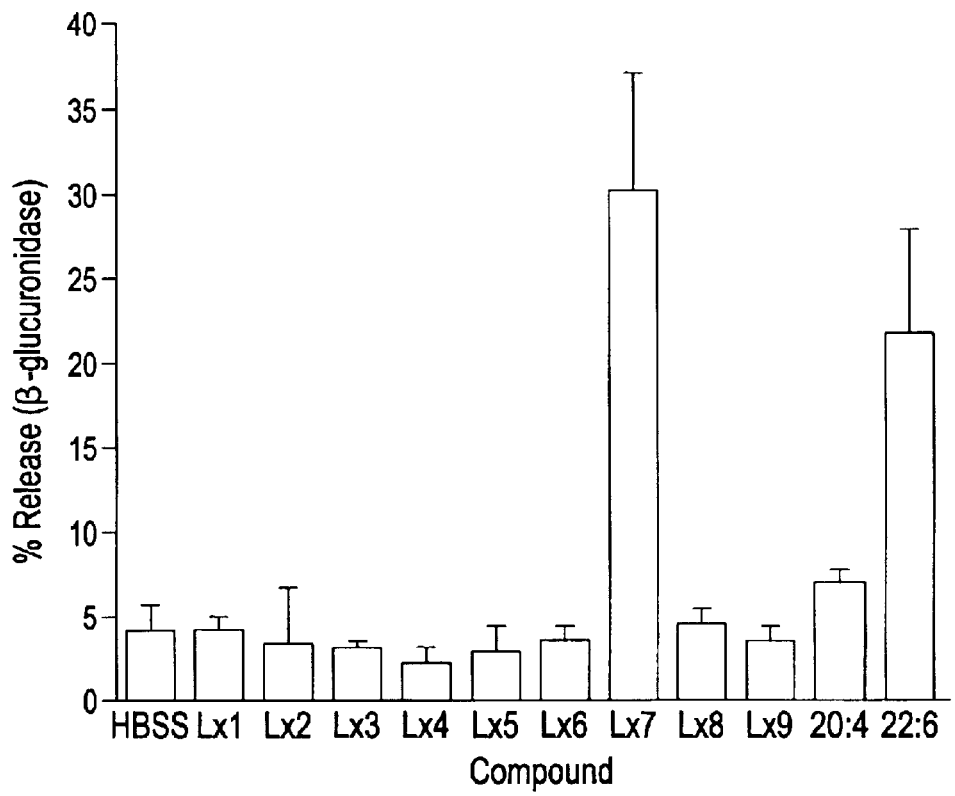
FIG. 8 illustrates the effects of Lx compounds on the release of β-glucuronidase. The results are means +/−SEM of 3–8 experiments. All compounds were tested at 20 $\mu$g/ml.
Figure 9:
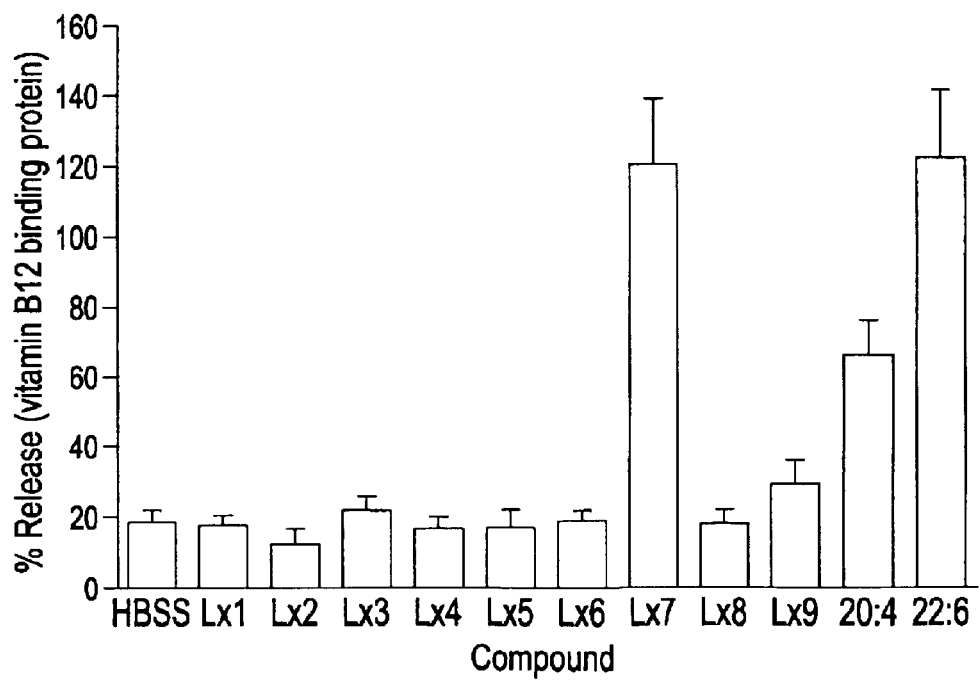
FIG. 9 illustrates the effects of Lx compounds on the release of vitamin B12 binding protein. The results are mean +/−SEM of 3–8 experiments. All compounds were tested at 20 $\mu$/ml.

The pattern of neutrophil activation, as shown in FIG. 7, was reflected also in the degranulation response. Both in relation to release of vitamin B12 binding protein (specific granule maker) and β-glucuronidase (azurophilic granule marker), all of the Lx compounds except for Lx7 were poor inducers of the release of vitamin B12 binding protein as well as release of β-glucuronidase. FIG. 8 illustrates the effects of Lx compounds on the release of β-glucuronidase, and FIG. 9 illustrates the effects of Lx compounds on the release of vitamin B12 binding protein. In each case, the results are means ±SEM of 3–8 experiments. All compounds were tested at 20 µg/ml. Interestingly, Lx7 was as potent as 20:4n-6 and 22:6n-3 in stimulating degranulation.

(4) In Vivo Studies with Chemically Engineered PUFA and Related Compounds on *P. berghei*

Figure 10:
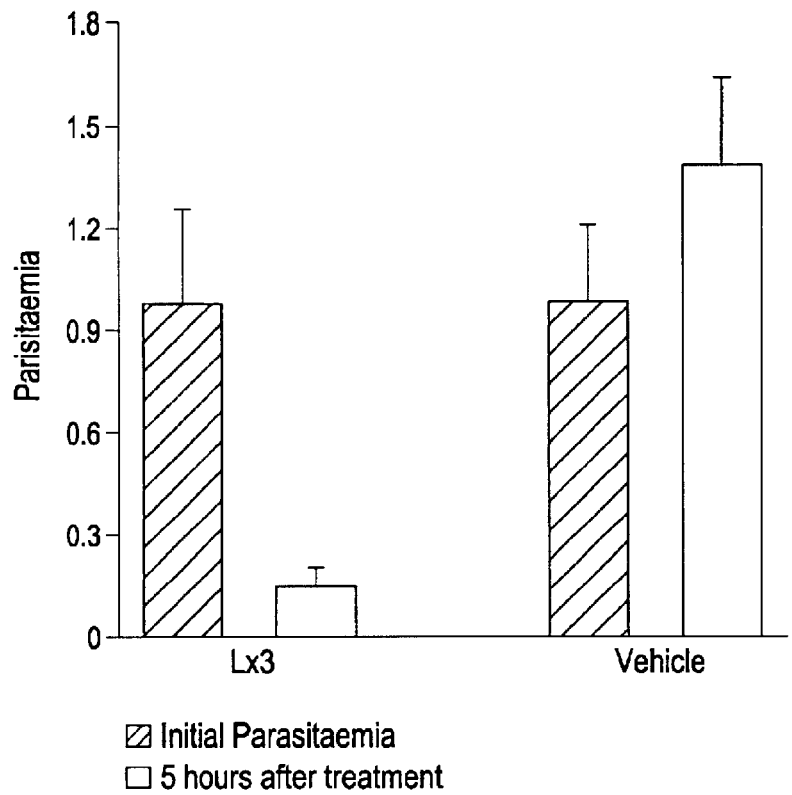
FIG. 10 the effect of Lx3 on the level of *P. berghei* parasitemia on mice. Results are the means +/−SEM of five mice per group. Mice were infected intraperitoneally with the parasite and when an approptiate parasitemia was reached they were treated intravenously with 40 mg/kg weight of MP#. Mice treated with a single dose of Lx3 intravenously showed a marked drop in circulating parasites within 5 hours after injection.

In other sets of experiments, the effects of Lx3 were examined in vivo in mice infected with *P. berghei*. FIG. 10 illustrates the effect of Lx3 on the level of *P. berghei* parasitaemia in the mice. Results are the means ±SEM of five mice per group. Mice were infected intraperitoneally with the parasite and when an appropriate parasitaemia was reached they were treated intravenously with 40 mg/kg weight of MP3. These experiments showed that mice tolerated Lx3 quite well and that mice treated with a single dose intravenously showed a marked drop in circulating parasites (parasitaemia) within 5 h after injection. Similar results were obtained with changes in the period of observation (Table 5) as well as with a different species, *P. chabaudi* (data not presented).

TABLE 5

Effects of Lx3 on *P berghei* infection

| Time (h) after infection | Treatment | |
|---|---|---|
| | DPC | Lx3 |
| 4 | 0.75 ± 0.04 | 0.18 ± 0.05 |
| 22 | 0.83 ± 0.40 | 0.30 ± 0.10 |
| 28 | 1.20 ± 0.54 | 0.14 ± 0.05 |
| 46 | 4.16 ± 0.91 | 0.40 ± 0.14 |

Mice were treated at one day prior to infection with 2 doses of 40 mg/kg body weight and then another dose 60 min prior to infection (0 time) on the following day. The parasitaemia was checked 4 h later and at the times stipulated in the Table. The animals were treated with either DPC or Lx3 twice a day 30 min after taking a parasitaemia reading. The results are presented as mean ±SEM of parasitaelnia of 4 mice per group.

Figure 11:
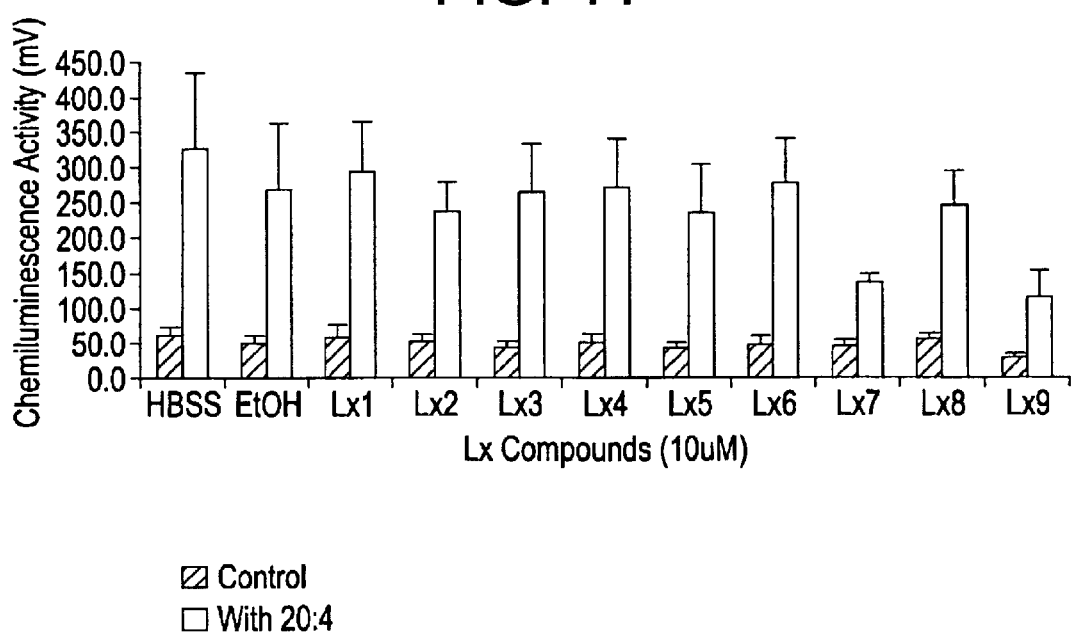
FIG. 11 shows the effects of Lx compounds on AA-enhanced chemiluminescence in human neutrophils.

E. Anti-inflammatory Properties of Lx Compounds (1) Effect of Lx Compounds on AA-Enhanced Chemiluminescence in Human Neutrophils Arachidonic acid (AA) is a natural agonist which stimulates oxygen radical production in neutrophils leading to tissue damage during inflammation. Studies were conducted to examine whether or not the Lx compounds could antagonise the effects of AA. Neutrophils were pretreated with Lx compounds and then examined for chemiluminescence response to AA addition. The data above show that some Lx compounds inhibit the ability of AA to stimulate oxygen radical production. This is particularly evident with Lx7 and Lx9. The effect of Lx compounds on AA-enhanced chemiluminescence in human neutrophils is shown graphically in FIG. 11.

AA could be a target for anti-inflammatory activity. Therefore, some Lx compounds could be used as anti-inflammatory agents.

(2) Effects of Lx Compounds on Lymphocyte Activation and Cytokine Production

The effects of the nitroalkanes (Lx1–Lx5) on lymphocyte activation and cytokine production were examined. The ability of the PUFA to suppress mitogen-induced proliferation in response to PHA and *S. aureus*, and to inhibit cytokine production (TNFα and IFNγ), was assessed.

Data on Lx1, Lx2, Lx3, and Lx4 indicate that, of these compounds, Lx4 is worthy of further investigation, particularly with respect to effects on IFNγ production (Table 6), and additional experiments are in progress.

TABLE 6

Effects of Lx compounds on production of cytokines by human peripheral blood leukocytes

| | % Inhibition (compared to control) | |
|---|---|---|
| Compound | Stimulus (*S. aureus*) TNF-α | Stimulus (PHA) IFN-γ |
| Lx2 | 43.7 | 40.4 |
| Lx3 | 48.2 | 37.6 |
| Lx4 | 34 | 79.8 |

All PUFA were used at 20 μM. (TNF = tumour necrosis factor; IFN = Interferon)

Studies in paw oedema indicate that the compound 4a is inflammatory while the compound 4d may be either inflammatory or anti-inflammatory depending on the dose administered, the eliciting agent and the time of measurement of the response.

F. Antioxidant Properties of the β and γ Oxa and Thia Fatty Acids

Other analogues of PUFAs targeted in this project were the oxa and thia fatty acids, owing to their potential as antioxidants. Compounds of types 16–19, as identified in Table 7, were constructed as PUFA analogues having the property of resistance to β-oxidation[47,13].

TABLE 7

Structure and nomenclature of the oxa and thia fatty acid analogues and other thia compounds

| Structure | Systematic name | WCH | Thesis |
|---|---|---|---|
| 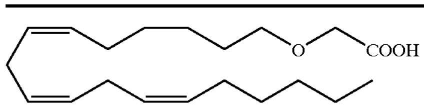 | (Z,Z,Z)-(octadeca-6,9,12-trienyloxy) acetic acid | 16 | MP4 |
| 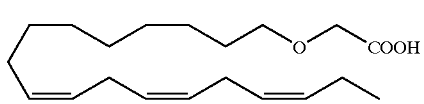 | (Z,Z,Z)-(octadeca-9,12,15-trienyloxy) acetic acid | 17 | MP5 |

TABLE 7-continued

Structure and nomenclature of the oxa and thia fatty acid analogues and other thia compounds

| Structure | Systematic name | WCH | Thesis |
|---|---|---|---|
| [structure] | (all-Z)-(eicosa-5,8,11,14-tetraenylthio) acetic acid | 18 | MP8 |
| [structure] | 3-[(all-Z)-(eicosa-5,8,11,14-tetraenylthio) propionic acid | 19 | MP11 |
| [structure] | 3-[(3Z,6Z)-nona-3,6-dienylthiopropionic acid | 106 | |
| [structure] | 3-tetradecylthiopropionic acid | 108 | |
| [structure] | 2-tetradecylthiopropionic acid | 109 | |
| [structure] | propyl(all-Z)-eicosa-5,8,11,14-tetraenylpropyl sulfide | 110 | |
| [structure] | propyltetradecyl sulfide | 111 | |
| [structure] | 3-[(Z,Z,Z)-(octadeca-9,12,15-trienylthio)]-propionic acid | 112 | MP13 |
| [structure] | 3-(tetradecylsulfinyl) propionic acid | 113 | |
| [structure] | 2-(tetradecylsulfinyl) acetic acid | 114 | |

Subsequently, the autoxidation of compounds 16–19 and their effects on the autoxidation of arachidonic acid were investigated. In these experiments, a thin film assay method was employed. For each reaction, arachidonic acid was mixed with one of the synthetic compounds 16, 17, 18 or 19 at 1:1 ratio with or without the radical initiator, azobisisobutyronitrile (AIBN). A reverse phase HPLC method was used to simultaneously measure the relative amounts of arachidonic acid and the synthetic compounds 16, 17, 18 or 19 recovered following 60 or 70 hours or 7 days of thin film autoxidation. Part of the results are summarised in Table 8.

TABLE 8

Percentages of arachidonic acid and compounds 16–19 recovered following thin film autoxidation. (The initial ratio of arachidonic acid to each other PUFA compound is 1:1).

| | Percentage of compounds recovered Reaction conditions | | |
|---|---|---|---|
| Compound | no additive 70 h | no additive 7 day | 10% AIBN 60 h |
| Arachidonic acid + 16 | 97% | 23% | 17% |
| 16 | 88% | 27% | 11% |
| Arachidonic acid + 17 | 92% | 30% | 44% |
| 17 | 102% | 41% | 49% |
| Arachidonic acid + 18 | 98% | 68% | 87% |
| 18 | 99% | 28% | 57% |
| Arachidonic acid + 19 | 101% | 102% | 100% |
| 19 | 98% | 96% | 96% |

As shown in Table 8, arachidonic acid underwent rapid autoxidation in the presence of compound 16, as reflected by reduction in the percentage of recovered arachidonic acid (23 or 17%) after 7 days of autoxidation without the additive AIBN or after 60 h with 10% AIBN. The data showed that arachidonic acid also underwent a substantial degree of autoxidation in the presence of compounds 17 and 18 during the same periods. In contrast, autoxidation of arachidonic acid was completely inhibited during the testing periods when the thin film reaction was carried out in the presence of the γ-thia fatty acid, 3-[(all-Z)-(eicosa-5,8,11,14-tetraenylthio)] propionic 19, even when the reaction contained the radical initiator AIBN. The result indicates that compound 19 is an antioxidant.

The specific objective of this project in regard to the thia fatty acids was to examine the basis of the selective antioxidant activity of the γ-thia fatty acid 19. This was to be done by synthesis of a series of analogues of compound 19 and subsequent investigation of their effects on arachidonic acid autoxidation. The analogues include an unsaturated γ-thia fatty acid with two methylene-interrupted cis double bonds, which brings unsaturation closer to the sulfur than is the case in compound 19, saturated γ-thia and β-thia fatty acids, and unsaturated and saturated sulfides. A thin film method on Petri-dishes was to be employed for assessing autoxidation of arachidonic acid in the presence of the thia fatty acids and sulfides, in conjunction with a reversed phase HPLC technique for analysis of recovered arachidonic acid and thia fatty acids and sulphides. The aim was to examine if the degree of unsaturation, the carboxyl group and the location of sulfur in the thia fatty acids affects their antioxidative activity.

(1) Effects of Thia Polyunsaturated Fatty Acids and Sulfides on Autoxidation of Arachidonic Acid.

Having prepared analogues of compound 19, the subsequent aim was to investigate their effects on autoxidation of arachidonic acid. Based on previous work, a thin film method was employed for this purpose, in conjunction with a reverse phase HPLC technique for analysis of the recovered arachidonic acid and thia PUFAs and sulfides, with lauric acid as an internal standard.

Autoxidation of arachidonic acid was conducted in the presence of compound 19 and lauric acid. Stock solutions of arachidonic acid, compound 19 and lauric acid in dichloromethane with equal concentrations were added to a 25 ml round-bottomed flask, and the solvent was evaporated to leave a thin film on the internal surface of the flask. The flask was then filled with oxygen and kept in the dark. The percentages of arachidonic acid and compound 19 remaining after 7 days were measured by HPLC. The same assay was carried out simultaneously with several flasks but the results were not reproducible. The variation was attributed to differences in oxygen concentration and the surface area of the thin films formed in the flasks. Therefore, in order to establish a reproducible assay for the analysis of the autoxidation of arachidonic acid, Petri-dishes with uniform size (80 mm in diameter) were used instead of flasks for thin film formation and the oxidation was carried out by placing the Petri-dishes in a dessicator filled with oxygen. To assess this method, thin firms of arachidonic acid with lauric acid as a standard were prepared on six Petri-dishes using identical treatment, and then subjected to oxidation in the same dessicator filled with oxygen. After 24 h, the percentage of arachidonic acid recovered following autoxidation in each Petri-dish was determined by HPLC. The results showed that the variation in the data obtained for the six samples was smaller than 7%. The advantage of using a Petri-dish over a flask is that the thin films on each Petri-dish are spread over the same area, and each Petri-dish is exposed to oxygen to the same extent.

Using the Petri-dish assay method, the effects of the thia PUFAs and sulfides 106 and 108–111, along with compounds 18, 19 and 3-[(Z,Z,Z)-(octadeca-9,12,15-trienylthio)] propionic acid 112 which were available in the laboratory, on the autoxidation of arachidonic acid, were examined. In addition, the stability of these compounds in the presence of arachidonic acid was also investigated. Arachidonic acid and lauric acid as a standard were mixed with each sulfur compound at different ratios and the mixtures were subjected to thin film autoxidation. The mixtures were analysed by HPLC after 1,2,3,5 and 7 days. The results are summarised in Tables 9–17 below. The yields given in the tables are the mean values of at least duplicate experiments, which showed good reproducibility with standard errors within ±12%.

TABLE 9

Percentage of arachidonic acid recovered following autoxidation

| Autoxidation time (days) | Arachidonic acid (%) |
|---|---|
| 1 | 91 |
| 2 | 20 |
| 3 | 16 |
| 5 | 12 |
| 7 | N.D. |

N.D. = None detectable

TABLE 10

Percentages of arachidonic acid and compound 18 recovered following autoxidation

| Autoxidation time (days) | Arachidonic acid (%) | Compound 18 (%) |
|---|---|---|
| Using a ratio of arachidonic acid and compound 18 of 1:1. | | |
| 1 | 68 | 26 |
| 2 | 29 | 7 |
| 3 | 10 | N.D. |
| 5 | 7 | N.D. |
| 7 | 5 | N.D. |

TABLE 11

Percentages of arachidonic acid and compound 19 recovered following autoxidation

| Autoxidation time (days) | Arachidonic acid (%) | Compound 19 (%) |
|---|---|---|
| A: Using a ratio of arachidonic acid and compound 19 of 1:1 | | |
| 1 | 99 | 99 |
| 2 | 100 | 100 |
| 3 | 99 | 99 |
| 5 | 99 | 98 |
| 7 | 98 | 99 |
| B: Using a ratio of arachidonic acid and compound 19 of 2:1 | | |
| 1 | 100 | 98 |
| 2 | 99 | 96 |
| 3 | 100 | 96 |
| 5 | 98 | 94 |
| 7 | 97 | 90 |
| C: Using a ratio of arachidonic acid and compound 19 of 2:1, with AIBN at 10% the amount of arachidonic acid | | |
| 1 | 100 | 98 |
| 2 | 98 | 95 |
| 3 | 94 | 80 |
| 5 | 49 | 47 |
| 7 | 35 | 43 |

TABLE 11-continued

Percentages of arachidonic acid and compound 19 recovered following autoxidation

| Autoxidation time (days) | Arachidonic acid (%) | Compound 19 (%) |
|---|---|---|
| D: Using a ratio of arachidonic acid and compound 19 of 10:1 | | |
| 1 | 99 | 95 |
| 2 | 99 | 87 |
| 3 | 87 | 38 |
| 5 | 42 | N.D. |
| 7 | 17 | N.D. |

TABLE 12

Percentages of arachidonic acid and compound 106 recovered following autoxidation

| Autoxidation time (days) | Arachidonic acid (%) | Compound 106 (%) |
|---|---|---|
| A: Using a ratio of arachidonic acid and compound 106 of 1:1 | | |
| 1 | 99 | 98 |
| 2 | 98 | 96 |
| 3 | 99 | 98 |
| 5 | 100 | 97 |
| 7 | 101 | 98 |
| B: Using a ratio of arachidonic acid and compound 106 of 2:1 | | |
| 1 | 98 | 97 |
| 2 | 99 | 98 |
| 3 | 98 | 97 |
| 5 | 99 | 97 |
| 7 | 99 | 100 |
| C: Using a ratio of arachidonic acid and compound 106 of 10:1 | | |
| 1 | 101 | 94 |
| 2 | 101 | 84 |
| 3 | 99 | 59 |
| 5 | 79 | N.D. |
| 7 | 16 | N.D. |

TABLE 13

Percentages of arachidonic acid and compound 108 recovered following autoxidation

| Autoxidation time (days) | Arachidonic acid (%) | Compound 108 (%) |
|---|---|---|
| Using a ratio of arachidonic acid and compound 108 of 1:1 | | |
| 1 | 98 | 99 |
| 2 | 93 | 91 |
| 3 | 79 | 86 |
| 5 | 30 | 44 |
| 7 | N.D. | 37 |

TABLE 14

Percentages of arachidonic acid and compound 109 recovered following autoxidation

| Autoxidation time (days) | Arachidonic acid (%) | Compound 109 (%) |
|---|---|---|
| Using a ratio of arachidonic acid and compound 109 is 1:1 | | |
| 1 | 53 | 50 |
| 2 | 10 | 16 |

TABLE 14-continued

Percentages of arachidonic acid and compound 109 recovered following autoxidation

| Autoxidation time (days) | Arachidonic acid (%) | Compound 109 (%) |
|---|---|---|
| 3 | N.D. | 17 |
| 5 | N.D. | 17 |
| 7 | N.D. | 16 |

TABLE 15

Percentages of arachidonic acid and compound 110 recovered following autoxidation

| Autoxidation time (days) | Arachidonic acid (%) | Compound 110 (%) |
|---|---|---|
| A: Using a ratio of arachidonic acid and compound 110 of 1:1 | | |
| 3 | 100 | 99 |
| 7 | 100 | 100 |
| B: Using a ratio of arachidonic acid and compound 110 of 10:1 | | |
| 1 | 97 | 85 |
| 2 | 89 | 22 |
| 3 | 67 | N.D. |
| 5 | 24 | N.D. |
| 7 | 10 | N.D. |

TABLE 16

Percentages of arachidonic acid and compound 111 recovered following autoxidation

| Autoxidation time (days) | Arachidonic acid (%) | Compound 111 (%) |
|---|---|---|
| A: Using a ratio of arachidonic acid and compound 111 of 1:1 | | |
| 1 | 100 | 101 |
| 2 | 98 | 91 |
| 3 | 98 | 92 |
| 5 | 98 | 92 |
| 7 | 97 | 90 |
| B: Using a ratio of arachidonic acid and compound 111 of 10:1 | | |
| 1 | 99 | 81 |
| 2 | 99 | 63 |
| 3 | 97 | 38 |
| 5 | 68 | N.D. |
| 7 | 17 | N.D. |

TABLE 17

Percentages of arachidonic acid and compound 112 recovered following autoxidation

| Autoxidation time (days) | Arachidonic acid (%) | Compound 112 (%) |
|---|---|---|
| A: Using a ratio of arachidonic acid and compound 112 of 1:1 | | |
| 1 | 100 | 100 |
| 2 | 99 | 98 |
| 3 | 98 | 97 |
| 5 | 99 | 97 |
| 7 | 93 | 86 |
| B: Using a ratio of arachidonic acid and compound 112 of 10:1 | | |
| 1 | 82 | 25 |
| 2 | 33 | N.D. |

TABLE 17-continued

Percentages of arachidonic acid and compound 112 recovered following autoxidation

| Autoxidation time (days) | Arachidonic acid (%) | Compound 112 (%) |
|---|---|---|
| 3 | 17 | N.D. |
| 5 | 4 | N.D. |
| 7 | N.D. | N.D. |

The results in Table 9 show that arachidonic acid undergoes autoxidation readily. After 2 days, only 20% of the arachidonic acid remained. As shown in Tables 11A and 12A, the introduction of compound 19 or 106 at a ratio of 1:1 results in almost complete prevention of autoxidation of arachidonic acid, even over the extended 7 days assay period, indicating that compounds 19 and 106 are both effective antioxidants. When the concentration of compounds 19 and 106 was reduced to one-tenth that of arachidonic acid (Tables 11D and 12C), autoxidation of arachidonic acid was very slow over the first 3 days, but faster after that period, coinciding with decomposition of compounds 19 and 106. The antioxidative activity of compounds 19 and 106 is quite similar. Compound 112 was also effective as an antioxidant when used in a 1:1 ratio with arachidonic acid (Table 17A), but it was less effective than either compound 19 or 106 at the lower concentration (Table 17B).

The unsaturation of compounds 19, 106 and 112 is not essential for antioxidant activity. Neither is the carboxyl group. Compound 111 is saturated and neither compound 110 nor 111 possesses a carboxyl group. Yet when present in 1:1 ratio with arachidonic acid, both of the sulfides 110 and 111 effectively inhibit the oxidation of arachidonic acid (Tables 15A and 16A). Even when the amount of the sulfides 110 and 111 used was reduced to one-tenth that of arachidonic acid, they were still effective antioxidiants (Tables 15B and 16B). Apparently the sulfur alone is the key to the antioxidant activity of compounds 19, 106, 108 and 110–112.

By contrast, the autoxidation of arachidonic acid is not significantly inhibited by either of the β-thia fatty acids 18 and 109 (Tables 10 and 14). To examine possible reasons for this lack of antioxidative activity, the chemical stability of compounds 18 and 109 in the absence of arachidonic acid was investigated. For comparison, the stability of compounds 19, 106, 108 and 110–112 was also examined. Each compound was studied as a thin film under oxygen as described above. Samples were removed and analysed by $^1$H NMR spectroscopy regularly for up to six weeks. The results showed that compounds 19, 106 and 108–112 are all stable under these conditions. However, the unsaturated β-thia PUFA 18 decomposed after 7 days. The product mixture was analysed by $^1$H NMR, which showed a complex mixture of products. The results for compound 109 show that β-thia PUFAs are not inherently unstable, so the decomposition of compound 18 presumably relates to its unsaturation. This is consistent with compound 109 decomposing in the presence of arachidonic acid, but not alone.

(2) Mechanism of Antioxidant Activity

The saturated γ-thia PUFA 108 is converted to the sulfoxide 113 on autoxidation in the presence of arachidonic acid, but not alone. Therefore, it seems likely that hydroperoxides of arachidonic acid are responsible for production of the sulfoxide 113.

As mentioned earlier, the γ-thia fatty acids 19, 106, 108 and 112 are effective antioxidants, but the β-thia fatty acids 18 and 109 are not. To further investigate the possible involvement of hydroperoxide-induced sulfoxide formation in the antioxidant behaviour of the γ-thia and β-thia fatty acids 18, 19, 106, 108, 109 and 112, compounds 108 and 109 (in a ratio of 1:1 in $CH_2Cl_2$) were allowed to react with tert-butyl hydroperoxide.

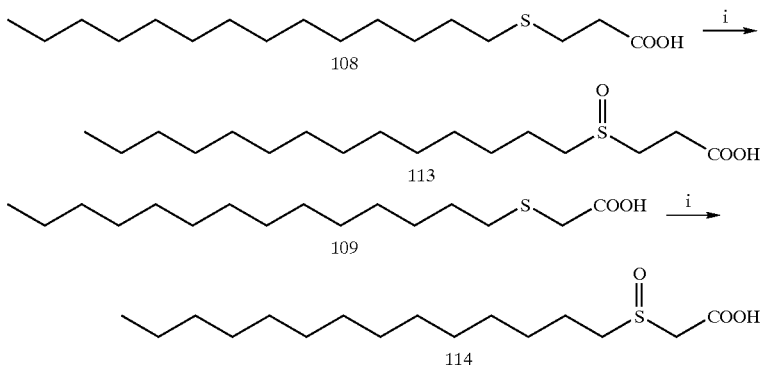

i: tert-butyl hydroperoxide, $CH_2Cl_2$, RT

The reaction was monitored by TLC and $^1$H NMR analysis. This showed that 55% of compound 109 was converted to the product 114 after 9 h, while compound 108 was completely converted to the corresponding sulfoxide 113 during the same period. NMR spectral analysis of the product from compound 109 isolated after completion of the reaction (48 h) showed that it is the sulfoxide 114. The $^1$H NMR spectrum of compound 114 contains two multiplets at δ2.88–3.07 and two doublets at δ3.63–3.86 corresponding to the methylene protons on the carbons adjacent to sulfur. The $^{13}$C NMR spectrum shows characteristic peaks at δ52.27 and 53.47 representing the corresponding carbons.

This shows that both the γ-thia fatty acid 108 and the β-thia fatty acid 109 react with organic hydroperoxides to form sulfoxides, but the reaction rate is much faster for the γ-thia fatty acid 108. This explains why the γ-thia fatty acid 108 is a much better antioxidant than the β-thia fatty acid 109. The former reacts fast with and destroys hydroperoxides, which are initiators of free-radical oxidation chain processes. Consequently, it functions as an effective antioxidant. In contrast, the saturated β-thia fatty acid 109 reacts relatively slowly with hydroperoxides and therefore is ineffective as an antioxidant.

General conclusions may be drawn from these preliminary experiments. It appears that β-thia fatty acids such as compound 18 and 109 may be ineffective as antioxidants due to the proximity of the sulfur to the carboxyl group. This may affect the nucleophilicity of the sulfur or introduce steric hindrance in the reactions with hydroperoxides. In β-thia fatty acids, the carboxyl group is relatively close to the sulfur and consequently the nucleophilicity of the sulfur may be weakened because of the electron-withdrawing nature of the carboxyl group. The proximity of the carboxyl group to the sulfur in the β-thia fatty acids may also cause steric hindrance to the nucleophilic substitution process. In the γ-thia fatty acids 19, 106, 108 and 112 and the sulfides 110 and 111, however, the carboxyl group is either absent or more remote.

Figure 12:
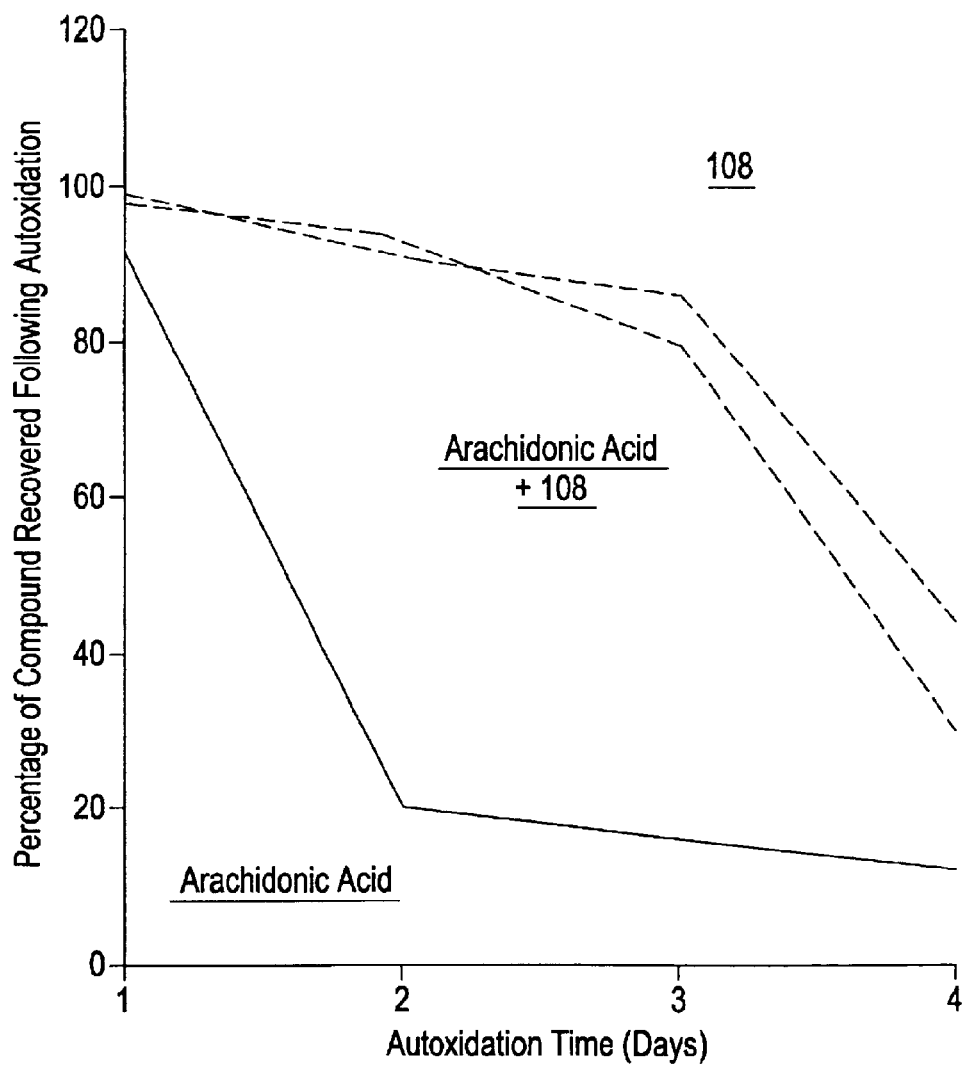
FIG. 12 illustrates the antioxident effect of compound 108.

Earlier studies indicated that some sulfoxides are more effective inhibitors of hydrocarbon autoxidation than the parent sulfides. However, the results of the present work indicate that sulfides but not sulfoxides have antioxidant activity. For instance, protection conferred by slow conversion of the sulfide 108 to the sulfoxide 113 (Table 18) contrasts with rapid autoxidation of arachidonic acid alone (Table 9) and is summarised in FIG. 12. FIG. 12 was compiled from the data of Tables 9 and 18, and illustrates the antioxidant effect of compound 108.

TABLE 18

Percentages of arachidonic acid and compound 108 recovered following autoxidation

| Autoxidation time (days) | Arachidonic acid (%) | Compound 108 (%) |
|---|---|---|
| Using a ratio of arachidonic acid and compound 108 of 1:1 | | |
| 1 | 98 | 99 |
| 2 | 93 | 91 |
| 3 | 79 | 86 |
| 5 | 30 | 44 |
| 7 | N.D. | 37 |

α-Tocopherol (vitamin E) is a widely used, naturally occurring, phenolic antioxidant which inhibits free-radical chains in biological systems. The γ-thia fatty acids 19, 106, 108 and 112, and the sulfides 110 and 111, of the present work should be more readily miscible in lipids than is α-tocopherol. Therefore, they may be more effective antioxidants than α-tocopherol in this environment.

CONCLUSION

The oxidation of polyunsaturated fatty acids (PUFAs) plays an important role in biological systems and some of the metabolic products from PUFA oxidation are important biological mediators that have been implicated in the pathology of many diseases such as asthma, inflammation and allergy. There are three major oxidative pathways for PUFAs: β-oxidation, autoxidation and oxidation catalysed by enzymes such as cyclooxygenases and lipoxygenases. The aim of this research was to pursue analogues of PUFAs that are effective in control of both non-enzymatic and lipoxygenase-catalysed PUFA oxidation and would therefore be potentially useful as therapeutic agents for the control of diseases related to the oxidative pathways. Such analogues were required to display certain properties including resistance to β-oxidation, antioxidant activity and selective inhibition of different lipoxygenases.

The main group of compounds targeted in this project was the nitro analogues of PUFAs. They were expected to be potentially useful due to their generally high stability and the chemical similarity of the nitro group to the carboxyl group. The other group of compounds investigated was the γ-thia fatty acids. The γ-thia fatty acid, 3[all-Z]-(eicosa-5,8,11,14-tetraenylthio)]propionic acid, had been previously shown to inhibit autoxidation of arachidonic acid. Such compounds were expected to be useful lipid antioxidants due to their miscibility with and structural similarity to natural fatty acids.

From the nine nitro analogues of PUFAs that were synthesised, including long chain nitroalkanes, γ-nitro fatty acids and carboxyethyl nitro fatty acids, (all-Z)-4-nitrotricosa-8,11,14,17-tetraenoic acid has been identified as a good substrate of soybean 15-LO and a 12-LO from porcine leukocytes. The substrate activity of this compound with the soybean 15-LO is comparable to that of arachidonic acid, which is a major substrate of the lipoxygenase.

A more significant outcome of this work was the identification of 4-nitrohenicosanoic acid, 3-(all-Z)-nonadeca4,7,10,13-tetraeny]-3-nitropertane-1,5-dicarboxylic acid and 3-heptadecyl-3-nitropentane-1,5-dicarboxylic acid as selective inhibitors of 5-LO, 12-LO and 15-LO catalysed oxidation of arachidonic acid, respectively. Although a large number of inhibitors have been reported for these three lipoxygenases, so far few inhibitors have entered clinical trials and no agents that are selective for 15-LO vs 5-LO (or vs 12-LO) are available.[48]

Selective inhibition of a specific lipoxygenase is particularly desirable for treatment of diseases related to these metabolic pathways. Non-selective inhibitors have the disadvantages of causing possible side effects. For instance, asthma has been treated as an inflammatory disease, and corticosteroids are the therapy of choice for the inflammatory component of asthma.[49] Although this class of drugs provides powerful anti-inflammatory effects in most patients, these effects are not specific and in some cases result in serious side effects. Since leukotrienes, a family of inflammatory mediators generated through the 5-LO pathway, have been shown to enhance bronchoconstriction and airway mucus secretion, agents that target the specific inflammatory pathway have been developed to treat asthma by modulating leukotriene activity. So far, specific leukotriene receptor antagonists and synthesis inhibitors have been extensively studied in laboratory-induced asthma and currently show promise in clinical trials; one leukotriene receptor antagonist (zafirlukast) and one 5-LO inhibitor (zileuton) were recently approved for the treatment of asthma.[49] The identification of the three nitro analogues of PUFAs having selective inhibition activity with the three lipoxygenases may lead toward a new class of drugs with specificity and reduced side effects for treating diseases that are associated with lipoxygenase pathways.

Studies to examine the basis of the antioxidant behaviour of 3-(all-Z)-(eicosa-5,8,11,14-tetraenylthio)]propionic acid suggest that the activity results from interaction with the hydroperoxide products of PUFA autoxidation. Hydroperoxides are initiators of the radical-chain autoxidation process and decomposition of these compounds through reaction with γ-thia fatty acids and sulfides can therefore reduce the rate of autoxidation. This work showed that the key structural component required for antioxidant activity is a sulfur and neither a carboxyl group nor unsaturation play direct roles. Thus, all the γ-thia fatty acids and sulfides tested showed substantial antioxidant activity on arachidonic acid autoxidation. β-thia fatty acids were not antioxidants, probably due to their relatively slow reaction with hydroperoxides. The closeness of the carboxyl group to the sulfur in the β-thia fatty acids may cause steric hindrance or reduce the nucleophilicity of the sulfur. These data may provide useful information for the design of antioxidants based on destruction of the hydroperoxide products of PUFA autoxidation.

It is evident that malaria is one of the most devastating diseases facing our community today. Our ability to treat patients has been severely compromised by the significant increase in drug resistance, such as chloroquine resistance. We have now described a new class of antimalarial agents: the Lx1 to Lx9 compounds. The most promising of these were Lx2 and Lx3. Lx3 was examined in detail and found to be very active against the human malarial parasite *Plasmodium falciparum*. The agent was active also against a chloroquine resistant isolate. Thus this compound has the additional advantage of being able to be used against drug resistant malaria. It is also likely to act synergistically with other antimalarial drugs. Lx3 was also found to be active in an experimental model of malaria, *P. berghei* infections in mice, given either prophylactically or curatively.

The work showed that Lx3 was much more readily taken up (up to tenfold) by *P. falciparum* infected erythrocytes than normal erythrocytes. Its action was primarily the killing of the late ring stage to immature schizonts of the asexual stage of the parasite. Unlike other fatty acids previously shown to be bound to albumnin and their activity quenched by serum, the activity of Lx3 was not inhibited by serum. Unlike other fatty acids, the Lx compounds did not cause non-specific activation of neutrophils and release of oxygen radicals or the release of granule constituents. Thus they have the advantage of not displaying any of the pathology inducing activity seen with other fatty acids. Lx compounds will have broad spectrum antimicrobial activity, in particular against infection caused by protozoan parasites. In addition, they are active against viruses, bacteria and fungi, especially as the nitro group may overcome the problem presented by the carboxyl group.

Some of the Lx compounds which did not have appreciable antimalarial activity (e.g. Lx7 and Lx9) inhibited the arachidonic acid response which is related to inflammation, showing that Lx compounds can be used as agents to inhibit diseases which have an inflammatory response basis, such as asthma, inflammatory bowel disease, arthritis, reperfusion injury, cystic fibrosis etc.

Some Lx compounds inhibited two important cytokines, TNF and IFNγ, which play major roles in inflammatory diseases. These compounds have uses in treating and managing a wide-range of diseases in which these cytokines have been shown to be of major importance. Transplantation of organs and other grafts will also benefit from the use of Lx compounds as immunosuppressive agents.

The thia and sulfinyl compounds of the invention also have antioxidant properties, and may be incorporated in pharmaceutical or cosmetic compositions, in particular to prevent odixation of polyunsaturated fatty acids.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Ferrante, A., Hii, C. S. T., Huang, Z. H., Rathjen, D. A. In *The Neutrophils: New Outlook for the Old Cells*. (Ed. Gabrilovich, D.) Imperial College Press (1999) 4: 79–150.
2. Sinclair, A., and Gibson, R. (eds) 1992. Invited papers from the Third International Congress. American Oil Chemists' Society, Champaign, Ill. 1–482.
3. Freedman, S. D., Katz, M. H., Parker, E. M., Laposata, M., Urman, M. Y. and Alvarez, J. G. *P.N.A.S.* bx;196(24):13995–14000 (1999).
4. Krombout, D. *Nutr. Rev.* 50:49–53 (1992).
5. Kinsella, J. E., Lokesh, B., Stone R. A. *Am. J. Clin. Nutr.* 52:1–28 (1990)
6. Kumaratilake, L. M., Robinson, B. S., Ferrante, A., Poulos A. *J. Am. Soc. Clin. Investigation* 89: 961–967 (1992).
7. Weber, P. C. *Biochem. Soc. Trans.* 18: 1045–1049 (1990).
8. Arm, J. P., and Lee, T. H. *Clin. Sci.* 84:501–510 (1993).
9. Thien, F. K. C. K., and Walters, E. H. *Pros. Leuko and Essential* 52:271–288 (1995).
10. Ford-Hutchinson, A. W. *Crit. Rev. Immunol* 10(1): 1 (1990).
11. Bates, E. J. *Pros. Leuko and Essential.* 53: 75–86 (1995).
12. Ferrante, A., Poulos, A., Easton, C. J., Pitt, M. J., Robertson, T. A., Rathjen, D. A. International Patent Application No. PCT/AU95/00677 (1995)-WO96/11908: *Chem. Abstr.* 125:58194 (1996).
13. Pitt, M. J., Easton, C. J., Moody, C. J., Ferrante, A., Poulos, A., and Rathjen, D. A. *Synthesis* 11:1239–1242 (1997).
14. Banes, N. C., Hui, P. K. *Pulmonary Pharmacol.* 6(1): 3–9 (1993).
15. Kornblum, N., Taub, B., Ungnade, H. E. *J. Am. Chem. Soc.* 76:3209–3211 (1954).
16. Chasar, D. W. *Synthesis* 841–842 (1982).
17. Pollini, G. P., Barco, A., and de Guili, G. *Synthesis*. 44–45 (1972).
18. Corey, E. J., and Suggs, J. W. *Tetrahedron Letters* 31:2647–2650 (1975).
19. Rosini, G., Ballini, R., and Petrini, M. *Synthesis* 269–271 (1985).
20. Melton, J., and McMurry, J. E. *J. Org. Chem.* 4(14) (1975).
21. Finkbeiner, H. L., and Wagner, G. W. *J. Org. Chem.* 28:215 (1963).
22. Finkbeiner, H. L., and Stiles, M. *J. Am. Chem. Soc.* 83:616–632 (1962).
23. Hayashi, H.; Nakanishi, K.; Brandon, C.; Marmur, J. *J. Am. Chem. Soc.* 1973, 95, 8749.
24. Kornblum, N.; Taub, B.; Ungnade, H. E. *J. Am. Chem. Soc.* 1954, 76,3209.
25. a) Stiles, M.; Finkbeiner, H. L. *J. Am. Chem. Soc.* 1959, 81, 505.
   b) Finkbeiner, H. L.; Wagner, G. W. *J. Org. Chem.* 1963, 28, 215.
26. Seebach, D.; Lehr, F. Angew. Chem., *Int. Ed. Engl.* 1976, 15, 505.
27. a) Finkbeiner, H. L.; Stiles, M. *J. Am. Chem. Soc.* 1963, 85, 616.
   b) Feuer, H.; Hass, H. B.; Warren, K. S. *J. Am. Chem. Soc.* 1949, 71, 3078.
28. Chasar, D. W. *Synthesis* 1982, 841.
29. Baldwin, J. E.; Au, A.; Christie, M.; Haber, S. B.; Hesson, D. *J. Am. Chem. Soc.* 1975, 97, 5957.
30. Corey, E. J.; Suggs, J. W. *Tetrahedron Lett.* 1975, 31, 2647.
31. Rosini, G.; Ballini, R. *Synthesis* 1988, 833.
32. Ballini, R.; Bosica, G.; Forconi. P. *Tetrahedron* 1996, 52, 1677.
33. Melton, J.; McMurry, J. E. *J. Org. Chem.* 1975, 40, 2138.
34. a) Porter, N. A.; Wolf, R. A.; Yarbro, E. M.; Weenen, H. *Biochem. Biophys. Res. Commun.* 1979, 89, 1058.
   b) Porter, N. A.; Logan, J.; Kontoyiannidou, V. *J. Org. Chem.* 1979, 44, 3177.
   c) Terao, J.; Matsushita, S. *Agric. Biol. Chem.* 1981, 45, 587.
35. Corey, E. J., and Park, H. *J. Am Chem. Soc.* 104: 1750–1752 (1982).

36. Kumaratilake, L. M., Robinson, B. S., Ferrante A. and Poulos, A., *J. Clin. Invest.* 89: 961–967 (1992).
37. Ferrante, A., Poulos, A., Kumaratilake. L. M., Robinson, B. Methods and compositions for treating malaria and other diseases. U.S. Ser. No. 08/170176; European 92912835.3; AU21726/92 (1992).
38. Hardy, S. J., Robinson, B. S., Poulos, A., Harvey, D. P., Ferrante, A. & Murray, A. W. *Eur. J. Biochem.* 198, 801–806 (1991).
39. Bates, E. J., Ferrante, A., Harvey, D. P. and Poulos, A. *J. Leukocyte Biol.* 53:420–426 (1993).
40. Bates, E. J., Ferrante, A., Harvey D. P., Nandoskar, M. and Poulos, A. *J Leuk. Biol.* 54:590–598 (1993).
41. Ferrante, A., Goh, D. H. B., Harvey, D. P., Robinson, B. S., Hii, C. S. T., Bates, E. J., Hardy, S. J., Johnson, D. W. and Poulos, A. *J. Clin. Invest.* 93, 1063–1070 (1994).
42. Hardy, S. J., Ferrante, A., Poulos, A., Robinson, A., Johnson, D. W. and Murray, A. W. *J. Immunol.* 153, 1754–1760 (1994).
43. Bates, E. J., Ferrante. A., Robinson, B., Smithers, L. and Poulos, A. *Atherosclerosis*, 116, 247–259 (1995).
44. Huang, Z. H., Hii, C. S. T., Rathjen, D. A., Poulos, A., Murray, A. W., and Ferrante, A. *Biochem J.* 325, 553–557 (1997).
45. Hardy, S. J., Robinson, B. S., Ferrante, A., Hii, C. S. T., Johnson, D. W., Poulos, A., Murray, A. W. *Biochem. J.* 311, 689–697 (1995)
46. Li, Y., Ferrante, A., Poulos, A. and Harvey, D. P. *J. Clin. Invest.* 97, 1605–1609 (1996)
47. Pitt M J., Easton C J. Fenante A., Poulos, A., Rathjen D A. *Chem. Phys. Lipids* 92: 63–69 (1998).
48. Editorial, *J. Clin. Invest.* 99: 1147–1148 (1997).
49. Wenzel, S. E. *Am. J. Med.* 104:287–300 (1998).

The claims defining the invention are as follows:

1. An isolated compound having the general formula:

wherein A is an unsaturated hydrocarbon chain of 14 to 26 carbon atoms or a derivative thereof selected from the group consisiting of hydroxy, hydroperoxy, epoxy and peroxy; and B is $(CH_2)_n(COOH)_m$ in which n is an integer from 0 to 2 and m is 1 or 2; wherein the $NO_2$ group is a side group on any of the carbon atoms of A.

2. The isolated compound of claim 1, wherein the unsaturated hydrocarbon chain comprises 18 to 22 carbon atoms.

3. The isolated compound of claim 1 wherein the unsaturated hydrocarbon chain comprises 3 to 6 double bonds.

4. The isolated compound of claim 1 wherein the hydrocarbon chain comprises 18 carbon atoms and three double bonds separated by methylene groups, with the first double bond between the $3^{rd}$ and $4^{th}$ or $6^{th}$ and $7^{th}$ carbon atom relative to the omega carbon atom.

5. The isolated compound of claim 1, wherein the compound is (all-Z)-4-Nitrotricosa-8,11,14,17-tetraenoic acid.

6. The isolated compound of claim 1, wherein the compound is 4-[(all-Z)-Nonadeca-4,7,10,13-tetraenyl]-4-nitraheptane-1,7-dicarboxylic acid.

7. A pharmaceutical composition comprising the compound of claim 1 together with a pharmaceutically acceptable carrier or diluent.

* * * * *

UNITED STATES PATENT AND TRADEMARK OFFICE
CERTIFICATE OF CORRECTION

PATENT NO. : 6,924,309 B2
DATED : August 2, 2005
INVENTOR(S) : Antonio Ferrante, Christopher J. Easton and Ling Xia It is certified that error appears in the above-identified patent and that said Letters Patent is hereby corrected as shown below:

<u>Columns 5 and 6,</u>
Table I, line 15, delete "3-[(all-Z)-Nonadeca-4,7,10,13-tetraenyl]4-nitroheptane-1,7-dicarboxylic acid" and insert -- 4-[(all-Z)-Nonadeca-4,7,10,13-tetraenyl]4-nitroheptane-1,7-dicarboxylic acid --.

Signed and Sealed this

Fourteenth Day of February, 2006

JON W. DUDAS
*Director of the United States Patent and Trademark Office*